United States Patent [19]

Chuntharapai et al.

[11] Patent Number: 5,440,021

[45] Date of Patent: Aug. 8, 1995

[54] ANTIBODIES TO HUMAN IL-8 TYPE B RECEPTOR

[76] Inventors: Anan Chuntharapai; Caroline Hébert; Kyung J. Kim; James Lee, all of 460 Point San Bruno Blvd., South San Francisco, Calif. 94080

[21] Appl. No.: 202,056

[22] Filed: Feb. 25, 1994

Related U.S. Application Data

[63] Continuation-in-part of Ser. No. 677,211, Mar. 29, 1991, abandoned.

[51] Int. Cl.$^6$ .................. C07K 16/28; C07K 16/24; C12N 5/22
[52] U.S. Cl. .................. 530/388.22; 530/388.23; 530/389.1; 530/389.2; 435/240.27
[58] Field of Search ............. 424/158.1; 530/388.73, 530/388.23, 389.2, 388.33, 389.1; 435/240.27

[56] References Cited

FOREIGN PATENT DOCUMENTS

WO92/04372 3/1992 WIPO.
WO92/18641 10/1992 WIPO.
WO93/06229 4/1993 WIPO.

OTHER PUBLICATIONS

Chuntharapi, A et al, J. Immunol., 150 (8 part 2):126A, May 21-25, 1993.

Lee, James et al., J. Biol Chem, 267(23):16283-16287, Aug. 15, 1992.

Hebert, C A et al., J. Biol Chem., 268(25):18549-18553, Sep. 5, 1993.

LaRosa, G. J., J. Biol Chem, 267(35):25402-25406, Dec. 15, 1992.

Richman-Eisenstat, J. B. et al., Am. J. Physiol, 264(4 part 1), pp. 413-418, 1993.

Samanta et al., "Identification and characteriation of specific receptors for monocyte-derived neutrophil chemotactic factor (MDNCF) on human neutrophils", J. Exp. Med., 169: 1185-1189 (1989).

Besemer et al., "Specific Binding, Internalization, and Degradation of Human Neutrophil Activating Factor by Human Neutrophil Activating Factor by Human Polymorphonuclear Leukocytes", J. Biol Chem., 264: 17409-17415 (1989).

Grob et al. "Characterization of a Receptor for Human Monocyte-derived Neutrophil Chemotactic Factor/Interleukin-8" J. Biol. Chem., 265:8311-8316 (1990).

Oppenheim et al., "Properties of the noval proinflammatory supergene intercine cytokine family", Annu. Rev. Immunol., 9: 617-648 (1991).

Taylor, C. W., "The role of G proteins in transmembrane signalling", Biochem. J., 272: 1-13 (1990).

Strader et al., "Structural basis of $\beta$-adrenergic receptor function", FASEB, 3: 1825-1832 (1989).

Dixon et al., "Structural features required for ligand binding to the $\beta$-adrenergic receptor", EMBO J., 6(11): 3269-3275 (1987).

Kubo et al., "Cloning, sequencing and expression of complementary DNA encoding the muscarinic acetylcholine receptor", Nature, 323: 411-416 (1986).

Peralta et al., "Distinct primary structures, ligand-binding properties and tissue-specific expression of four human muscarinic acetylcholine receptors", EMBO J., 6: 3923-3929 (1987).

Holmes et al., "Structure and Functional Expression of a Human Interleukin-8 Receptor", Science, 253:1278-1280-(1991).

Murphy and Tiffany, "Cloning of Complementary DNA Encoding a Functional Human Interleukin-8 Receptor", Science, 253: 1280-1283 (1991).

Gearing et al., "Expression cloning of a receptor for (List continued on next page.)

Primary Examiner—David L. Lacey
Assistant Examiner—Susan A. Loring
Attorney, Agent, or Firm—Richard B. Love

[57] ABSTRACT cDNAs encoding a class of receptors, including the IL-8 type B receptor, have been identified in human tissue. Recombinantly produced IL-8 type B receptor is used in the preparation and purification of antibodies capable of binding to the receptor, and in diagnostic assays. The antibodies are advantageously used in the prevention and treatment of inflammatory conditions.

7 Claims, 30 Drawing Sheets

OTHER PUBLICATIONS human granulocyte-macrophage colony-stimulating factor", *EMBO J.*, 8(12): 3667–3676 (1989).

Grynkiewicz et al., "A New Generation of $Ca^{2+}$ Indicators with Greatly Improved Fluorescence Properties", *J. Biol. Chem.*, 260(6): 3440–3450 (1985).

Lee et al., "Characterization of Two High Affinity Human Interleukin-8 Receptors", *J. Biol. Chem.*, 267: 16283–16287 (1992).

Hemmi et al., "A novel member of the interferon receptor family complements functionality of the murine intereron γ receptor in human cells", *Cell*, 76: 803–810 (1994).

Soh et al., "Identification and Sequence of an Accessory Factor Required for Activation of the Human Interferon γ Receptor", *Cell*, 76: 793–802 (1994).

Wolpe & Cerami, "Macrophage inflammatory proteins 1 and 2: members of a novel superfamily of cytokines", *FASEB J.*, 3: 2565–2573 (1989).

Chuntharapai et al., "Generation and characterization of monoclonal antibodies (mAbs) to human IL 8 receptor A", *J. Immunol.*, 152(8 Pt A), 126A, abstract #708 (May 21–25, 1993).

Hebert et al., "Endothelial and Leukocyte Forms of IL-8", *J. Immunol.*, 145(9): 3033–3040 (1990).

Horuk et al., "Purification, Receptor Binding Analysis and Biological Characterization of Human Melanoma Growth Stimulating Activity (MGSA)", *J. Biol. Chem.*, 268(1): 541–546 (1993).

Hebert et al., "Scanning Mutagenesis of Interleukin-8 Identifies a Cluster of Residues Required for Receptor Binding", *J. Biol. Chem.*, 266(28): 18989–18994 (1991).

Clark-Lewis et al., "Structure-Activity Relationships of Interleukin-8 Determined Using Chemically Synthesized Analogs", *J. Biol. Chem.*, 266(34): 23128–23134 (1991).

Boulay et al., "Synthesis and use of a novel N-formyl peptide derivative to isolate a human N-formyl peptide receptor cDNA", *Biochem. Biophys Res. Comm.*, 168(3): 1103–1109 (1990).

Gerard & Gerard, "The chemotactic receptor for human C5a anaphylatoxin", *Nature*, 349: 614–617 (1991).

Sims et al., "cDNA Expression Cloning of the Il-1 Receptor, a Member of the Immunoglobulin Superamily", *Science*, 241: 585–589 (1988).

D'Andrea et al., "Expression Cloning of the Murine Erythropoietin Receptor", *Cell*, 57: 277–285 (1989).

Dixon et al., "Structure-Function Analysis of the β-Adrenergic Receptor", *Cold Spring Harbor Sym. Quant. Biol.*, LIII: 487–497 (1988).

Ramachandran et al., "The Structural and Functional Interrelationships of Muscarinic Acetylcholine Receptor Subtypes", *Bioessays*, 10: 54–57 (1989).

Saragovi et al., "The Murine Interleukin 2 Receptor ", *J. Immunol.*, 138(6): 1918–1926 (1987).

Thomas et al., "Molecular Cloning of the fMet--Leu-Phe Receptor from Neutrophils", *J. Biol. Chem.*, 265(33): 20061–20064 (1990).

Beckmann et al., "Molecular Characterization of the Interleukin-8 Receptor", *Biochem. Biophys. Res. Comm.*, 179(2): 784–789 (1991).

Thomas et al., "The Interleukin-8 Receptor Is Encoded by a Neutrophil-specific cDNA clone, F3R", *J. Biol. Chem.*, 266(23): 14839–14841 (1991).

Smyth et al., "IL-8 Gene Expression and Production in Human Peripheral Blood Lymphocyte Subsets", *J. Immunol.*, 146(11): 3815–3823.

Mattoli et al., "Expression of the Potent Inflammatory Cytokines, GM-CSF, IL6, and IL8, in Bronchial Epithelial Cells of Asthmatic Patients", 101(3)(Supp.) 27S–29S (1992).

Koch et al., "Interleukin-8 is a potent human macrophage-derived mediator of angiogenesis that is blocked by interleukin-8 antibody and antisense oligonucleotide", *Arthritis Rheumato.*, 35(2 Supp): S49, abs. #86 (1992).

De Forge et al, "Interleukin-1 Receptor Antagonist Protein Inhibits Interleukin-8 Expression in Lipopolysaccharide-stimulated Human Whole Blood", *Amer. J. Path.*, 140(5): 104–1054 (1992).

Sticherling et al., "Production and Characterization of Monoclonal Antibodies Against the Novel Neutrophil Activating Peptide NAP/IL-8", *J. Immunol.*, 143(5): 1628–1634 (1989).

DeForge et al., "Oxygen Radical Scavengers Selectively Inhibit Interleukin 8 Production in Human Whole Blood", *J. Clin. Invest.*, 90(5): 2123–2129 (1992).

Vittori et al., "Protective effect of nedocomil sodium on the interleukin-1-induced production of interleukin-8 in human bronchial epithelial cells", *J. Allergy Clin. Immunol.*, 90(1): 76–84 (1992).

(List continued on next page.)

OTHER PUBLICATIONS

Seitz et al., "Interleukin-8 in inflammatory rheumtaic diseases: synovial fluid levels, relation to rheumatoid factors, production by mononuclear cells, and effects of gold sodium thiomalate and methotrexate", *Rheumatology*, 12: 159-164 (1992).

Deleuran et al., "The effect of second-line antirheumatic drugs on interleukin-8 mRNA synthesis and protein secretion in human endothelial cells", *Cytokine*, 4(5): 403-409 (1992).

Rampart et al., "Development and Application of a Radioimmunoassay for Interleukin-8: Detection of Interleukin-8 Synovial Fluids from Patients with Inflammatory Joint Disease", *Laboratory Invest.*, 66(4): 512-518 (1992).

Seitz et al., "Enhanced Production of Neutrophil-activting Peptide-1/Interleukin-8 in Rheumatoid Arthritis", *J. Clin. Invest.*, 87(2): 463-469 (1991).

Brennan et al., "Detection of interleukin 8 biological activity in synovial fluids from patients with rheumatoid arthritis and production of interluekin 8 mRNA by isolated synovial cells", *Eur. J. Immunol.*, 20: 2141-2144 (1990).

Mahida et al., "Enhanced synthesis of neutrophil-activating peptide-I/interleukin-8 in active ulcerative colitis", *Clinical Science*, 82: 273-275 (1992).

Peichl et al., "Human neutrophil activating peptide/interleukin 8 acts as an autoantigen in rheumatoid arthritis", *Annals Rheum. Dis.*, 51: 19-22 (1992).

Lindley et al., "NAP-1/IL-8 in Rheumatoid Arthritis", *Chemotactic Cytokines: Biology of the Inflammatory Peptide Supergene Family*, J. Westwick et al., eds., 147-156 (1991).

Koch et al., "Synovial tissue macrophage as a source of the chemotactic cytokine IL-8", *J. Immunol.*, 147(7): 2187-2195 (1991).

Moser et al., "Interleukin-8 Antagonists Genenrated by N-terminal Modification", *J. Biol. Chem.*, 268(10): 7125-7128 (1993).

Porat et al., "Interleukin-1 (IL-1) receptor blockade reduces endotoxin and *Borrelia burgdorferi*-stimulated IL-8 synthesis in human mononuclear cells", *FASEB J.*, 6(7): 2482-2486 (1992).

Gayle III et al., "Importance of the Amino Terminus of the Interleukin-8 Receptor in Ligand Interactions", *J. Biol. Chem.*, 268(10): 7283-7289 (1993).

Hirota et al., "Production of interleukin 8 by cultured synovial cells in response to interluekin 1 and tumor necrosis factor", *Rheumatol. Int.*, 12: 13-16 (1992).

Crockard et al., "Markers of Inflammatory Activation: Upregulation of Complements Receptors CR1 and CR3 on Synovial Fluid Neutrophils from Patients with Inflammatory Joint Disease", *Clin. Immunol. & Immunopath.*, 65(2): 135-142 (1992).

Dinarello et al., "Anticytokine Strategies in the Treatment of the Systemic Inflammatory Response Syndrome", *JAMA*, 269(14) 1829-1835 (1991).

Ye et al., "Inhibition of IL-8 binding to the type B IL-8 receptor by an anti-IL-8 receptor antibody", *FASEB J.*, 8: A136, Abstract 786 (1994).

Hammond et al., "Generation of neutralizing antibodies to human interleukin-8 (IL8) receptors", *J. Cell. Biochem.*, Suppl. 18B: 318, Abstract #0108 (1994).

```
Met Ser Asn Ile Thr Asp Pro Gln Met Trp Asp Phe Asp Leu
 1            5                   10                 15

Asn Phe Thr Gly Met Pro Pro Ala Asp Glu Asp Tyr Ser Pro Cys
               20              25                      30

Met Leu Glu Thr Glu Thr Leu Asn Lys Tyr Val Val Ile Ile Ala
               35              40                      45

Tyr Ala Leu Val Phe Leu Leu Ser Leu Leu Gly Asn Ser Leu Val
               50              55                      60

Met Leu Val Ile Leu Tyr Ser Arg Val Gly Arg Ser Val Thr Asp
               65              70                      75

Val Tyr Leu Leu Asn Leu Ala Leu Ala Asp Leu Leu Phe Ala Leu
               80              85                      90

Thr Leu Pro Ile Trp Ala Ala Ser Lys Val Asn Gly Trp Ile Phe
               95             100                     105

Gly Thr Phe Leu Cys Lys Val Val Ser Leu Leu Lys Glu Val Asn
              110             115                     120

Phe Tyr Ser Gly Ile Leu Leu Leu Ala Cys Ile Ser Val Asp Arg
              125             130                     135

Tyr Leu Ala Ile Val His Ala Thr Arg Thr Leu Thr Gln Lys Arg
              140             145                     150

His Leu Val Lys Phe Val Cys Leu Gly Cys Trp Gly Leu Ser Met
              155             160                     165

Asn Leu Ser Leu Pro Phe Phe Leu Phe Arg Gln Ala Tyr His Pro
              170             175                     180

Asn Asn Ser Ser Pro Val Cys Tyr Glu Val Leu Gly Asn Asp Thr
              185             190                     195

Ala Lys Trp Arg Met Val Leu Arg Ile Leu Pro His Thr Phe Gly
              200             205                     210

Phe Ile Val Pro Leu Phe Val Met Leu Phe Cys Tyr Gly Phe Thr
              215             220                     225

Leu Arg Thr Leu Phe Lys Ala His Met Gly Gln Lys His Arg Ala
              230             235                     240

Met Arg Val Ile Phe Ala Val Val Leu Ile Phe Leu Leu Cys Trp
              245             250                     255
```

FIG.2A

```
Leu Pro Tyr Asn Leu Val Leu Leu Ala Asp Thr Leu Met Arg Thr
            260                 265                 270

Gln Val Ile Gln Glu Thr Cys Glu Arg Arg Asn Asn Ile Gly Arg
            275                 280                 285

Ala Leu Asp Ala Thr Glu Ile Leu Gly Phe Leu His Ser Cys Leu
            290                 295                 300

Asn Pro Ile Ile Tyr Ala Phe Ile Gly Gln Asn Phe Arg His Gly
            305                 310                 315

Phe Leu Lys Ile Leu Ala Met His Gly Leu Val Ser Lys Glu Phe
            320                 325                 330

Leu Ala Arg His Arg Val Thr Ser Tyr Thr Ser Ser Ser Val Asn
            335                 340                 345

Val Ser Ser Asn Leu
            350
```

FIG.2B

ATGTCAAATA TTACAGATCC ACAGATGTGG GATTTTGATG ATCTAAATTT 50

CACTGGCATG CCACCTGCAG ATGAAGATTA CAGCCCCTGT ATGCTAGAAA 100

CTGAGACACT CAACAAGTAT GTTGTGATCA TCGCCTATGC CCTAGTGTTC 150

CTGCTGAGCC TGCTGGGAAA CTCCCTGGTG ATGCTGGTCA TCTTATACAG 200

CAGGGTCGGC CGCTCCGTCA CTGATGTCTA CCTGCTGAAC CTGGCCTTGG 250

CCGACCTACT CTTTGCCCTG ACCTTGCCCA TCTGGGCCGC CTCCAAGGTG 300

AATGGCTGGA TTTTGGCAC ATTCCTGTGC AAGGTGGTCT CACTCCTGAA 350

GGAAGTCAAC TTCTACAGTG GCATCCTGCT GTTGGCCTGC ATCAGTGTGG 400

ACCGTTACCT GGCCATTGTC CATGCCACAC GCACACTGAC CCAGAAGCGT 450

CACTTGGTCA AGTTTGTTTG TCTTGGCTGC TGGGGACTGT CTATGAATCT 500

GTCCCTGCCC TTCTTCCTTT TCCGCCAGGC TTACCATCCA AACAATTCCA 550

GTCCAGTTTG CTATGAGGTC CTGGGAAATG ACACAGCAAA ATGGCGGATG 600

GTGTTGCGGA TCCTGCCTCA CACCTTTGGC TTCATCGTGC CGCTGTTTGT 650

CATGCTGTTC TGCTATGGAT TCACCCTGCG TACACTGTTT AAGGCCCACA 700

TGGGGCAGAA GCACCGAGCC ATGAGGGTCA TCTTTGCTGT CGTCCTCATC 750

TTCCTGCTTT GCTGGCTGCC CTACAACCTG GTCCTGCTGG CAGACACCCT 800

CATGAGGACC CAGGTGATCC AGGAGACCTG TGAGCGCCGC AACAACATCG 850

GCCGGGCCCT GGATGCCACT GAGATTCTGG GATTTCTCCA TAGCTGCCTC 900

FIG.2C

```
AACCCCATCA TCTACGCCTT CATCGGCCAA AATTTTCGCC ATGGATTCCT 950

CAAGATCCTG GCTATGCATG GCCTGGTCAG CAAGGAGTTC TTGGCACGTC 1000

ATCGTGTTAC CTCCTACACT TCTTCGTCTG TCAATGTCTC TTCCAACCTC 1050

TGAAAACCAT CGATGAAGGA ATATCTCTTC TCAGAAGGAA AGAATAACCA 1100

ACACCCTGAG GTTGTGTGTG GAAGGTGATC TGGCTCTGGA CAGGCACTAT 1150

CTGGGTTTTG GGGGACGCT ATAGGATGTG GGAAGTTAG GAACTGGTGT 1200

CTTCAGGGGC CACACCAACC TTCTGAGGAG CTGTTGAGGT ACCTCCAAGG 1250

ACCGGCCTTT GCACCTCCAT GGAAACGAAG CACCATCATT CCCGTTGAAC 1300

GTCACATCTT TAACCCACTA ACTGGCTAAT TAGCATGGCC ACATCTGAGC 1350

CCCGAATCTG ACATTAGATG AGAGAACAGG GCTGAAGCTG TGTCCTCATG 1400

AGGGCTGGAT GCTCTCGTTG ACCCTCACAG GAGCATCTCC TCAACTCTGA 1450

GTGTTAAGCG TTGAGCCACC AAGCTGGTGG CTCTGTGTGC TCTGATCCGA 1500

GCTCAGGGGG GTGGTTTTCC CATCTCAGGT GTGTTGCAGT GTCTGCTGGA 1550

GACATTGAGG CAGGCACTGC CAAAACATCA ACCTGCCAGC TGGCCTTGTG 1600

AGGAGCTGGA AACACATGTT CCCCTTGGGG GTGGTGGATG AACAAAGAGA 1650

AAGAGGGTTT GGAAGCCAGA TCTATGCCAC AAGAACCCCC TTTACCCCCA 1700
```

FIG.2D

```
TGACCAACAT CGCAGACACA TGTGCTGGCC ACCTGCTGAG CCCCAAGTGG 1750

AACGAGACAA GCAGCCCTTA GCCCTTCCCC TCTGCAGCTT CCAGGCTGGC 1800

GTGCAGCATC AGCATCCCTA GAAAGCCATG TGCAGCCACC AGTCCATTGG 1850

GCAGGCAGAT GTTCCTAATA AAGCTTCTGT TCC 1883
```

FIG.2E

```
Met Glu Gly Ile Ser Ile Tyr Thr Ser Asp Asn Tyr Thr Glu Glu
 1               5                  10                  15
Met Gly Ser Gly Asp Tyr Asp Ser Met Lys Glu Pro Cys Phe Arg
                 20                  25                  30
Glu Glu Asn Ala Asn Phe Asn Lys Ile Phe Leu Pro Thr Ile Tyr
                 35                  40                  45
Ser Ile Ile Phe Leu Thr Gly Ile Val Gly Asn Gly Leu Val Ile
                 50                  55                  60
Leu Val Met Gly Tyr Gln Lys Lys Leu Arg Ser Met Thr Asp Lys
                 65                  70                  75
Tyr Arg Leu His Leu Ser Val Ala Asp Leu Leu Phe Val Ile Thr
                 80                  85                  90
Leu Pro Phe Trp Ala Val Asp Ala Val Ala Asn Trp Tyr Phe Gly
                 95                 100                 105
Asn Phe Leu Cys Lys Ala Val His Val Ile Tyr Thr Val Asn Leu
                110                 115                 120
Tyr Ser Ser Val Leu Ile Leu Ala Phe Ile Ser Leu Asp Arg Tyr
                125                 130                 135
Leu Ala Ile Val His Ala Thr Asn Ser Gln Arg Pro Arg Lys Leu
                140                 145                 150
Leu Ala Glu Lys Val Val Tyr Val Gly Val Trp Ile Pro Ala Leu
                155                 160                 165
Leu Leu Thr Ile Pro Asp Phe Ile Phe Ala Asn Val Ser Glu Ala
                170                 175                 180
Asp Asp Arg Tyr Ile Cys Asp Arg Phe Tyr Pro Asn Asp Leu Trp
                185                 190                 195
Val Val Val Phe Gln Phe Gln His Ile Met Val Gly Leu Ile Leu
                200                 205                 210
Pro Gly Ile Val Ile Leu Ser Cys Tyr Cys Ile Ile Ile Ser Lys
                215                 220                 225
Leu Ser His Ser Lys Gly His Gln Lys Arg Lys Ala Leu Lys Thr
                230                 235                 240
Thr Val Ile Leu Ile Leu Ala Phe Phe Ala Cys Trp Leu Pro Tyr
                245                 250                 255
```

FIG.4A

Tyr Ile Gly Ile Ser Ile Asp Ser Phe Ile Leu Leu Glu Ile Ile
                    260             265                 270

Lys Gln Gly Cys Glu Phe Glu Asn Thr Val His Lys Trp Ile Ser
                    275             280                 285

Ile Thr Glu Ala Leu Ala Phe Phe His Cys Cys Leu Asn Pro Ile
                    290             295                 300

Leu Tyr Ala Phe Leu Gly Ala Lys Phe Lys Thr Ser Ala Gln His
                    305             310                 315

Ala Leu Thr Ser Val Ser Arg Gly Ser Ser Leu Lys Ile Leu Ser
                    320             325                 330

Lys Gly Lys Arg Gly Gly His Ser Ser Val Ser Thr Glu Ser Glu
                    335             340                 345

Ser Ser Ser Phe His Ser Ser
                    350     352

FIG.4B

```
GAATTCCAGT GTGCTGGCGG CGCGGCGCAA AGTGACGCCG AGGGCCTGAG  50

TGCTCCAGTA GCCACCGCAT CTGGAGAACC AGCGGTTACC ATGGAGGGGA 100

TCAGTATATA CACTTCAGAT AACTACACCG AGGAAATGGG CTCAGGGGAC 150

TATGACTCCA TGAAGGAACC CTGTTTCCGT GAAGAAAATG CTAATTTCAA 200

TAAAATCTTC CTGCCCACCA TCTACTCCAT CATCTTCTTA ACTGGCATTG 250

TGGGCAATGG ATTGGTCATC CTGGTCATGG GTTACCAGAA GAAACTGAGA 300

AGCATGACGG ACAAGTACAG GCTGCACCTG TCAGTGGCCG ACCTCCTCTT 350

TGTCATCACG CTTCCCTTCT GGGCAGTTGA TGCCGTGGCA AACTGGTACT 400

TTGGGAACTT CCTATGCAAG GCAGTCCATG TCATCTACAC AGTCAACCTC 450

TACAGCAGTG TCCTCATCCT GGCCTTCATC AGTCTGGACC GCTACCTGGC 500

CATCGTCCAC GCCACCAACA GTCAGAGGCC AAGGAAGCTG TTGGCTGAAA 550

AGGTGGTCTA TGTTGGCGTC TGGATCCCTG CCCTCCTGCT GACTATTCCC 600

GACTTCATCT TTGCCAACGT CAGTGAGGCA GATGACAGAT ATATCTGTGA 650

CCGCTTCTAC CCCAATGACT TGTGGGTGGT TGTGTTCCAG TTTCAGCACA 700

TCATGGTTGG CCTTATCCTG CCTGGTATTG TCATCCTGTC CTGCTATTGC 750

ATTATCATCT CCAAGCTGTC ACACTCCAAG GGCCACCAGA AGCGCAAGGC 800

CCTCAAGACC ACAGTCATCC TCATCCTGGC TTTCTTCGCC TGTTGGCTGC 850

CTTACTACAT TGGGATCAGC ATCGACTCCT TCATCCTCCT GGAAATCATC 900
```

FIG.4C

```
AAGCAAGGGT GTGAGTTTGA GAACACTGTG CACAAGTGGA TTTCCATCAC  950

CGAGGCCCTA GCTTTCTTCC ACTGTTGTCT GAACCCCATC CTCTATGCTT 1000

TCCTTGGAGC CAAATTTAAA ACCTCTGCCC AGCACGCACT CACCTCTGTG 1050

AGCAGAGGGT CCAGCCTCAA GATCCTCTCC AAAGGAAAGC GAGGTGGACA 1100

TTCATCTGTT TCCACTGAGT CTGAGTCTTC AAGTTTTCAC TCCAGCTAAC 1150

ACAGATGTAA AAGACTTTTT TTTATACGAT AAATAACTTT TTTTTAAGTT 1200

ACACATTTTT CAGATATAAA AGACTGACCA ATATTGTACA GTTTTTATTG 1250

CTTGTTGGAT TTTTGTCTTG TGTTTCTTTA GTTTTTGTGA AGTTTAATTG 1300

ACTTATTTAT ATAAATTTTT TTTGTTTCAT ATTGATGTGT GTCTAGGCAG 1350

GACCTGTGGC CAAGTTCTTA GTTGCTGTAT GTCTCGTGGT AGGACTGTAG 1400

AAAAGGGAAC TGAACATTCC AGAGCGTGTA GTGAATCACG TAAAGCTAGA 1450

AATGATCCCC AGCTGTTTAT GCATAGATAA TCTCTCCATT CCCGTGGAAC 1500

GTTTTTCCTG TTCTTAAGAC GTGATTTTGC TGTAGAAGAT GGCACTTATA 1550

ACCAAAGCCC AAAGTGGTAT AGAAATGCTG GTTTTTCAGT TTTCAGGAGT 1600

GGGTTGATTT CAGCACCTAC AGTGTACAGT CTTGTATTAA GTTGTTAATA 1650

AAAGTACATG TTAAACTTAA AAAAAAAAAA AAAAAAAAAA AAAAAAAAA  1700

AAAAAAAAAA AAAGCGGCCG CCAGCACACT GGAATTC 1737
```

FIG. 4D

```
Met Asn Tyr Pro Leu Thr Leu Glu Met Asp Leu Glu Asn Leu Glu
 1               5                  10                  15

Asp Leu Phe Trp Glu Leu Asp Arg Leu Asp Asn Tyr Asn Asp Thr
                 20                  25                  30

Ser Leu Val Glu Asn His Leu Cys Pro Ala Thr Glu Gly Pro Leu
                 35                  40                  45

Met Ala Ser Phe Lys Ala Val Phe Val Pro Val Ala Tyr Ser Leu
                 50                  55                  60

Ile Phe Leu Leu Gly Val Ile Gly Asn Val Leu Val Leu Val Ile
                 65                  70                  75

Leu Glu Arg His Arg Gln Thr Arg Ser Ser Thr Glu Thr Phe Leu
                 80                  85                  90

Phe His Leu Ala Val Ala Asp Leu Leu Leu Val Phe Ile Leu Pro
                 95                 100                 105

Phe Ala Val Ala Glu Gly Ser Val Gly Trp Val Leu Gly Thr Phe
                110                 115                 120

Leu Cys Lys Thr Val Ile Ala Leu His Lys Val Asn Phe Tyr Cys
                125                 130                 135

Ser Ser Leu Leu Leu Ala Cys Ile Ala Val Asp Arg Tyr Leu Ala
                140                 145                 150

Ile Val His Ala Val His Ala Tyr Arg His Arg Arg Leu Leu Ser
                155                 160                 165

Ile His Ile Thr Cys Gly Thr Ile Trp Leu Val Gly Phe Leu Leu
                170                 175                 180

Ala Leu Pro Glu Ile Leu Phe Ala Lys Val Ser Gln Gly His His
                185                 190                 195

Asn Asn Ser Leu Pro Arg Cys Thr Phe Ser Gln Glu Asn Gln Ala
                200                 205                 210

Glu Thr His Ala Trp Phe Thr Ser Arg Phe Leu Tyr His Val Ala
                215                 220                 225

Gly Phe Leu Leu Pro Met Leu Val Met Gly Trp Cys Tyr Val Gly
                230                 235                 240

Val Val His Arg Leu Arg Gln Ala Gln Arg Arg Pro Gln Arg Gln
                245                 250                 255
```

FIG.5A

```
Lys Ala Val Arg Val Ala Ile Leu Val Thr Ser Ile Phe Phe Leu
                260             265             270

Cys Trp Ser Pro Tyr His Ile Val Ile Phe Leu Asp Thr Leu Ala
                275             280             285

Arg Leu Lys Ala Val Asp Asn Thr Cys Lys Leu Asn Gly Ser Leu
                290             295             300

Pro Val Ala Ile Thr Met Cys Glu Phe Leu Gly Leu Ala His Cys
                305             310             315

Cys Leu Asn Pro Met Leu Tyr Thr Phe Ala Gly Val Lys Phe Arg
                320             325             330

Ser Asp Leu Ser Arg Leu Leu Thr Lys Leu Gly Cys Thr Gly Pro
                335             340             345

Ala Ser Leu Cys Gln Leu Phe Pro Ser Trp Arg Arg Ser Ser Leu
                350             355             360

Ser Glu Ser Glu Asn Ala Thr Ser Leu Thr Thr Phe
                365             370     372
```

FIG.5B

```
GAATTCCAGT GTGCTGGCGG CCGCCCAGTG TGCTGGCGGC GGCAGTTGAG  50

GGAAAGGACA GAGGTTATGA GTGCCTGCAA GAGTGGCAGC CTGGAGTAGA 100

GAAAACACTA AGGTGGAGT  CAAAAGACCT GAGTTCAAGT CCCAGCTCTG 150

CCACTGGTTA GCTGTGGGAT CTCGGAAAAG ACCCAGTGAA AAAAAAAAA  200

AAAGTGATGA GTTGTGAGGC AGGTCGCGGC CCTACTGCCT CAGGAGACGA 250

TGCGCAGCTC ATTTGCTTAA ATTTGCAGCT GACGGCTGCC ACCTCTCTAG 300

AGGCACCTGG CGGGGAGCCT CTCAACATAA GACAGTGACC AGTCTGGTGA 350

CTCACAGCCG GCACAGCCAT GAACTACCCG CTAACGCTGG AAATGGACCT 400

CGAGAACCTG GAGGACCTGT TCTGGGAACT GGACAGATTG GACAACTATA 450

ACGACACCTC CCTGGTGGAA AATCATCTCT GCCCTGCCAC AGAGGGGCCC 500

CTCATGGCCT CCTTCAAGGC CGTGTTCGTG CCCGTGGCCT ACAGCCTCAT 550

CTTCCTCCTG GGCGTGATCG GCAACGTCCT GGTGCTGGTG ATCCTGGAGC 600

GGCACCGGCA GACACGCAGT TCCACGGAGA CCTTCCTGTT CCACCTGGCC 650

GTGGCCGACC TCCTGCTGGT CTTCATCTTG CCCTTTGCCG TGGCCGAGGG 700

CTCTGTGGGC TGGGTCCTGG GGACCTTCCT CTGCAAAACT GTGATTGCCC 750

TGCACAAAGT CAACTTCTAC TGCAGCAGCC TGCTCCTGGC CTGCATCGCC 800

GTGGACCGCT ACCTGGCCAT TGTCCACGCC GTCCATGCCT ACCGCCACCG 850

CCGCCTCCTC TCCATCCACA TCACCTGTGG GACCATCTGG CTGGTGGGCT 900
```

FIG.5C

```
TCCTCCTTGC CTTGCCAGAG ATTCTCTTCG CCAAAGTCAG CCAAGGCCAT 950

CACAACAACT CCCTGCCACG TTGCACCTTC TCCCAAGAGA ACCAAGCAGA 1000

AACGCATGCC TGGTTCACCT CCCGATTCCT CTACCATGTG GCGGGATTCC 1050

TGCTGCCCAT GCTGGTGATG GGCTGGTGCT ACGTGGGGGT AGTGCACAGG 1100

TTGCGCCAGG CCCAGCGGCG CCCTCAGCGG CAGAAGGCAG TCAGGGTGGC 1150

CATCCTGGTG ACAAGCATCT TCTTCCTCTG CTGGTCACCC TACCACATCG 1200

TCATCTTCCT GGACACCCTG GCGAGGCTGA AGGCCGTGGA CAATACCTGC 1250

AAGCTGAATG GCTCTCTCCC CGTGGCCATC ACCATGTGTG AGTTCCTGGG 1300

CCTGGCCCAC TGCTGCCTCA ACCCCATGCT CTACACTTTC GCCGGCGTGA 1350

AGTTCCGCAG TGACCTGTCG CGGCTCCTGA CGAAGCTGGG CTGTACCGGC 1400

CCTGCCTCCC TGTGCCAGCT CTTCCCTAGC TGGCGCAGGA GCAGTCTCTC 1450

TGAGTCAGAG AATGCCACCT CTCTCACCAC GTTCTAGGTC CCAGTGTCCC 1500

CTTTTATTGC TGCTTTTCCT TGGGGCAGGC AGTGATGCTG GATGCTCCTT 1550

CCAACAGGAG CTGGGATCCT AAGGGCTCAC CGTGGCTAAG AGTGTCCTAG 1600

GAGTATCCTC ATTTGGGGTA GCTAGAGGAA CCAACCCCCA TTTCTAGAAC 1650

ATCCCGCGGC CGCCAGCACA CTGGAATTC 1679
```

FIG.5D

```
Met Glu Asp Phe Asn Met Glu Ser Asp Ser Phe Glu Asp Phe Trp
 1               5                  10                  15

Lys Gly Glu Asp Leu Ser Asn Tyr Ser Tyr Ser Ser Thr Leu Pro
                 20                  25                  30

Pro Phe Leu Leu Asp Ala Ala Pro Cys Glu Pro Glu Ser Leu Glu
                 35                  40                  45

Ile Asn Lys Tyr Phe Val Val Ile Ile Tyr Ala Leu Val Phe Leu
                 50                  55                  60

Leu Ser Leu Leu Gly Asn Ser Leu Val Met Leu Val Ile Leu Tyr
                 65                  70                  75

Ser Arg Val Gly Arg Ser Val Thr Asp Val Tyr Leu Leu Asn Leu
                 80                  85                  90

Ala Leu Ala Asp Leu Leu Phe Ala Leu Thr Leu Pro Ile Trp Ala
                 95                 100                 105

Ala Ser Lys Val Asn Gly Trp Ile Phe Gly Thr Phe Leu Cys Lys
                110                 115                 120

Val Val Ser Leu Leu Lys Glu Val Asn Phe Tyr Ser Gly Ile Leu
                125                 130                 135

Leu Leu Ala Cys Ile Ser Val Asp Arg Tyr Leu Ala Ile Val His
                140                 145                 150

Ala Thr Arg Thr Leu Thr Gln Lys Arg Tyr Leu Val Lys Phe Ile
                155                 160                 165

Cys Leu Ser Ile Trp Gly Leu Ser Leu Leu Ala Leu Pro Val
                170                 175                 180

Leu Leu Phe Arg Arg Thr Val Tyr Ser Ser Asn Val Ser Pro Ala
                185                 190                 195

Cys Tyr Glu Asp Met Gly Asn Asn Thr Ala Asn Trp Arg Met Leu
                200                 205                 210

Leu Arg Ile Leu Pro Gln Ser Phe Gly Phe Ile Val Pro Leu Leu
                215                 220                 225

Ile Met Leu Phe Cys Tyr Gly Phe Thr Leu Arg Thr Leu Phe Lys
                230                 235                 240

Ala His Met Gly Gln Lys His Arg Ala Met Arg Val Ile Phe Ala
                245                 250                 255

Val Val Leu Ile Phe Leu Leu Cys Trp Leu Pro Tyr Asn Leu Val
                260                 265                 270
```

FIG.6A

```
Leu Leu Ala Asp Thr Leu Met Arg Thr Gln Val Ile Gln Glu Thr
            275             280             285

Cys Glu Arg Arg Asn His Ile Asp Arg Ala Leu Asp Ala Thr Glu
            290             295             300

Ile Leu Gly Ile Leu His Ser Cys Leu Asn Pro Leu Ile Tyr Ala
            305             310             315

Phe Ile Gly Gln Lys Phe Arg His Gly Leu Leu Lys Ile Leu Ala
            320             325             330

Ile His Gly Leu Ile Ser Lys Asp Ser Leu Pro Lys Asp Ser Arg
            335             340             345

Pro Ser Phe Val Gly Ser Ser Ser Gly His Thr Ser Thr Thr Leu
            350             355             360
```

FIG.6B

CTACAGGTGA AAAGCCCAGC GACCCAGTCA GGATTTAAGT TTACCTCAAA 50

AATGGAAGAT TTTAACATGG AGAGTGACAG CTTTGAAGAT TTCTGGAAAG 100

GTGAAGATCT TAGTAATTAC AGTTACAGCT CTACCCTGCC CCCTTTTCTA 150

CTAGATGCCG CCCCATGTGA ACCAGAATCC CTGGAAATCA ACAAGTATTT 200

TGTGGTCATT ATCTATGCCC TGGTATTCCT GCTGAGCCTG CTGGGAAACT 250

CCCTCGTGAT GCTGGTCATC TTATACAGCA GGGTCGGCCG CTCCGTCACT 300

GATGTCTACC TGCTGAACCT AGCCTTGGCC GACCTACTCT TTGCCCTGAC 350

CTTGCCCATC TGGGCCGCCT CCAAGGTGAA TGGCTGGATT TTTGGCACAT 400

TCCTGTGCAA GGTGGTCTCA CTCCTGAAGG AAGTCAACTT CTATAGTGGC 450

ATCCTGCTAC TGGCCTGCAT CAGTGTGGAC CGTTACCTGG CCATTGTCCA 500

TGCCACACGC ACACTGACCC AGAAGCGCTA CTTGGTCAAA TTCATATGTC 550

TCAGCATCTG GGGTCTGTCC TTGCTCCTGG CCCTGCCTGT CTTACTTTTC 600

CGAAGGACCG TCTACTCATC CAATGTTAGC CCAGCCTGCT ATGAGGACAT 650

GGGCAACAAT ACAGCAAACT GGCGGATGCT GTTACGGATC CTGCCCCAGT 700

CCTTTGGCTT CATCGTGCCA CTGCTGATCA TGCTGTTCTG CTACGGATTC 750

ACCCTGCGTA CGCTGTTTAA GGCCCACATG GGGCAGAAGC ACCGGGCCAT 800

GCGGGTCATC TTTGCTGTCG TCCTCATCTT CCTGCTTTGC TGGCTGCCCT 850

ACAACCTGGT CCTGCTGGCA GACACCCTCA TGAGGACCCA GGTGATCCAG 900

FIG.6C

```
GAGACCTGTG AGCGCCGCAA TCACATCGAC CGGGCTCTGG ATGCCACCGA 950

GATTCTGGGC ATCCTTCACA GCTGCCTCAA CCCCCTCATC TACGCCTTCA 1000

TTGGCCAGAA GTTTCGCCAT GGACTCCTCA AGATTCTAGC TATACATGGC 1050

TTGATCAGCA AGGACTCCCT GCCCAAAGAC AGCAGGCCTT CCTTTGTTGG 1100

CTCTTCTTCA GGGCACACTT CCACTACTCT CTAAGACCTC CTGCCTAAGT 1150

GCAGCCCCGT GGGGTTCCTC CCTTCTCTTC ACAGTCACAT TCCAAGCCTC 1200

ATGTCCACTG GTTCTTCTTG GTCTCAGTGT CAATGCAGCC CCCATTGTGG 1250

TCACAGGAAG CAGAGGAGGC CACGTTCTTA CTAGTTTCCC TTGCATGGTT 1300

TAGAAAGCTT GCCCTGGTGC CTCACCCCTT GCCATAATTA CTATGTCATT 1350

TGCTGGAGCT CTGCCCATCC TGCCCCTGAG CCCATGGCAC TCTATGTTCT 1400

AAGAAGTGAA AATCTACACT CCAGTGAGAC AGCTCTGCAT ACTCATTAGG 1450

ATGGCTAGTA TCAAAAGAAA GAAAATCAGG CTGGCCAACG GGATGAAACC 1500

CTGTCTCTAC TAAAAATACA AAAAAAAAA AAAAAATTAG CCGGGCGTGG 1550

TGGTGAGTGC CTGTAATCAC AGCTACTTGG GAGGCTGAGA TGGGAGAATC 1600

ACTTGAACCC GGGAGGCAGA GGTTGCAGTG AGCCGAGATT GTGCCCCTGC 1650

ACTCCAGCCT GAGCGACAGT GAGACTCTGT CTCAGTCCAT GAAGATGTAG 1700

AGGAGAAACT GGAACTCTCG AGCGTTGCTG GGGGGATTG TAAAATGG 1748
```

FIG.6D

ANTIBODIES TO HUMAN IL-8 TYPE B RECEPTOR

This application is a continuation-in-part application of U.S. Ser. No. 07/677,211 filed March 29, 1991, now abandoned.

BACKGROUND OF THE INVENTION

1. Field of the Invention

This invention relates to the field of assaying chemokine receptors and the preparation of agonists and antagonists to chemokines, in particular, antibodies to these chemokine receptors.

2. Description of Background and Related Art

While interleukin-8 was initially identified as a chemoattractant for neutrophils, and was known to bind a receptor on neutrophils (Samanta et al., *J. Exp. Med.*, 169: 1185–1189 (1989); Besemer et al., *J. Biol. Chem.*, 264: 17409–17415 (1989); Grob et al. *J. Biol. Chem.*, 265: 8311–8316 (1990)), it has in addition a wide range of pro-inflammatory activities including the stimulation of degranulation and the upregulation of the cell adhesion molecule MAC-1 and of the complement receptor CR1. Oppenheim et al., *Annu. Rev, Immunol.*, 9: 617–648 (1991).

IL-8 is secreted by many cell types in response to pro-inflammatory stimuli such as IL-1β, TNF, and endotoxin, and is a member of a family of pro-inflammatory cytokines with a variety of biological properties including selective leukocyte chemotaxis and activation. These cytokines form a superfamily, originally referred to as the platelet factor 4 superfamily (PF4A), and now referred to as the chemokine superfamily, that has been divided into two classes based on whether the first two conserved cysteine residues are separated by an intervening amino acid (C-X-C), or whether they are adjacent (C-C). The C-X-C class members include, for example, melanocyte growth stimulating factor (MGSA), platelet factor 4, and IL-8, while the C-C class includes RANTES (Regulated on Activation, Normal T Expressed and Secreted) and monocyte chemotactic peptide-1 (MCP-1).

The IL-8 receptors are members of the superfamily of seven transmembrane, G-protein linked receptors. Taylor, *Biochem. J.*, 272: 1 (1990). This family of receptors includes several hundred different receptors among which are the β-adrenergic receptor (Strader et al., *FASEB*, 3: 1825 (1989); Dixon et al., *EMBO J.*, 6: 3269 (1987)), the muscarinic and cholinergic receptors (Kubo et al., *Nature*, 323: 411 (1986); Peralta et al., *EMBO J.*, 6: 3923 (1987)), the C5a and fMet-Leu-Phe receptors. Two types of IL-8 receptors have been described: type A (IL8R-A) (Holmes et al., *Science*, 253: 1278 (1991)) and type B (IL8R-B) (Murphy and Tiffany, *Science*, 253: 1280 (1991)) receptors. These two types of receptors share 77% amino acid identity and have 29–34% sequence homology to C5a and fMet-Leu-Phe. Holmes et al., supra. IL8R-A has a high affinity (2 nM) for IL-8 only, while IL8R-B has a high affinity (2 nM) for both IL-8 and MGSA. The cell function and expression level of each receptor has yet to be determined.

It is an object of this invention to identify and prepare antibodies to the IL-8 type B receptor.

An additional object is to provide a method for treating or preventing an inflammatory response in a mammal using an antibody to such receptor.

These and other objects of this invention will be apparent from the specification as a whole.

SUMMARY OF THE INVENTION

In one aspect, the invention provides an anti-IL8R-BH antibody.

In another aspect, the invention provides a composition comprising the anti-IL8R-BH antibody and a pharmaceutically acceptable carrier, as well as a method for treating an inflammatory disorder comprising administering to a mammal in need of such treatment an effective amount of this composition.

BRIEF DESCRIPTION OF THE DRAWINGS

FIG. 1a depicts the binding of $^{125}$I-labeled IL-8 in competition with unlabelled IL-8 or fMLP. FIG. 1b depicts a Scatchard analysis of the IL-8 competition data which shows an apparent Kd=3.6 nM with an average of 820,000 binding sites/cell. Similar competitions with human neutrophils produced a Kd=1.1 nM with 31,000 binding sites/cell.

FIGS. 2a–2e depicts the amino acid (FIGS. 2a–2b) (SEQ ID NO. 1) and nucleotide (FIGS. 2c–2e) (SEQ ID NO. 2) sequences of the IL-8 receptor A cDNA insert from clone pRK5B.il8r1.1. The seven putative transmembrane domains are shown. There are 4 extracellular segments and 4 intracellular segments, each being separated by one of the transmembrane domains. The extracellular segments are approximately delineated by residues 1–39, 99–111, 134–154, 175–203 and 265–290. The IL-8 receptor contains 2 potential N-linked glycosylation sites in the first extracellular region and 3 more in the third extracellular loop.

FIGS. 4a–4d depicts the DNA (FIGS. 4c–4d) (SEQ ID NO. 4) and imputed polypeptide (FIGS. 4a–4b) (SEQ ID NO. 3) sequences for an additional chemokine superfamily receptor identified by probing lambda libraries of genomic DNA from a human monocyte-like cell line (L-60) and human peripheral blood lymphocytes (PBLs) using a large fragment of the IL-8 type A receptor DNA.

FIGS. 5a–5d depicts the DNA (FIGS. 5c–5d) (SEQ ID NO. 6) and imputed polypeptide (FIGS. 5a–5b) (SEQ ID NO. 5) sequences for yet another chemokine superfamily receptor identified by probing lambda libraries of genomic DNA from a human monocyte-like cell line (HL-60) and human peripheral blood lymphocytes (PBLs) using a large fragment of the IL-8 type A receptor DNA.

FIGS. 6a–6d depicts the amino acid (FIGS. 6a–6b) (SEQ ID NO. 7) and nucleotide (FIGS. 6c–6d) (SEQ ID NO. 8) sequences of the IL-8 receptor B cDNA insert from clone pRK5.8rr.27-1.1 as described by Lee et al., *J. Biol. Chem.*, 267: 16283–16287 (1992) and Murphy and Tiffany, *Science*, 253: 1280 (1991).

In FIG. 10a the solid bars are peptide 2-19, the diagonal hatched bars to the right of the solid bars are peptide 12-31, the dark crosshatching to the right of peptide 12-31 is peptide 99-110, the diagonal hatching to the right of peptide 99-110 is peptide 176-187, the open bars to the right of peptide 176-187 are peptide 187-203, the dotted bars to the right of peptide 187-203 are peptide 264-276, and the horizontal striped bars to the right of peptide 264-276 are peptide 276-290. In FIG. 10a, all peptides correspond to IL8R-A amino acid sequences. In FIG. 10b, the solid bars are peptide 2-19, the open bars to the right of peptide 2-19 are peptide 1-14, the dotted bars to the right of peptide 1-14 are peptide 1-11, and the diagonal hatching to the right of peptide 1-11 is peptide 1-13 (IL8R-B). In FIG. 10b, all peptides correspond to IL8R-A amino acid sequences except peptide 1-13, which corresponds to the first 13 amino acids at the N-terminus of IL8R-B.

In FIG. 15 the light cross-hatching is peptide 12-31 (IL8R-A), the dark cross-hatched columns to the right of the light cross-hatched columns are peptide 1-18 (IL8R-B), the solid columns to the right of peptide 1-18 are peptide 99-110 (IL8R-B), the diagonal hatching to the right of peptide 99-110 is peptide 265-277 (IL8R-B), and the open columns to the right of peptide 265-277 are peptide 277-291 (IL8R-A).

DETAILED DESCRIPTION OF THE INVENTION

I. Definitions

Figure 1A:
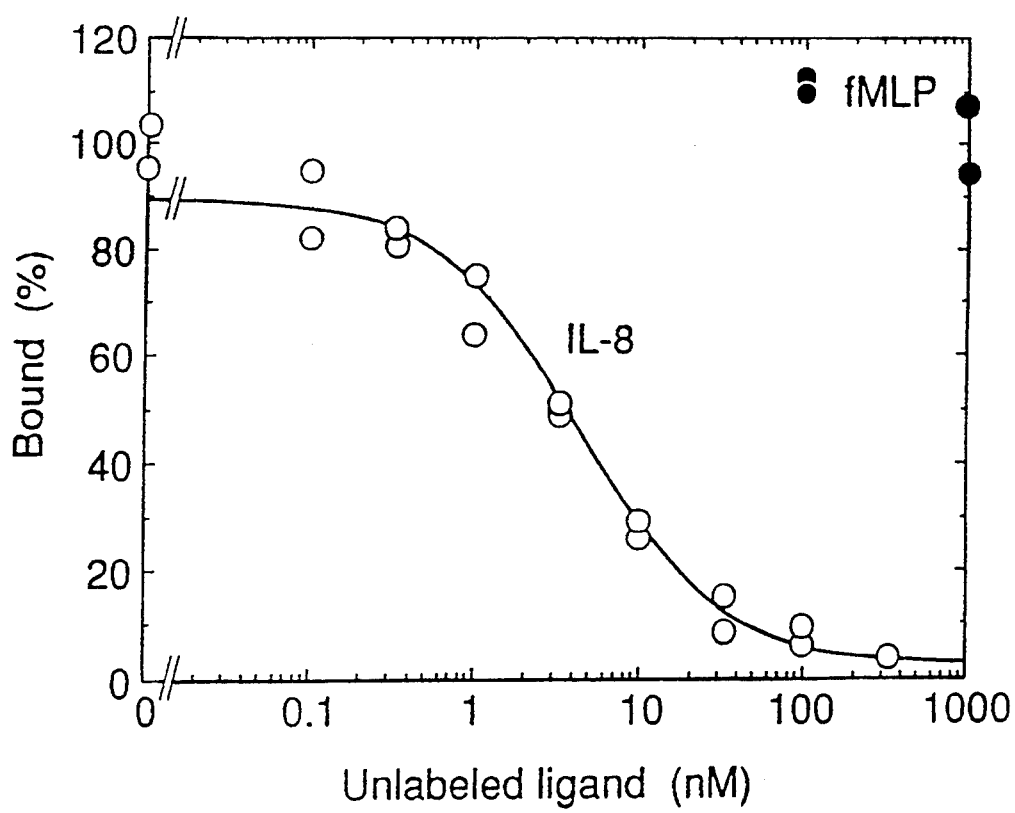
FIG. 1a–b depicts the high affinity binding of IL-8 to COS cells transfected with clone pRK5B.il8r1.1 (IL8R-A).
Figure 1B:
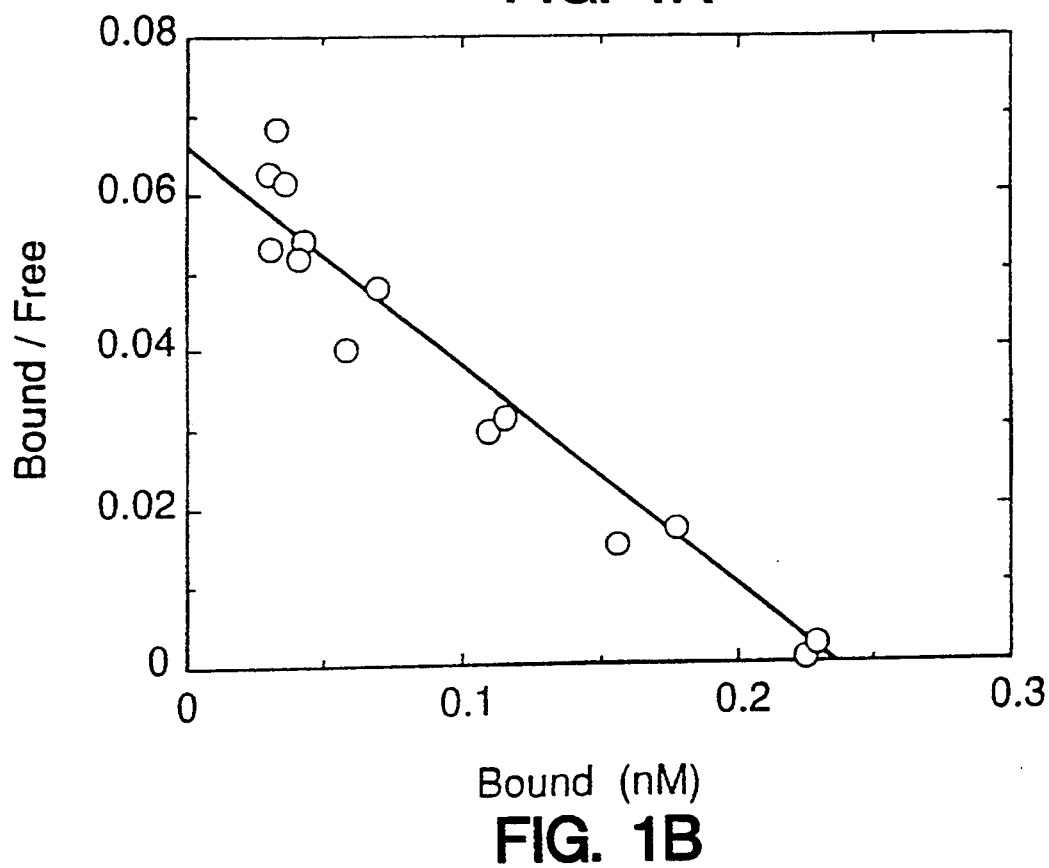
Figure 3A:
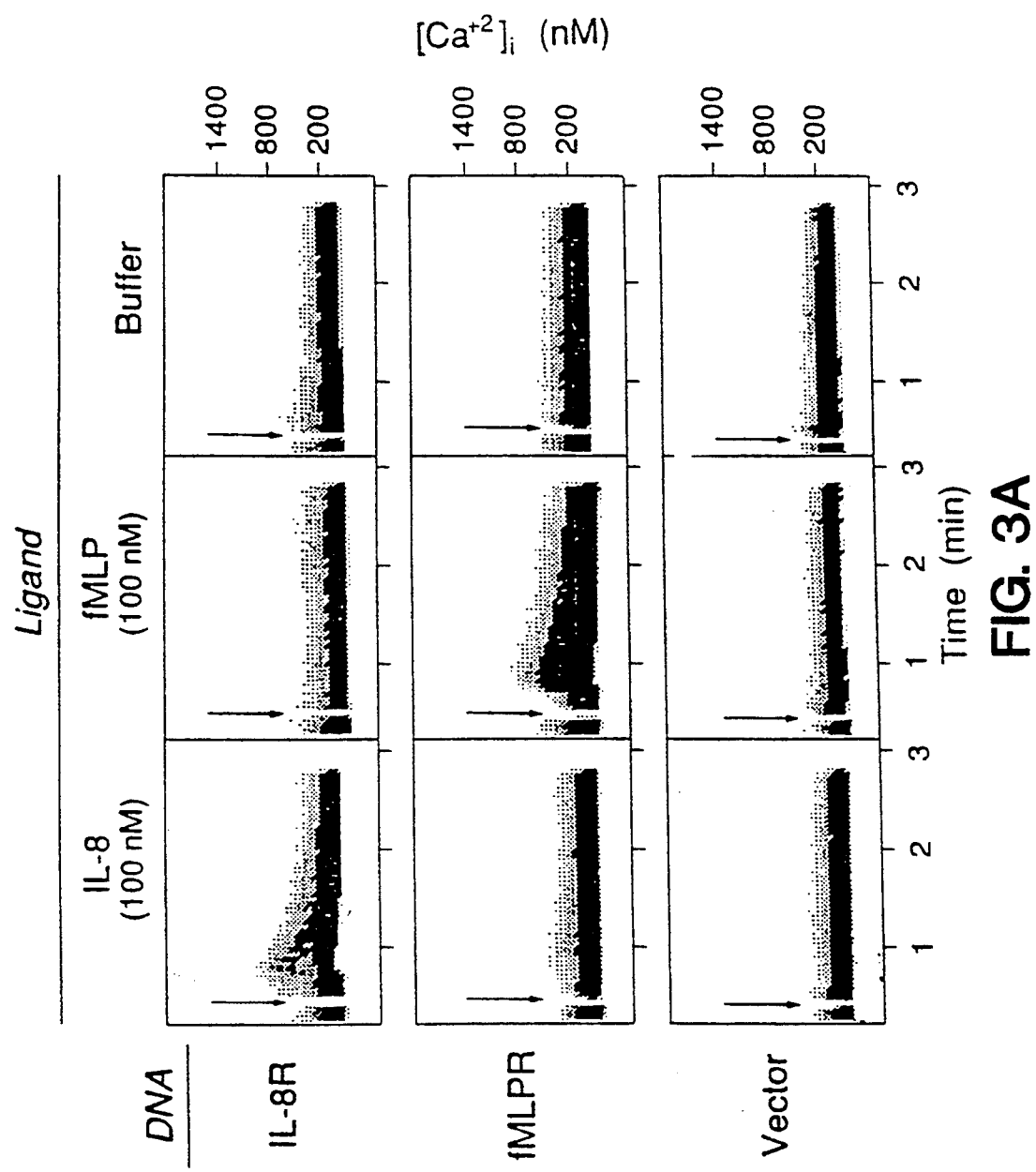
FIG. 3a depicts a flow cytometry determination of the intracellular Ca++ response of human IL-8 receptor A- or fMLP receptor-transfected cells to binding with their ligands. Human embryonic kidney 293 cells were transfected by electroporation (Gearing et al. *EMBO J.*, 8: 3667–3676 (1989)) with IL-8 receptor A (clone pRK5B.il8r1.1), fMLP receptor (human fMLP receptor cDNA (Boulay et al., *Biochem. Biophys. Res. Comm.*, 168: 1103–1109 (1990)) in the vector pRK5), or vector (pRK5B; EP 307,247) DNA. After two days, the cells were loaded with 2 μM indo-1 acetoxymethyl ester in RPMI medium (Sigma) for 30 min at 37° C. Various concentrations of IL-8 or fMLP were added to the cell suspensions and intracellular Ca++ concentrations were measured over a time course with a Coulter 753 flow cytometer using the ratio of 405 and 525 nm fluorescence. Grynkiewicz et al., *J. Biol. Chem.*, 260: 3440–3450 (1985).
Figure 3B:
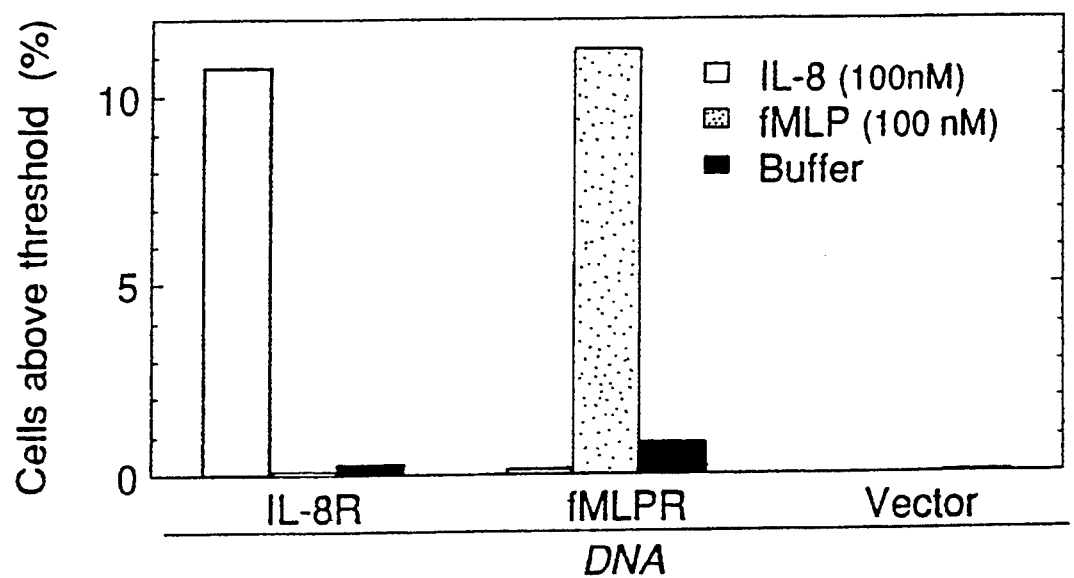
FIG. 3b illustrates the percent of cells above 400 nM $Ca_i$++ for the time period after addition of IL-8 (about 15 sec. into each run).

In general, the following words or phrases have the indicated definition when used in the description, examples, and claims:

"IL8R-BH" is defined as any polypeptide encoded by a nucleic acid sequence that hybridizes under highly stringent conditions to the complement of a nucleic acid sequence encoding a polypeptide having the amino acid sequence depicted in FIG. 6 (SEQ ID NO. 7). The definition includes any fragment of IL8R-BH that can be used to raise antibodies against an IL8R-BH epitope. Thus, the definition covers any fragment of IL8R-BH capable of functioning as an immunogen by itself or capable of functioning as an antigen in a conjugate created by the recombinant or in vitro fusion of the IL8R-BH fragment and an immunogen.

The terms "IL-8 type A receptor," "IL-8 receptor A," "high affinity IL-8 receptor" and "IL8R-A" as used herein are defined as a polypeptide having the amino acid sequence depicted in FIG. 2 (SEQ ID NO. 1).

The terms "IL-8 type B receptor," "IL-8 receptor B," "low affinity IL-8 receptor," "IL-8 receptor of Murphy and Tiffany," and "IL8R-B" as used herein are defined as a polypeptide having the amino acid sequence depicted in FIG. 6 (SEQ ID NO. 7).

The terms "IL-8 receptor," "IL-SR" and "IL8R" as used herein are defined as any chemokine superfamily receptor that is capable of binding to IL-8, such as IL8R-A and IL8R-B.

The term "anti-ILSR-A antibody" as used herein is defined as any antibody capable of binding to IL8R-A. The definition includes antibodies of all immunoglobulin types, such as IgG, IgA, IgM, IgD and IgE, and fragments thereof, and includes antibodies and antibody fragments of all origins, such as polyclonal antibodies, monoclonal antibodies, humanized antibodies and human antibodies produced in transgenic animals or transgenic animal cell culture.

The term "anti-IL8R-B antibody" as used herein is defined as any antibody capable of binding to IL8R-B. The definition includes antibodies of all immunoglobulin types, such as IgG, IgA, IgM, IgD and IgE, and fragments thereof, and includes antibodies and antibody fragments of all origins, such as polyclonal antibodies, monoclonal antibodies, humanized antibodies and human antibodies produced in transgenic animals or transgenic animal cell culture.

The terms "blocking anti-IL8R-B antibody" and "antibody capable of blocking IL8R-B" as used herein are defined as an anti-IL8R-B antibody capable of binding to IL8R-B such that the ability of IL8R-B to bind to a chemokine superfamily member, such as IL-8 or MGSA, is impaired or eliminated. A blocking anti-IL8R-B antibody that blocks the binding of IL-8 to IL8R-B is defined as a blocking anti-IL8R-B antibody that is capable of binding to IL8R-B such that the ability of IL8R-B to bind to IL-8 is impaired or eliminated.

Anti-IL8R-BH antibody is defined as any antibody that binds to an IL8R-BH or fragment thereof. The definition includes antibodies of all immunoglobulin types, such as IgG, IgA, IgM, IgD and IgE, and fragments thereof, and includes antibodies and antibody fragments of all origins, such as polyclonal antibodies, monoclonal antibodies, humanized antibodies and human antibodies produced in transgenic animals or transgenic animal cell culture.

The terms "blocking anti-IL8R-BH antibody" and "antibody capable of blocking IL8R-BH" are defined as an anti-IL8R-BH antibody capable of binding to an IL8R-BH such that the ability of the IL8R-BH to bind to a chemokine superfamily member, such as IL-8 or MGSA, is impaired or eliminated. A blocking anti-IL8R-BH antibody that blocks the binding of IL-8 to IL8R-BH is defined as a blocking anti-IL8R-BH antibody that is capable of binding to an IL8R-BH such that the ability of the ILSR-BH to bind to IL-8 is impaired or eliminated.

The term "IL8R-BH nucleic acid" is defined as any DNA or RNA sequence that encodes an IL8R-BH. The term "IL8R-B nucleic acid" is defined as any DNA or RNA sequence, including the DNA sequence depicted in FIG. 6 (SEQ ID NO. 8), that encodes a polypeptide having the amino acid sequence depicted in FIG. 6 (SEQ ID NO. 7). It will be understood that the discussion of DNA herein applies equally to single and double stranded DNA molecules. Thus, the term "IL8R-BH DNA" refers to any single stranded DNA molecule that encodes an IL8R-BH and to the double stranded DNA molecule formed by such IL8R-BH-encoding strand and its complement.

The terms "high stringency conditions" and "highly stringent conditions" are defined as any nucleic acid hybridization procedures that (1) employ low ionic strength and high temperature for washing, for example, 0.015M NACl/0.0015M sodium citrate/0.1% NaDodSO$_4$ at 50° C; (2) employ during hybridization 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C; or (3) employ hybridization with 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. Conditions of low stringency are set forth in Example 2.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

The starting plasmids herein are commercially available, are publicly available on an unrestricted basis, or can be constructed from such available plasmids in accord with published procedures. In addition, other equivalent plasmids are known in the art and will be apparent to the ordinary artisan. Methods for restriction enzyme digestion, recovery or isolation of DNA, hybridization analysis, and ligation are conventional and by this time well known to the ordinary artisan.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9: 6103–6114 (1981), and Goeddel et al., *Nucleic Acids Res.*, 8: 4057 (1980).

As used herein, the term "mammal" refers to any animal classified as a mammal, including humans, domestic and farm animals, and zoo, sports, or pet animals, such as dogs, horses, cats, cows, etc. Preferably, the mammal herein is human.

As used herein, the term "treatment" refers to therapy as well as prophylactic (preventative) measures.

As used herein, the term "inflammatory disorders" refers to pathological states resulting in inflammation, typically caused by neutrophil chemotaxis. Examples of such disorders include inflammatory skin diseases such as psoriasis; responses associated with inflammatory bowel disease (such as Crohn's disease and ulcerative coliris); adult respiratory distress syndrome; dermatitis; meningitis; encephalitis; uveitis; autoimmune diseases such as rheumatoid arthritis, Sjorgen's syndrome, vasculitis; diseases involving leukocyte diapedesis; CNS inflammatory disorder, multiple organ injury syndrome secondary to septicaemia or trauma; alcoholic hepatitis; antigen-antibody complex mediated diseases; inflammations of the lung, including pleurisy, alveolitis, vasculitis, pneumonia, chronic bronchitis, bronchiectasis, and cystic fibrosis; etc. The preferred indications are inflammatory bowel disease such as ulcerative colitis or a chronic lung inflammation.

II. Suitable Methods for Practicing the Invention

An IL8R-BH for use in anti-IL8R-BH antibody preparation can be isolated from natural sources or synthesized by in vitro or recombinant techniques. What follows is a description of each of these three methods of making ILSR-BH.

1. Isolation of IL8R-BH from a Natural Source

An IL8R-BH for use as an immunogen in the production of antibodies can be obtained from natural sources, such as human neutrophils. Neutrophils can be separated from red blood cells and peripheral blood mononuclear cells by laying whole blood samples on Mono-Poly Resolving Medium (M-PRM) (Flow Laboratories, McLean VA) and recovering the neutrophil band according to the vendor's directions as described in Example 3 below. In one embodiment, the neutrophils expressing IL8R-BH are used as immunogen. In this case, no adjuvant is necessary because the neutrophils are sufficient for generating an immune response in the animal species to be immunized.

In another embodiment, the IL8R-BH receptor is isolated from the neutrophils. First, the neutrophils are lysed and the cell lysate is centrifuged to separate the membrane and soluble protein fractions. The ILSR-BH can then be purified from the membrane fraction by solubilizing the cell membrane with detergent followed by any further purification procedures such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using the appropriate chemokine immobilized on a matrix. The IL8R-BH is optionally conjugated to or administered concomitantly with an adjuvant that is immunogenic in the animal species to be immunized. Appropriate adjuvants for practicing the invention are further described in section 4 below.

2. Recombinant Production of IL8R-BH

In a preferred embodiment of the invention, the IL8R-BH or antigenic fragment thereof is produced by recombinant techniques. In one embodiment, the recombinant IL8R-BH or fragment thereof can be used as immunogen without an adjuvant. In a further embodiment, the immunogen is a fusion protein that contains the amino acid sequence of a suitable adjuvant fused to IL8R-BH. In yet another embodiment, the recombinant IL8R-BH is covalently fused in vitro to an adjuvant or is administered concomitantly with an adjuvant. In a particularly preferred embodiment of the invention, recombinant cells expressing the IL8R-BH as a surface protein anchored to the cell membrane are used to immunize the desired animal species. As in the case of human neutrophils discussed above, recombinant cells expressing IL8R-BH as cell surface protein will generate the desired immunogenic response in the animal without the use of an adjuvant.

The following is a general discussion of methods for the design and construction of recombinant IL8R-BH expression systems.

A. Preparation of DNA Encoding IL8R-BH

All DNA sequences, including the DNA sequence depicted in FIG. 6 (SEQ ID NO. 8), that encode a polypeptide within the amino acid sequence depicted in FIG. 6 (SEQ ID NO. 7) are suitable for use in the recombinant production of IL8R-BH. Additional DNA sequences suitable for use herein include any polypeptide-encoding DNA sequence that hybridizes under highly stringent conditions to the complement of the DNA sequence depicted in FIG. 6, or to the complement of any other DNA sequence encoding a polypeptide having the amino acid sequence depicted in FIG. 6. In one embodiment, candidate hybridizing DNA sequences can be obtained by designing DNA sequences that encode variants of the amino acid sequence depicted in FIG. 6. Such variants include, for example, deletions from, or insertions and substitutions of, residues within the amino acid sequence depicted in FIG. 6. Any combination of deletion, insertion, and substitution can be made to arrive at the final construct, provided that the final construct is encoded by a DNA sequence that hybridizes under highly stringent conditions to the complement of the DNA sequence depicted in FIG. 6, or to the complement of any other DNA sequence that encodes a polypeptide having the amino acid sequence depicted in FIG. 6.

DNA encoding the polypeptide having the amino acid sequence of FIG. 6 and DNA encoding variants of the polypeptide having the amino acid sequence depicted in FIG. 6 can be prepared by a variety of methods known in the art. These methods include, but are not limited to, chemical synthesis by any of the methods described in Engels et al., *Agnew. Chem. Int. Ed. Engl.,* 28: 716-734 (1989), the entire disclosure of which is incorporated herein by reference, such as the triester, phosphite, phosphoramidite and H-phosphonate methods. In one embodiment, codons preferred by the expression host cell are used in the design of the IL8R-BH DNA. IL8R-BH DNA can also be prepared by oligonucleotide-mediated (or site-directed) mutagenesis, PCR mutagenesis, and cassette mutagenesis of an earlier prepared DNA encoding a variant or a non-variant version of IL8R-BH. These techniques can utilize IL8R-BH nucleic acid (DNA or RNA), or nucleic acid complementary to the IL8R-BH nucleic acid.

Oligonucleotide-mediated mutagenesis is a preferred method for preparing substitution, deletion, and insertion variants of IL8R-BH DNA. This technique is well known in the art, for example as described by Adelman et al., *DNA,* 2: 183 (1983). Briefly, the ILSR-BH DNA is altered by hybridizing an oligonucleotide encoding the desired mutation to a DNA template, where the template is the single-stranded form of a plasmid or bacteriophage containing the unaltered IL8R-BH DNA. After hybridization, a DNA polymerase is used to synthesize an entire second complementary strand of the template that will thus incorporate the oligonucleotide primer, and will code for the selected alteration in the ILSR-BH DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA,* 75: 5765 (1978).

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the IL8R-BH, and the other strand (the original template) encodes the unaltered sequence of the IL8R-BH. This heteroduplex molecule is then transformed into a suitable host cell, usually a prokaryote such as *E. coli* JM101. The cells are plated onto agarose plates, and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding IL8R-BH mutants at more than one site may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of the IL8R-BH. While the following discussion refers to DNA, it is understood that the technique also finds application with RNA. The PCR technique generally refers to the following procedure (see Erlich, supra, the chapter by R. Higuchi, p. 61-70). When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone°

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

Another method for preparing variants, cassette mutagenesis, is based on the technique described by Wells et al., *Gene*, 34: 315 (1985).

B. Insertion of DNA into a Cloning Vehicle

The DNA encoding IL8R-BH is inserted into a replicable vector for further cloning (amplification of the DNA) or for expression. Many vectors are available, and selection of the appropriate vector will depend on (1) whether it is to be used for DNA amplification or for DNA expression, (2) the size of the DNA to be inserted into the vector, and (3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, a signal sequence may be a component of the vector, or it may be a part of the IL8R-BH DNA that is inserted into the vector. The native pro IL8R-B is directed to the cell surface in recombinant human 293 cells as described in Example 3 below, but the native pro IL8R-B does not contain a conventional signal and no N-terminal polypeptide is cleaved during post-translational processing of the polypeptide during membrane insertion of the IL8R-B.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is homologous to a sequence found in Bacillus genomic DNA. Transfection of Bacillus with this vector results in homologous recombination with the genome and insertion of the IL8R-BH DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 (1982)), mycophenolic acid (Mulligan et al., *Science*, 209: 1422 (1980)) or hygromycin (Sugden et al., *Mol. Cell. Biol.*, 5: 410-413 (1985)). The three examples given above employ bacterial genes under eukaryotic control to convey resistance to the appropriate drug (G418 or neomycin (geneticin), xgpt (mycophenolic acid), and hygromycin, respectively.)

Another example of suitable selectable markers for mammalian cells are those that enable the identification of cells competent to take up the IL8R-BH nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the IL8R-BH. Amplification is the process by which genes in greater demand for the production of a protein critical for growth are reiterated in tandem within the chromosomes of successive generations of recombinant cells. Increased quantities of the IL8R-BH are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the IL8R-BH. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the IL8R-BH, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7. Stinchcomb et al., *Nature*, 282: 39 (1979); Kingsman et al., *Gene*, 7: 141 (1979); or Tschemper et al., *Gene*, 10: 157 (1980). The trp1 gene provides a selection marker for a mutant strain of yeast lacking the ability to grow in tryptophan, for example, ATCC No. 44076 or PEP4-1. Jones, *Genetics*, 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression vectors usually contain a promoter that is recognized by the host organism and is operably linked to the IL8R-BH nucleic acid. Promoters are untranslated sequences located upstream (5') to the start codon of a structural gene transcription and translation of a particular nucleic acid sequence, such as the IL8R-BH, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. Both the native IL8R-B promoter sequence and many heterologous promoters can be used to direct amplification and/or expression of the IL8R-BH DNA in eukaryotic host cells. However, heterologous promoters are preferred, as they generally permit greater transcription and higher yields of expressed IL8R-BH as compared to the native IL8R-B promoter.

Promoters suitable for use with prokaryotic hosts include the β-lactamase and lactose promoter systems (Chang et al., *Nature*, 275: 615 (1978); and Goeddel et al., *Nature*, 281: 544 (1979)), alkaline phosphatase, a tryptophan (trp) promoter system (Goeddel, *Nucleic Acids Res.*, 8: 4057 (1980) and EP 36,776) and hybrid promoters such as the tac promoter (deBoer et al., *Proc. Natl. Acad. Sci. USA*, 80: 21-25 (1983)). However, other known bacterial promoters are suitable. Their nucleotide sequences have been published, thereby enabling a skilled worker to operably ligate them to DNA encoding the IL8R-BH (Siebenlist et al., *Cell*, 20: 269 (1980)) using linkers or adaptors to supply any required restriction sites. Promoters for use in bacterial systems also generally will contain a Shine-Dalgarno (S.D.) sequence operably linked to the DNA encoding the IL8R-BH.

Suitable promoting sequences for use with yeast hosts include the promoters for 3-phosphoglycerate kinase (Hitzeman et al., *J. Biol. Chem.*, 255: 2073 (1980)) or other glycolytic enzymes (Hess et al., *J. Adv. Enzyme Reg.*, 7: 149 (1968); and Holland, *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

IL8R-BH transcription from vectors in mammalian host cells is controlled by promoters obtained from the genomes of viruses such as polyoma virus, fowlpox virus (UK 2,211,504 published 5 Jul. 1989), adenovirus (such as Adenovirus 2), bovine papilloma virus, arian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the native IL8R-B promoter sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273: 113 (1978); Mulligan and Berg, *Science*, 209: 1422-1427 (1980); Pavlakis et al., *Proc. Natl. Acad. Sci. USA*, 78: 7398-7402 (1981). The immediate early promoter of the human cytomegalovirus is conveniently obtained as a HindIII E restriction fragment. Greenaway et al., *Gene*, 18: 355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295:503–508 (1982) on expressing cDNA encoding immune interferon in monkey cells, Reyes et al., *Nature*, 297: 598–601 (1982) on expression of human β- interferon cDNA in mouse cells under the control of a thymidine kinase promoter from herpes simplex virus, Canaani and Berg, *Proc. Natl. Acad. Sci. USA*, 9:5166–5170 (1982) on expression of the human interferon β1 gene in cultured mouse and rabbit cells, and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding IL8R-BH by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA*, 78: 993 (1981)) and 3' (Lusky et al., *Mol. Cell Bio.*, 3: 1108 (1983)) to the transcription unit, within an intron (Banerji et al., *Cell*, 33: 729 (1983)) as well as within the coding sequence itself (Osborne et al., *Mol. Cell Bio.*, 4: 1293 (1984)). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the IL8R-BH DNA, but is preferably located at a site 5′ from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5′ and, occasionally 3′ untranslated regions of eukaryotic or viral DNAs or cDNAs. These regions contain nucleotide segments transcribed as polyadenylated fragments in the untranslated portion of the mRNA encoding the IL8R-BH. The 3′ untranslated regions also include transcription termination sites.

Suitable vectors containing one or more of the above listed components and the desired coding and control sequences are constructed by standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

Particularly useful in the practice of this invention are expression vectors that provide for the transient expression in mammalian cells of DNA encoding the IL8R-BH. In general, transient expression involves the use of an expression vector that is able to replicate efficiently in a host cell, such that the host cell accumulates many copies of the expression vector and, in turn, synthesizes high levels of a desired polypeptide encoded by the expression vector.

Other methods, vectors, and host cells suitable for adaptation to the synthesis of the IL8R-BH in recombinant vertebrate cell culture are described in Gething et al., *Nature*, 293: 620–625 (1981); Mantei et al., *Nature*, 281: 40–46 (1979); Levinson et al., EP 117,060; and EP 117,058. A particularly useful plasmid for mammalian cell culture expression of the IL8R-BH is pRK5 (EP pub. no. 307,247) or pSVI6B (PCT pub. no. WO 91/08291 published 13 Jun. 1991).

C. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcescens*. One preferred *E. coli* cloning host is *E. coli* 294 (ATCC 31,446), although other strains such as *E. coli* B, *E. coli* $_{102}$ 1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for vectors containing IL8R-BH DNA. *Saccharomyces cerevisiae*, or common baker's yeast, is the most commonly used among lower eukaryotic host microorganisms. However, a number of other genera, species, and strains are commonly available and useful herein, such as *S. pombe* (Beach and Nurse, *Nature*, 290: 140 (1981)), *Kluyveromyces lactis* (Louvencourt et al., *J. Bacteriol.*, 737 (1983)), *yarrowia* (EP 402,226) , *Pichia pastoris* (EP 183,070) , *Trichoderma reesia* (EP 244,234), *Neurospora crassa* (Case et al., *Proc. Natl. Acad. Sci. USA*, 76: 5259–5263 (1979)), and Aspergillus hosts such as *A. nidulans* (Ballance et al., *Biochem. Biophys Res. Commun.*, 112: 284–289 (1983); Tilburn et al., *Gene*, 26: 205–221 (1983); Yelton et al., *Proc. Natl. Acad. Sci., USA*, 81: 1470–1474 (1984)) and *A. niger* (Kelly and Hynes, *EMBO J.*, 4: 475–479 (1985)).

Suitable host cells for the expression of glycosylated IL8R-BH polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology*, 6: 47–55 (1988); Miller et al., in *Genetic Engineering*, Setlow, J.

K. et al., 8: 277-279 (Plenum Publishing, 1986), and Maeda et al., *Nature,* 315: 592-594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the IL8R-BH DNA. During incubation of the plant cell culture with *A. tumefaciens,* the DNA encoding IL8R-BH is transferred to the plant cell host such that it is transfected, and will, under appropriate conditions, express the IL8R-BH DNA. In addition, regulatory and signal sequences compatible with plant cells are available, such as the nopaline synthase promoter and polyadenylation signal sequences. Depicker et al., *J. Mol. Appl. Gen.,* 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989.

However, interest has been greatest in vertebrate cells, and propagation of vertebrate cells in culture (tissue culture) has become a routine procedure in recent years (*Tissue Culture,* Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36: 59 (1977)); baby hamster kidney cells (BHK, ATCC CCL 10); Chinese hamster ovary cells/-DHFR (CHO, Urlaub and Chasin, *Proc. Natl. Acad. Sci. USA,* 77: 4216 (1980)); mouse sertoli cells (44, Mather, *Biol. Reprod.,* 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383: 44-68 (1982)); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene,* 23: 315 (1983) and WO 89/05859 published 29 Jun. 1989. For mammalian cells without such cell walls, the calcium phosphate precipitation method described in sections 16.30-16.37 of Sambrook et al. supra, is preferred. General aspects of mammalian cell host system transformations have been described by Axel in U.S. 4,399,216 issued 16 Aug. 1983. Transformations into yeast are typically carried out according to the method of Van Solingen et al., *J. Bact.,* 130: 946 (1977) and Hsiao et al., *Proc. Natl. Acad. Sci. (USA),* 76: 3829 (1979). However, other methods for introducing DNA into cells such as by nuclear injection, electroporation, or by protoplast fusion may also be used.

D. Culturing the Host Cells

Prokaryotic cells used to produce the IL8R-BH polypeptide are cultured in suitable media as described generally in Sambrook et al., supra.

The mammalian host cells used to produce the IL8R-BH can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.,* 58: 44 (1979), Barnes and Sato, *Anal. Biochem.,* 102: 255 (1980), U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin ™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the IL8R-BH can be produced by homologous recombination, or with recombinant production methods utilizing control elements introduced into cells already containing DNA encoding the IL8R-BH. For example, a powerful promoter/enhancer element, a suppressor, or an exogenous transcription modulatory element is inserted in the genome of the intended host cell in proximity and orientation sufficient to influence the transcription of DNA encoding the desired ILSR-BH. One next screens for cells making the IL8R-BH, or increased or decreased levels of expression, as desired.

E. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77: 5201–5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal and may be prepared in any mammal. Conveniently, the antibodies can be prepared against a native IL8R-B polypeptide or against a synthetic peptide based on the DNA sequences provided herein as described further in Section 4 below.

F. Purification of the IL8R-BH Polypeptide

The IL8R-BH is recovered from the culture cells by solubilizing cell membrane in detergent. As a first step, the cells are centrifuged to separate them from culture medium. The membrane and soluble protein fractions are then separated. The IL8R-BH may then be purified from the membrane fraction of the culture lysate by solubilization with detergents followed by suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using the appropriate chemokine immobilized on a matrix.

3. In Vitro Chemical Synthesis of IL8R-BH

In addition to the recombinant production of IL8R-BH described above, IL8R-BH can also be produced by in vitro chemical synthesis. In one embodiment, the desired ILSR-BH is constructed by the solid phase synthesis method described by Merrifield, *Science*, 232: 342–347 (1986). In this method, a growing polypeptide chain is covalently anchored, usually by its C-terminus, to an insoluble solid support such as beads of polystyrene resin, and the appropriately blocked amino acids and reagents are added in the proper sequence. This permits the quantitative recovery of the desired peptide product by simply filtering and washing the beads. It will be appreciated that any method of peptide synthesis now or hereafter developed can be used to synthesize IL8R-BH for use in the present invention.

4. Anti-IL8R-BH Antibody Preparation

Polyclonal antibodies to the IL8R-BH generally are raised in animals by multiple subcutaneous (sc) or intraperitoneal (ip) injections of the IL8R-BH and an adjuvant. Immunization with recombinant cells expressing the IL8R-BH (e.g. mouse or CHO cells expressing IL8R-BH) may be satisfactory, or it may be useful to separate the IL8R-BH and conjugate it or a fragment containing the amino acid sequence of the desired IL8R-BH antigenic site to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals ordinarily are immunized against the cells or immunogenic conjugates of IL8R-BH with monophosphoryl lipid A (MPL)/trehalose dicorynomycolate (TDM) (Ribi Immunochem. Research, Inc., Hamilton, Mont.) and injecting the solution intradermally at multiple sites. Two weeks later the animals are boosted with the original amount of conjugate in MPL/TDM. 7 to 14 days later animals are bled and the serum is assayed for anti-IL8R-BH titer. Animals are boosted until the titer plateaus. Preferably, the animal is boosted with the conjugate of the same IL8R-BH, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The hybridoma technique described originally by Koehler and Milstein, *Eur. J. Immunol.*, 6: 511 (1976) and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

The hybrid cell lines can be maintained in vitro in cell culture media. The cell lines producing the antibodies can be selected and/or maintained in a medium containing hypoxanthine-aminopterin thymidine (HAT). In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant or ascites fluid by conventional methods such as immune precipitation, ion-exchange chromatography, affinity chromatography such as protein A/protein G column chromatography, or the like. The antibodies described herein are also recovered from hybridoma cell cultures by conventional methods such as precipitation with 50% ammonium sulfate. The purified antibodies can then be sterile filtered.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

The monoclonal antibodies herein include hybrid and recombinant antibodies produced by splicing a variable (including hypervariable) domain of an anti-IL8R-BH antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g. Cabilly, al., U.S. Pat. No. 4,816,567; Mage & Lamoyi, in *Monoclonal Antibody Production Techniques and Applications*, pp.79-97 (Marcel Dekker, Inc., New York, 1987).)

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method described by Kohler a Milstein, supra, or may be made by recombinant DNA methods (Cabilly, et al., supra).

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-IL8R-BH monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an IL8R-BH and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321, 522-525 (1986); Riechmann et al., *Nature* 332, 323-327 (1988); Verhoeyen et al., *Science* 239, 1534-1536 (1988)), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed 21 Aug. 1992, which is a continuation-in-part of application Ser. No. 715,272 filed 14 Jun. 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region (J) gene in chimeric and germ-line mutant mice results in complete inhibition of endogenous antibody production. Transfer of the human germ-line immunoglobulin gene array in such germ-line mutant animals will result in the production of human antibodies upon antigen challenge, and the antibodies can be harvested from the animal's blood or other body fluid. See, e.g. Jakobovits et al., *Proc. Natl. Acad. Sci. USA* 90, 2551–255 (1993); Jakobovits et al., *Nature* 362, 255–258 (1993). In addition, the cells expressing the desired antibody can be isolated from the animal host and used to produce the antibody in cell culture, and the antibody can be harvested from the cell culture by standard methods.

In one embodiment of the invention, the monoclonal antibody is specific for each target IL8R-BH polypeptide, and will not cross-react with rabbit fMLP receptor (Thomas et al., *J. Biol. Chem.*, supra), human fMLP receptor, human C5a receptor, the IL-8 type A receptor, or other receptors for the chemokine superfamily. Antibodies specific for IL8R-B are preferred. The antibody is selected to be either agonistic, antagonistic, or to have no effect on the activity of a chemokine superfamily member in binding to or activating the receptor.

The invention also provides for cross-reactive antibodies capable of binding two different IL8Rs. For example, one can select an IL-8 antagonist antibody that binds to an epitope of IL8R-A and to an epitope of an IL8R-BH. This could be readily accomplished by routine screening methods. For example, the candidate antibodies can be assayed for their ability to compete against labelled IL-8 for binding to cells bearing the IL8R-A receptor, and then the same study conducted with cells bearing the IL8R-BH receptor. Antibodies that inhibit IL-8 activation or binding to both cells are then selected as therapeutic candidates. On the other hand, antibodies that can discriminate between the IL8R-A and IL8R-B receptors and bind only to one or the other are also useful in diagnosis and drug therapy. The IL8R-A receptor binds MGSA poorly, in contrast to the IL8R-B receptor.

The invention further provides for bifunctional, or bispecific, antibodies in which an antigen-binding site specific for one IL8R and an antigen-binding site specific for a different IL8R are incorporated into a single molecule. Such bispecific antibodies may be prepared by chemical cross-linking (Brennan et al., *Science* 229: 81 (1985)), disulfide exchange, or the production of hybrid-hybridomas (quadromas). Quadromas are constructed by fusing hybridomas that secrete two different types of antibodies against two different antigens (Milstein and Cuello, *Nature*, 305: 537–539 (1983); Kurokawa et al., *Biotechnology*, 7: 1163 (1989)). Because of the random assortment of immunoglobulin heavy and light chains, these hybridomas (quadromas) produce a potential mixture of 10 different antibody molecules, of which the one having the correct bispecific structure needs to be isolated and purified. Bispecific antibodies can also be prepared by the so-called transfectoma method, essentially as described by Morrison, *Science* 229: 1202–1207 (1985). The invention additionally encompasses bispecific antibody structures produced within recombinant microbial hosts as described in PCT application WO 93/11161 and Holliger et al., *Proc. Natl. Acad. Sci. USA*, 90: 6444–6448 (1993). Also included are bispecific linear molecules, such as the so-called "Janusin" structures described by Traunecker et al., *EMBO*, 10: 3655–3659 (1991). This can be accomplished by genetically removing the stop codons at the end of a gene encoding a monomeric single-chain antigen-binding protein and inserting a linker and a gene encoding a second single-chain antigen-binding protein (see WO 93/11161, supra). Such a molecule with dual specificity for IL-8 type A receptor and IL-8 type B receptor would comprise a domain having IL8R-A antagonist activity and a domain having IL8R-B antagonist activity.

5. Therapeutic Compositions and Administration of Anti-IL8R-BH Antibodies

Therapeutic formulations of anti-ILSR-BH antibodies are prepared for storage by mixing antibody having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The anti-IL8R-BH antibody to be used for in vivo administration must be sterile. This is readily accomplished by filtration through sterile filtration membranes, prior to or following lyophilization and reconstitution. The anti-IL8R-BH antibody ordinarily will be stored in lyophilized form or in solution.

Therapeutic anti-IL8R-BH antibody compositions generally are placed into a container having a sterile access port, for example, an intravenous solution bag or vial having a stopper pierceable by a hypodermic injection needle.

The route of anti-IL8R-BH antibody administration is in accord with known methods, e.g. injection or infusion by intravenous, intraperitoneal, intracerebral, intramuscular, intraocular, intraarterial, intracerebrospinal, or intralesional routes, or by sustained release systems as noted below. Preferably the antibody is given systemically.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers,* 22: 547–556 (1983)), poly (2-hydroxyethylmethacrylate) (Langer et al., *J. Biomed. Mater. Res.,* 15: 167–277 (1981) and Langer, Chem. Tech., 12:98–105 (1982)), ethylene vinyl acetate (Langer et al., supra) or poly-D-(—)-3-hydroxybutyric acid (EP 133,988). Sustained-release anti-IL8R-BH antibody compositions also include liposomally entrapped antibody. Liposomes containing antibody are prepared by methods known per se: DE 3,218,121; Epstein et al., *Proc. Natl. Acad. Sci. USA,* 82: 3688–3692 (1985); Hwang et al., *Proc. Natl. Acad. Sci. USA,* 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal antibody therapy.

Anti-IL8R-BH antibody can also be administered by inhalation. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-IL8R-BH antibody can be aerosolized using a fluorocarbon formulation and a metered dose inhaler, or inhaled as a lyophilized and milled powder.

An "effective amount" of anti-IL8R-BH antibody to be employed therapeutically will depend, for example, upon the therapeutic objectives, the route of administration, the type of anti-IL8R-BH antibody employed, and the condition of the patient. Accordingly, it will be necessary for the therapist to titer the dosage and modify the route of administration as required to obtain the optimal therapeutic effect. Typically, the clinician will administer the anti-IL8R-BH antibody until a dosage is reached that achieves the desired effect. The progress of this therapy is easily monitored by conventional assays.

In the treatment and prevention of an inflammatory disorder by an anti-IL8R-BH antibody, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of aministration, and other factors known to medical practitioners. The "therapeutically effective amount" of antibody to be administered will be governed by such considerations, and is the minimum amount necessary to prevent, ameliorate, or treat the inflammatory disorder, including treating chronic respiratory diseases and reducing inflammatory responses. Such amount is preferably below the amount that is toxic to the host or renders the host significantly more susceptible to infections.

As a general proposition, the initial pharmaceutically effective amount of the antibody administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of antibody, depending on the pattern of pharmacokinetic decay that the practitioner wishes to achieve.

As noted above, however, these suggested amounts of antibody are subject to a great deal of therapeutic discretion. The key factor in selecting an appropriate dose and scheduling is the result obtained, as indicated above.

The antibody need not be, but is optionally formulated with one or more agents currently used to prevent or treat the inflammatory disorder in question. For example, in rheumatoid arthritis, the antibody may be given in conjunction with a glucocorticosteroid. The effective amount of such other agents depends on the amount of anti-IL8R-BH antibody present in the formulation, the type of disorder or treatment, and other factors discussed above. These are generally used in the same dosages and with administration routes as used hereinbefore or about from 1 to 99% of the heretofore employed dosages.

6. Diagnostic Uses of Anti-IL8R-BH Antibodies

Anti-IL8R-BH antibodies are useful in diagnostic assays for IL8R-BH expression in specific cells or tissues wherein the antibodies are labeled as described below and/or are immobilized on an insoluble matrix. Anti-IL8R-BH antibodies also are useful for the affinity purification of the IL8R-BH from recombinant cell culture or natural sources. The anti-IL8R-BH antibodies that do not detectably cross-react with other IL8Rs can be used to purify each IL8R-BH free from other homologous receptors. Anti-IL8R-BH antibodies that are chemokine antagonists are useful as anti-inflammatory agents or in the treatment of other chemokine superfamily-mediated disorders.

Suitable diagnostic assays for the IL8R-BH are well known per se. For example, a biological sample may be assayed for IL8R-BH by obtaining the sample from a desired source, admixing the sample with anti-IL8R-BH antibody to allow the antibody to form antibody/IL8R-BH complex with any IL8R-BH present in the mixture, and detecting any antibody/IL8R-BH complex present in the mixture. The biological sample may be prepared for assay by methods known in the art which are suitable for the particular sample. The methods of admixing the sample with antibodies and the methods of detecting antibody/IL8R-BH complex are chosen according to the type of assay used. Such assays include competitive and sandwich assays, and steric inhibition assays. Competitive and sandwich methods employ a phase-separation step as an integral part of the method while steric inhibition assays are conducted in a single reaction mixture.

Analytical methods for the IL8R-BH all use one or more of the following reagents: labeled IL8R-BH analogue, immobilized IL8R-BH analogue, labeled anti-IL8R-BH antibody, immobilized anti-IL8R-BH antibody and steric conjugates. The labeled reagents also are known as "tracers."

The label used is any detectable functionality that does not interfere with the binding of IL8R-BH and anti-IL8R-BH antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, $\beta$-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bisimidates, bis-diazotized benzidine, and the like may be used to tag the antibodies with the above-described fluorescent, chemiluminescent, and enzyme labels. See, for example, U.S. Pat. Nos. 3,940,475 (fluorimetry) and 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); and Nygren, *J. Histochem. and Cytochem.*, 30: 407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymoogy*, ed. J. J. Langone and H. Van Vunakis, Vol. 73 (Academic Press, New York, New York, 1981), pp. 147–166.

Immobilization of reagents is required for certain assay methods. Immobilization entails separating the anti-IL8R-BH antibody from any IL8R-BH that remains free in solution. This conventionally is accomplished by either insolubilizing the anti-IL8R-BH antibody or IL8R-BH analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-IL8R-BH antibody or IL8R-BH analogue afterward, e.g., by immunoprecipitation.

Other assay methods, known as competitive or sandwich assays, are well established and widely used in the commercial diagnostics industry.

Competitive assays rely on the ability of a tracer IL8R-BH analogue to compete with the test sample IL8R-BH for a limited number of anti-IL8R-BH antibody antigen-binding sites. The anti-IL8R-BH antibody generally is insolubilized before or after the competition and then the tracer and IL8R-BH bound to the anti-IL8R-BH antibody are separated from the unbound tracer and IL8R-BH. This separation is accomplished by decanting (where the binding partner was preinsolubilized) or by centrifuging (where the binding partner was precipitated after the competitive reaction). The amount of test sample IL8R-BH is inversely proportional to the amount of bound tracer as measured by the amount of marker substance. Dose-response curves with known amounts of IL8R-BH are prepared and compared with the test results to quantitatively determine the amount of IL8R-BH present in the test sample. These assays are called ELISA systems when enzymes are used as the detectable markers.

Another species of competitive assay, called a "homogeneous" assay, does not require a phase separation. Here, a conjugate of an enzyme with the IL8R-BH is prepared and used such that when anti-IL8R-BH antibody binds to the IL8R-BH the presence of the anti-IL8R-BH antibody modifies the enzyme activity. In this case, the IL8R-BH or its immunologically active fragments are conjugated with a bifunctional organic bridge to an enzyme such as peroxidase. Conjugates are selected for use with anti-IL8R-BH antibody so that binding of the anti-IL8R-BH antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small IL8R-BH fragment so that antibody to hapten is substantially unable to bind the conjugate at the same time as anti-IL8R-BH antibody. Under this assay procedure the IL8R-BH present in the test sample will bind anti-IL8R-BH antibody, thereby allowing anti-hapten to bind the conjugate, resulting in a change in the character of the conjugate hapten, e.g., a change in fluorescence when the hapten is a fluorophore.

Sandwich assays particularly are useful for the determination of IL8R-BH or anti-IL8R-BH antibodies. In sequential sandwich assays an immobilized anti-IL8R-BH antibody is used to adsorb test sample IL8R-BH, the test sample is removed as by washing, the bound IL8R-BH is used to adsorb a second, labeled anti-IL8R-BH antibody and bound material is then separated from residual tracer. The amount of bound tracer is directly proportional to test sample IL8R-BH. In "simultaneous" sandwich assays the test sample is not separated before adding the labeled anti-IL8R-BH. A sequential sandwich assay using an anti-IL8R-BH monoclonal antibody as one antibody and a polyclonal anti-IL8R-BH antibody as the other is useful in testing samples for IL8R-BH.

The foregoing are merely exemplary diagnostic assays for IL8R-BH. Other methods now or hereafter developed that use anti-IL8R-BH antibody for the determination of IL8R-BH are included within the scope hereof, including the bioassays described above.

All references cited in this specification are expressly incorporated by reference.

The following examples are offered by way of illustration and not by way of limitation.

EXAMPLE 1

Selection of IL8R-A clones

To obtain the clone pRK5B.il8r1.1, a cDNA (Gubler and Hoffman, Gene, 25: 263-269 (1983)) library of 1,000,000 clones was constructed from human neutrophil mRNA (Chirgwin et al., Biochem., 18: 5294-5299 (1979)) in the vector pRK5B using BstXI linkers. The cDNA was produced in blunted form. Hemi-kinase BstXI linkers were ligated to the cDNA, and the linkers ligated into the pRK5B vector that had been BstXI digested, phosphatased, and the long vector fragment isolated. pRK5B is a derivative of pRK5 (EP 307,247) that contains a cytomegalovirus promoter followed by a 5' intron, BstXI cloning site, and an SV40 early polyadenylation signal, although it will be understood that any mammalian cell expression vector will be satisfactory. 58 pools of 2500 clones each were transfected into COS-7 cells by electroporation (Gearing et al., supra) of 20 μg of DNA into 3,750,000 cells. After 2 days of growth on 150-mm dishes in medium (50:50::Ham's F12: DMEM) containing 10% fetal calf serum, $^{125}$I-IL-8 binding was performed. Purified human 72 amino acid IL-8 made in E. coli (Hébert et al., J. Immunology, 145: 3033-3040 (1990)) was labeled by the lactoperoxidase method (Morrison and Bayse, Biochem., 9: 2995-3000 (1970)) to about 1100 Ci/mmol and was at least 85% bindable. Dishes were rinsed twice with phosphate-buffered saline, and binding was performed with 8 ml per dish of growth medium containing 2.5% fetal calf serum and about 0.5 nM $^{125}$I-IL-8. After 2 hr at 37° C., the plates were rinsed three times with phosphate-buffered saline, and the bottoms were cut out (Pacholczyk et al., BioTechniques, 9: 556-558 (1990)) and autoradiographed. Each positive pool of 2500 cDNA clones was subsequently partitioned into pools of 800 clones, and each of these was used to transfect COS-7 cells, followed by $^{125}$I-IL-8 binding assays performed on transfected cells. Each positive pool in turn was subdivided through pools of 185, 30 and finally a single clone(s) until single positive clones were identified to obtain the pure isolate. Since only a portion of each pool was used for transfection it was unnecessary to rescue clones from transformants.

Binding competition was performed with electroporated COS-7 cells after 1 day of expression in 6-well dishes (about 175,000 cells/dish). Binding was performed with radioiodinated wild type IL-8 in a binding medium ($Ca^{2+}$ and $Mg^{2+}$-free Hanks buffered supplemented with 25 nM Hepes and 0.5% BSA) at 4° C. for about 2 hr. Wells were then washed, the cells harvested with trypsin, and counted. No specific binding was found in parallel wells containing cells transfected with vector pRK5B DNA. Neutrophil binding was performed as described in Pacholczyk et al., supra, except that a 2 hr incubation at 4° C. was used.

EXAMPLE 2

Selection of IL8R related receptors

Existing λgt10 cDNA libraries from the human cell line HL60 and from human peripheral blood lymphocytes were screened at low stringency with a probe from the coding region of the cloned high-affinity human IL-8 receptor (FIG. 2). The probe was the 874 bp PstI/NcoI fragment of the receptor containing the coding region for amino acids 23-314. Hybridization was in 20% formamide, 4×SSC, 50 mM sodium phosphate buffer, pH 7, 0.2 g/l sonicated salmon sperm DNA, 5×Denhardts, 10% dextran sulfate, at 42° C. with a wash performed with 1×SSC, 0.1% SDS at 50° C. A number of duplicate spots of varying intensity (about 60) were picked, plaque purified, subcloned into plasmid vectors, and sequenced. Nucleic acid sequencing began with the selection of spots of greatest intensity. Sufficient sequence was obtained for a given spot (phage) to determine whether or not evidence of structural or sequence homology with the IL-8 receptor existed. If it did, then the remainder of the gene was obtained (if necessary) and sequenced in its entirety.

To avoid sequencing all of the clones that contain the same gene, the sequence was then used to probe the parental collection of IL-8 receptor DNA hybridizing clones under high stringency conditions in order to identify and discard other spots containing the same hybridizing gene. This technique was highly effective in reducing the sequencing burden. For example, one gene was represented by about one third of the initial 60 clones, and on this result alone the negative screen was able to considerably reduce the work involved in sequencing the clones.

From this screen, two new gene sequences were found that are clearly related to the IL-8 receptor. The coding region for one new gene was split between two clones (8rr.20 and 8rr.15). The combined sequence of this gene (8rr.20.15) is shown in FIG. 4. The complete coding region for the second gene was found in clone 8rr.9 (FIG. 5). The predicted amino acid sequence of 8rr.20.15 is 34% identical with both the high and low affinity IL-8 receptor sequences. The sequence of 8rr.9 is 36% and 38% identical with the high and low affinity IL-8 receptor sequences, respectively (Holmes et al., Science, 253: 1278 (1991) and Murphy and Tiffany, supra). The amino acid sequence of 8rr.20.15 and 8rr.9 are 31% identical. Use of this probe under low stringency conditions did not produce detectable hybridization to the fMLP receptor genes that were expected to be represented in these libraries.

EXAMPLE 3

Generation of MAbs to IL8R-A

Monoclonal antibodies to IL-8 type A receptor were generated by immunizing mice with synthetic peptides corresponding to various extracellular domains of IL8R-A or with stably transfected cells expressing IL8R-A. To determine the specificity of the anti-IL8R-A monoclonal antibodies generated, the antibodies were assayed for binding to IL8R-A expressed by transfected cells and were also assayed for binding to a member of the IL8R-BH class of compounds, IL8R-B, expressed by transfected cells. The anti-IL8R-A monoclonal antibodies exhibited specific binding to transfected cells expressing IL8R-A and no binding to transfected cells expressing IL8R-B. Blocking and non-blocking monoclonal antibodies were identified and their binding sites were mapped to the N-terminal region of IL8R-A. Details are provided below.

Generation of transfected cells expressing IL8R-A and transfected cells expressing IL8R-B Human 293 cells were co-transfected with pRK5B.il8r1.1 containing DNA encoding the type A IL-8 receptor (Holmes et al., supra) or pRK5.8rr27-1.1 containing DNA encoding the type B IL-8 receptor (Lee et al., *J. Biol. Chem.*, 267: 16283–16287 (1992)) and with pSVENeoBal6 (Seeburg et al., *Nature*, 312: 71–75 (1984)) plasmids in a 10:1 molar ratio, using a $CaPO_4$ transfection protocol. Gorman in *DNA Cloning: A Practical Approach*, ed., Glover, D. M. (IRL: Oxford, 1985), Vol. 2, pp. 143–165. Cultures were placed under 800 μg/ml G418 (Gibco) selection in F12/DMEM (50:50) medium containing 10% fetal calf serum, 2 mM L-glutamine, 100 units/ml Penicillin G, and 100 μg/ml streptomycin sulfate. Forty G418-resistant clonal lines were isolated from the pRK5B.il8r1.1 transfection. The forty G418-resistant clones were assayed for the ability to bind $1^{125}$I-IL-8 (Lee et al., supra.) One $^{125}$I-IL-8-binding cell line, 293-71, was selected for use in antibody production and antibody-binding experiments. Thirty G418-resistant clonal lines were isolated from the pRK5.8rr.27-1.1 transfection. The thirty G418-resistant clones were assayed for the ability to bind $^{125}$I-IL-8 (Lee et al., supra.) One $^{125}$I-IL-8-binding cell line, 293-27, was selected for further study.

Synthesis of IL8R-A and IL8R-B peptides

Peptides were synthesized via solid-phase methodology (Barany and Merrifield, in "The Peptides," 2: 1–284, Gross and Meienhofer, eds, (Academic Press: New York, 1980)) on either an ABI model 430 peptide synthesizer using tert-butyloxycarbonyl (t-BOC) chemistry or a Milligen model 9050 and ABI model 431 peptide synthesizer using fluorenylmethyloxycarbonyl (FMOC) chemistry. Crude peptides were purified by HPLC and analyzed via mass spectrometry. Peptides were conjugated to soybean trypsin inhibitor using m-maleimidobenzoyl-N-hydroxysulfosuccinimide ester (Sulfo-MBS) (Pierce Co., Rockford, Ill.).

Generation of hybridoma cell lines

BALB/c mice were immunized intraperitoneally with 10 μg of synthetic peptides covering various portions of extracellular domains of IL8R-A conjugated to horse serum albumin or $106^6$ cells/100 μl of transfected 293-71 cells, suspended in monophosphoryl lipid A/-trehalose dicorynomycolate (MPL/TDM) (Ribi Immunochem. Research Inc., Hamilton, Mont.), and boosted nine times with the same amount of peptides or 16 times with transfected cells. Three days after the final boost with the antigen, spleen cells were fused with mouse myeloma P3X63Ag8U.1 (Yelton et al., *Curr. Top. Microbiol. Immunol.*, 81: 1–7 (1978)), a nonsecreting clone of the myeloma P3X63Ag8 (Kohler and Milstein, *Nature*, 256: 495 (1975)) using 35% polyethylene glycol as described by Laskov et al., *Cell. Immunol.*, 55: 251–264 (1980). Ten days after the fusion, culture supernatant was screened for the presence of monoclonal antibodies to IL-8 type A receptor by ELISA or FACS.

ELISA analysis

Nunc ™ brand 96-well immunoplates (Flow Lab, McLean, Va.) were coated with 50 μl/well of 2 μg/mL peptide in phosphate buffered saline (PBS) overnight at 4° C. The remaining steps were carried out at room temperature as described by Kim et al., *J. Imm. Methods.*, 156: 9 (1992). The isotypes of monoclonal antibodies were determined by coating the plates with IL-8 type A receptor peptides overnight, blocked with 0.2% bovine serum albumin (BSA), incubated with culture supernatants followed by the addition of a predetermined amount of isotype-specific alkaline phosphate-conjugated goat anti-mouse Ig (Fisher Biotech, Pittsburgh, Pa.). The level of conjugated antibodies that bound to the plate was determined by the addition of p-nitrophenyl phosphate substrate in carbonate buffer plus 1 mM of $MgCl_2$ (Sigma 104 phosphate substrate, Sigma, St. Louis, Mo.). The color reaction was measured at 405 nm with an ELISA plate reader (Titertrek multiscan, Flow Lab, McLean, Va.).

FACS analysis

Human neutrophils were prepared by using Mono-Poly Resolving Medium (M-PRM) (Flow Lab., McLean Va.) according to the vendor's directions. Human neutrophils or transfected cells were washed twice in the cell sorter buffer (CSB, PBS-containing 1% FCS and 0.02% $NAN_3$) and recovered from each wash by centrifugation at 300×g for 5 minutes. Twenty-five μl of cells ($4 \times 10^6$ cells/ml) were added into the wells of a 96-well U-bottom microtiter plate, mixed with 100 μl of culture supernatant or purified monoclonal antibodies, and incubated for 30 min. on ice. Cells were then washed twice in CSB and incubated with 100 μl of FITC-conjugated goat-anti-mouse IgG antibodies for 30 min. at 4° C. Cells were washed twice in CSB and resuspended in 150 μl of CSB and analyzed by FAC-Scan ™ analysis.

IL-8 binding assays $^{125}$I-IL-8 receptor binding assays were conducted as follows. Recombinant human IL-8 (rHuIL-8) was expressed in *E. coli*, purified and labelled with $^{125}$I using lactoperoxidase as described in Hébert et al., supra. 50 μl of human neutrophils or transfected cells ($4 \times 10^6$ cells/ml) suspended in HBSS medium containing 0.5% BSA and 25 mM HEPES buffer were incubated for one hour at 4° C. with 50 μl aliquots of various mAb concentrations (0,015–50 μg/ml) or 50 μl of mAbs plus various concentrations of MGSA prepared as described by Horuk et al., *J. Biol. Chem.*, 268: 541 (1993). Cells were washed twice in the medium and resuspended at a concentration of $1 \times 10^6$ cells/ml. 100 μl of the cell suspension were incubated with 100 μl of $^{125}$I-IL-8 (128 μCi/ μg) for 1 hour at 4° C. The unbound $^{125}$I-IL-8 was removed by centrifuging the mixture in 0.5 ml of PBS containing 20% sucrose and 0.5% BSA at 1,500 rpm for 5 minutes. The $^{125}$I-IL-8 bound to the cell pellets was counted using a gamma counter. The percentage of $^{125}$I-IL-8 binding inhibition was calculated with the quotient formed by division of the amount of $^{125}$I-IL-8 radioactivity specifically binding to cells in the presence of monoclonal antibodies (mAbs) with the total amount of $^{125}$I-IL-8 radioactivity specifically binding no cells in the absence of mAbs. $^{125}$I-IL-8 specific binding amounts were determined by subtracting the amount of $^{125}$I-IL-8 non-specific binding from the total amount of $^{125}$I-IL-8 binding. The amount of $^{125}$I-IL-8 non-specific binding was determined by measuring $^{125}$I-IL-8 radioactivity bound in the presence of 0.4 μM IL-8. The level of non-specific $^{125}$I-IL-8 binding was approximately 10% of the total $^{125}$I-IL-8 binding.

Mutagenesis of IL8R-A

Mutants were prepared by the method of Kunkel et al., *Methods Enzymol.*, 154: 367–382 (1987) using the dut- ung- strain of *E. coli* CJ236 and a pUC-derived vector containing a cDNA insert coding for the IL-8 receptor A obtained from pRK5B.IL8r1.1. Holmes et al., supra. After verification of the mutant DNA sequence with the Sequenase ™ version 2.0 kit (U.S. Biochemical Corp.), the mutated plasmid preparations were purified with the Qiagen ™ plasmid maxi kit (Qiagen Inc., Chatsworth, Calif.) and used to transfect human fetal kidney 293 cells by the calcium phosphate precipitate method. The cell cultures were incubated for seven hours in the presence of sham precipitate or of mutant or wild-type DNA precipitate (10 μg DNA/100 mm dish). The precipitate was then removed and the cells were cultured for an additional 17 hours prior to fluorescence-activated cell sorter (FACS) analysis.

General characterization of MAbs

For generation of monoclonal antibodies to IL8R-A, mice were immunized with (1) synthetic peptides corresponding to various extracellular domains of IL8R-A or (2) stably transfected cells expressing IL8R-A.

Figure 7:
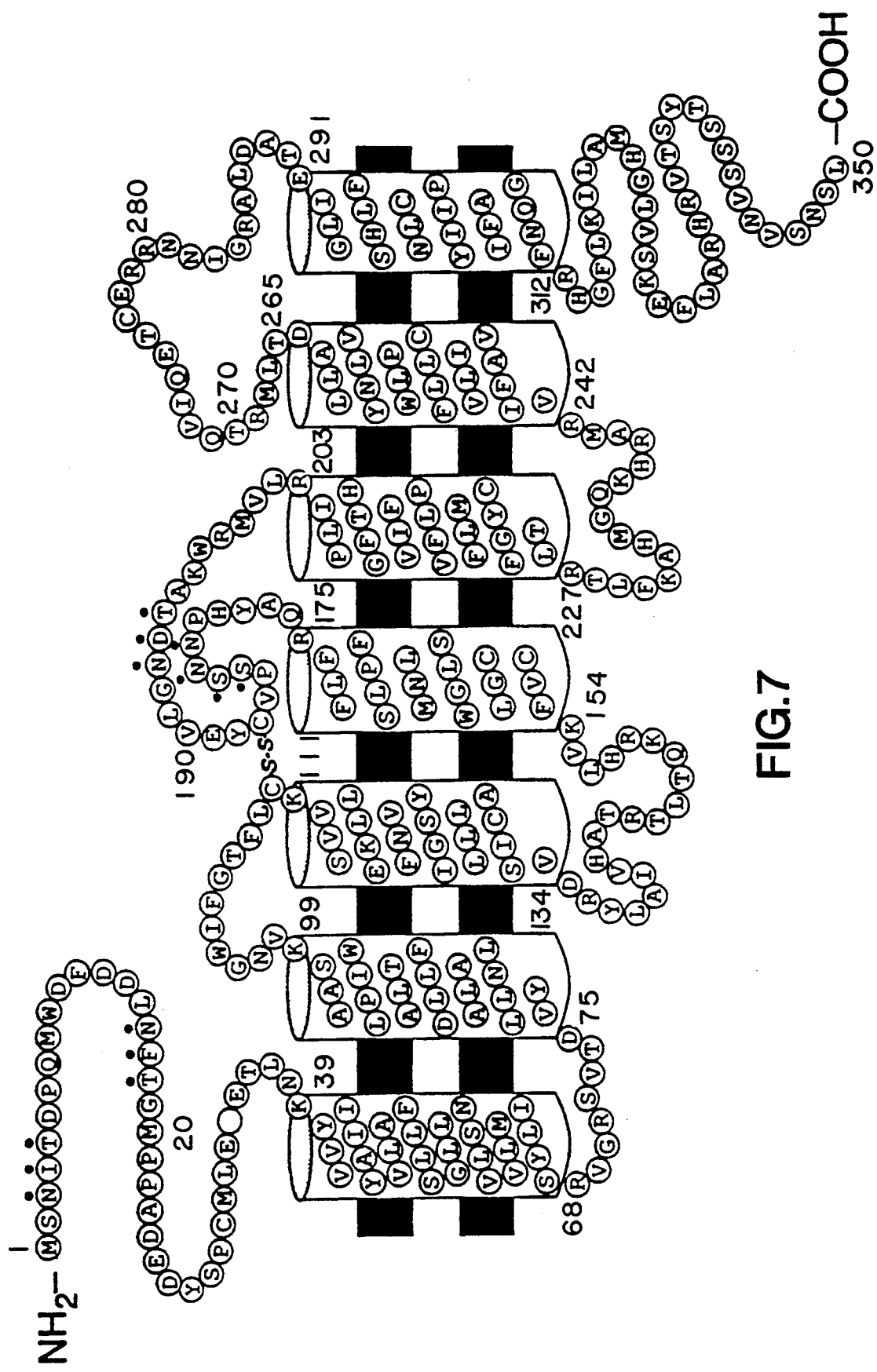
FIG. 7 depicts the structure of the human IL-8 receptor A. Each putative N-linked glycosylation site is identified with dots over the amino acids forming the site. Synthetic peptides consisting of amino acids 2-19, 12-31, 99-110, 176-187, 187-203, 265-277, and 277-291 of the extracellular domain of the IL8R-A receptor were made for use in the characterization of the IL8R-A receptor and the IL8R-B receptor and for use in the production and characterization of antibodies.

For the first approach, eight peptides were synthesized covering the extracellular domains of IL8R-A: residues 2-19 and 12-31 located within the N-terminal portion of IL8R-A, 99-110 within the first loop, 176-186 and 187-203 within the second loop, and 265-277 and 277-291 within the third loop as shown in FIG. 7. All these peptides induced high-titer antibodies to each peptide in mice. However, only peptide 2-19 produced polyclonal antibodies that were able to recognize human neutrophils as well as 293 transfected cells expressing IL8R-A. The mice immunized with peptide 2-19 were used to generate 36 strong monoclonal antibodies to peptide 2-19. Surprisingly, only two monoclonal antibodies (4C8 and 6E9) out of these 36 monoclonal antibodies were able to recognize IL8R-A on 293 transfected cells.

In a second approach, mice were immunized with 293 cells stably transfected with IL8R-A (293-71). Positive antibody titers were detected only after the 16th immunization. Among the 1152 hybridomas generated with these mice, 60 hybridomas were found to secrete monoclonal antibodies recognizing IL8R-A on 293-71 cells, as determined by FACS. Two out of 60 monoclonal antibodies, 2A4 (ATCC Accession No. HB 11377) and 9H1 (ATCC Accession No. HB 11376), were able to inhibit the binding of $^{125}$I-IL-8 to its receptors. Four monoclonal antibodies, 4C8, 6E9, 2A4, and 9H1, were selected for further characterization. All of these monoclonal antibodies secrete IgG1 and were able to stain human neutrophils and transfected 293-71 cells but not 293 cells, as determined by FACS analysis (Table 2). Thus, it was concluded that all of these monoclonal antibodies are capable of recognizing native IL8R-A.

TABLE 2

General Characteristics of Anti-IL8R-A mAbs

| Mab | Immunogen | Isotype | 293* | 293-71* | Human Neutrophil* | Kd (nM) |
|-----|-----------|---------|------|---------|-------------------|---------|
| 4C8 | Peptide 2-19 | IgG1 | − | + | + | 3.26 |
| 6E9 | Peptide 2-19 | IgG1 | − | + | + | 17.25 |
| 2A4 | 293-71 | IgG1 | − | + | + | 0.44 |
| 9H1 | 293-71 | IgG1 | − | + | + | 0.088 |

*Determined by FACS analysis

Cross reactivities to other related receptors.

Figure 8A:
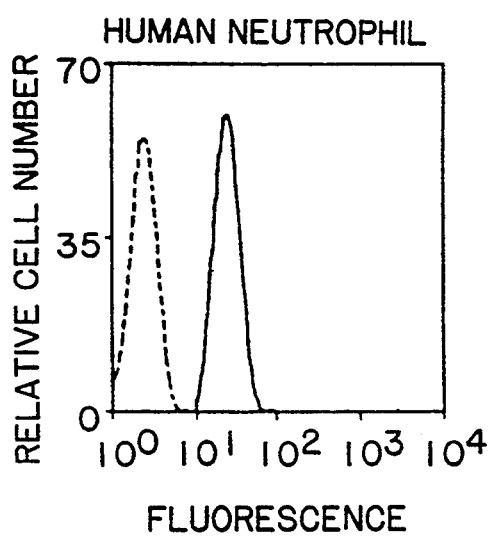
FIG. 8a–8d discloses the binding of monoclonal antibody 2A4 (ATCC Accession No. HB 11377) to human neutrophils (FIG. 8a), transfected 293 cells expressing IL8R-B (293-27) (FIG. 8b), transfected 293 cells expressing IL8R-A (293-71) (FIG. 8c), and untransfected 293 cells (FIG. 8d). Cells were incubated with 100 µl of culture supernatant or purified mAbs and then incubated with FITC-conjugated goat anti-mouse IgG. The solid lines depict the distribution of fluorescence detected in cells incubated with 2A4 and the dashed lines depict negative controls (cells incubated without antibody).
Figure 8B:
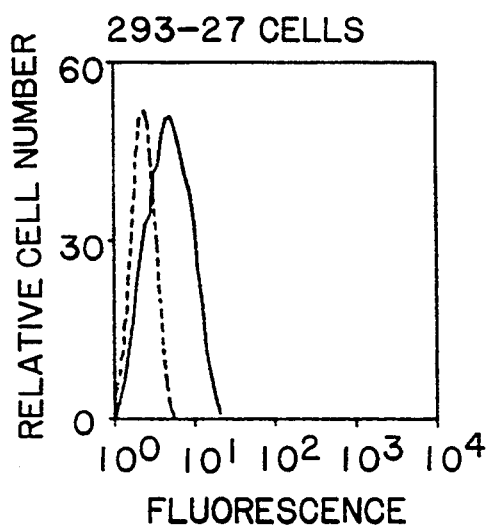
Figure 8C:
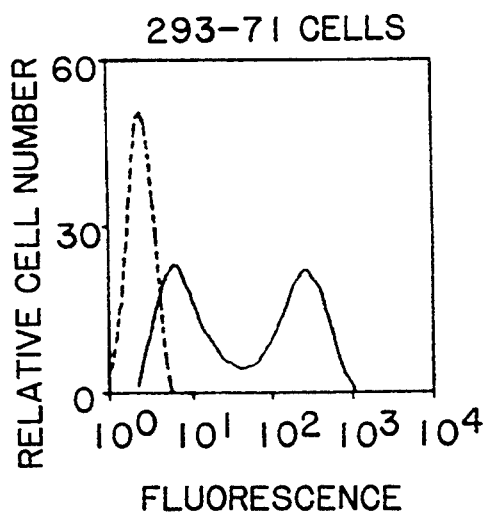
Figure 8D:
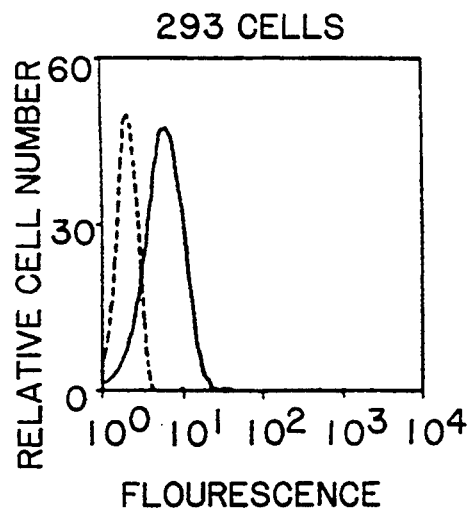

It has been shown that IL-8 specific receptor, IL8R-A, shares 77% amino acid identity with IL8R-B, the common IL-8/MGSA receptor. For determining whether monoclonal antibodies generated to IL8R-A could recognize IL8R-B, 293 cells transfected with IL8R-B (293-27) were stained and analyzed by FACS (FIG. 8a–d). FIG. 8a shows monoclonal antibody 2A4 binding to human neutrophils. FIG. 8b shows 2A4 binding to 293-27 cells. FIG. 8c shows 2A4 binding to 293-71 cells. FIG. 8d shows 2A4 binding to untransfected 293 cells. Monoclonal antibodies 4C8, 6E9, and 9H1 gave similar staining profiles. Thus, all four monoclonal antibodies stained the transfected 293 cells bearing IL8R-A (293-71) but not the IL8R-B transfected cells (293-27). The inability of these monoclonal antibodies to bind to 293 cells expressing IL8R-B was not due to the lack of receptor expression, since the same level of $^{125}$I-IL-8 binding was detected with IL8R-A expressing cells and IL8R-B expressing cells.

Inhibition of IL-8 binding to IL8R-A

The ability of the four monoclonal antibodies 4C8, 6E9, 2A4 and 9H1 to inhibit the binding of IL-8 to IL8R-A was characterized by determining the effect of the monoclonal antibodies on the binding of $^{125}$I-IL-8 to the transfected 293-71 cells expressing IL8R-A. At a concentration of 63 pM (0.1 μg/ml), monoclonal antibodies 2A4 and 9H1 each blocked approximately 50% of $^{125}$I-IL-8 binding to the 293-71 cells (FIG. 9a); monoclonal antibodies 4C8 and 6E9 showed a very minimal effect. Monoclonal antibody 4C8 at the highest concentration of antibody (10 μg/ml) produced approximately 20% inhibition of 2I-IL-8 binding to the 293-71 cell, while monoclonal antibody 6E9 had no effect. Therefore, it was concluded that monoclonal antibodies 2A4 and 9H1 are blocking antibodies and monoclonal antibodies 4C8 and 6E9 are nonblocking antibodies.

Figure 9A:
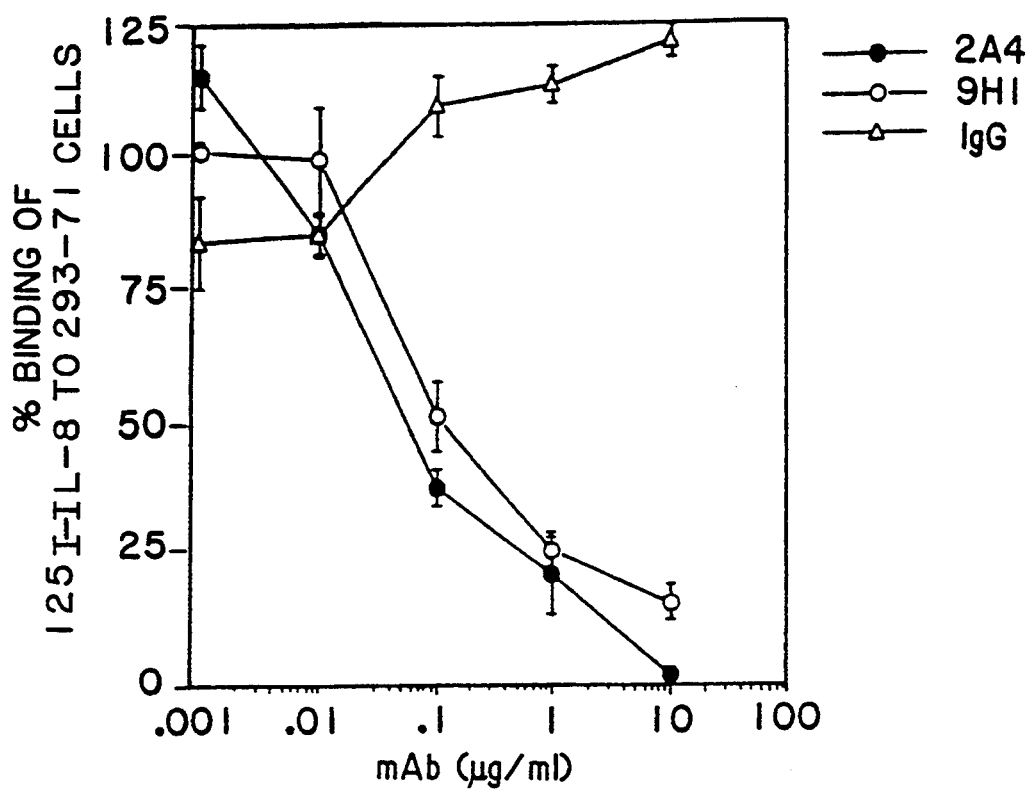
FIGS. 9a–9b shows the inhibition of $^{125}$I-labeled IL-8 binding to transfected 293 cells expressing IL8R-A (293-71) and to human neutrophils by mAbs 2A4 (filled circles), 9H1 (ATCC Accession No. HB 11376) (open circles), IgG (open triangles), and, in FIG. 9b, no antibody (filled squares). The experiments using 293-71 cells were carried out in the presence of various concentrations of 2A4, 9H1 and IgG (FIG. 9a). The experiments using human neutrophils were carried out in the presence of various concentrations of MGSA and 10 µg/ml of 2A4, 9H1 or IgG (FIG. 9b).
Figure 9B:
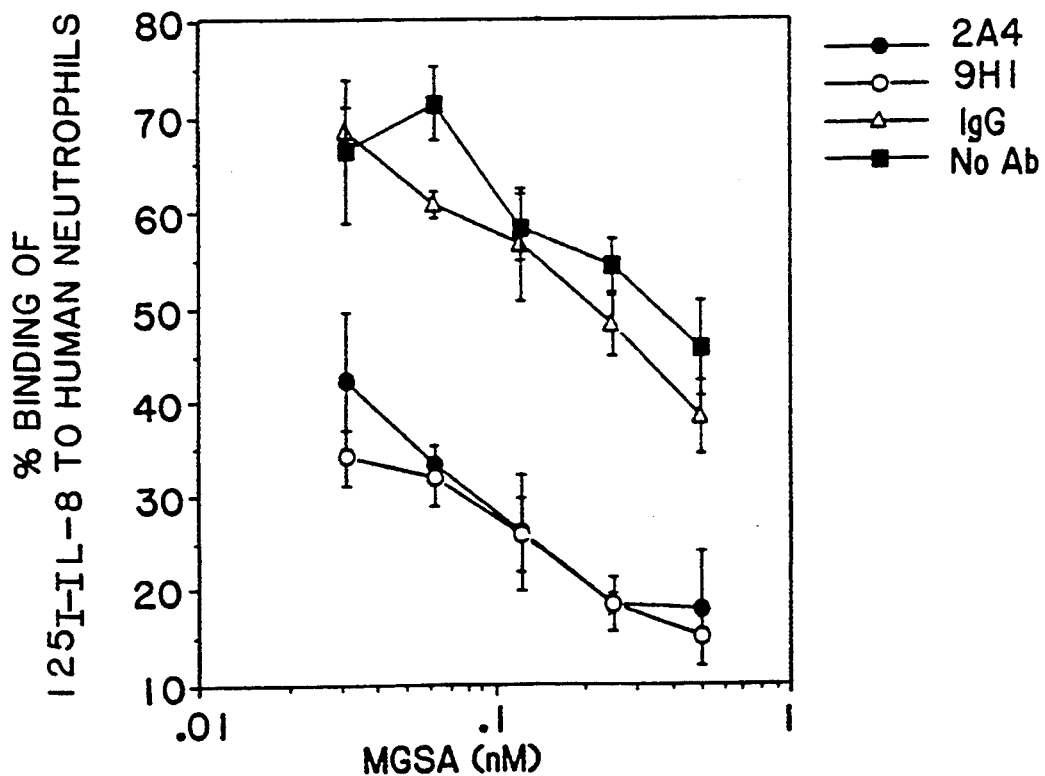

The ability of monoclonal antibodies 2A4 and 9H1 to block IL-8 binding to human neutrophils in the presence of various concentrations of MGSA (known to bind to IL8R-B) was determined. The addition of 300 pM MGSA inhibited approximately 50% of IL-8 binding to human neutrophils. Since human neutrophils express IL8R-A and IL8R-B at a 1-to-1 ratio, it was concluded that at a concentration of 300 pM, MGSA would block most of the IL-8 binding to IL8R-B. In the presence of 300 pM MGSA, monoclonal antibodies 2A4 and 9H1 could block up to 80% of the IL-8 binding to human neutrophils while control monoclonal antibody showed no further inhibition than that due to MGSA (FIG. 9b). Thus, it was concluded that monoclonal antibodies 2A4 and 9H1 are potent inhibitors of IL8 binding to IL8R-A on human neutrophils. FIG. 9a shows that monoclonal antibody 2A4 appears to be a more efficient blocking antibody than monoclonal antibody 9H1.

Mapping of MAb recognition sites on IL8R-A

Figure 10A:
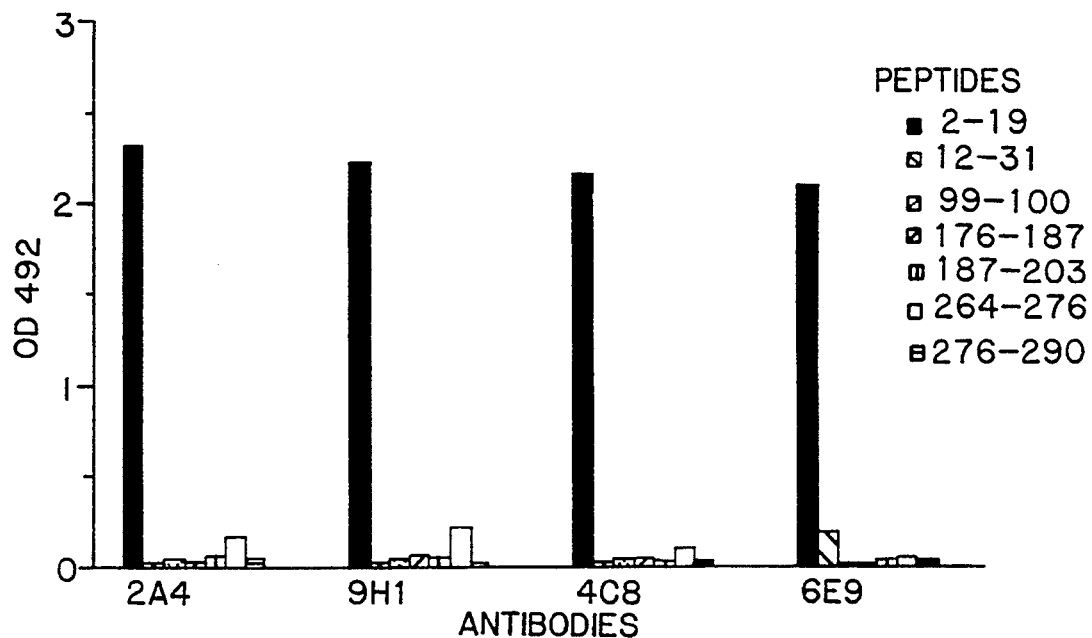
FIGS. 10a–10b shows the binding of monoclonal antibodies 2A4, 9H1, 4C8, 6E9, and an IgG1 control to various synthetic peptides as determined by ELISA. ELISA plates were coated with 2 µg/ml of peptides. Experiments were done in triplicate.

The epitopes recognized by these monoclonal antibodies were mapped by ELISA determination of the binding of these antibodies to synthetic peptides (FIG. 10a–b) and by FACS determination of the binding of these antibodies to alanine mutants of IL8R-A (Table 3). Surprisingly, both blocking and nonblocking monoclonal antibodies bound to the N-terminal peptide consisting of amino acids 2-19 of IL8R-A but not to other peptides covering different portions of the extracellular loops of IL8R-A (FIG. 10a).

TABLE 3

Flow Cytometry Analysis of Antibodies with Cells Expressing Mutant IL-8 Type A Receptor

| Amino Acid Position | Change From-To | FACS | | | |
|---|---|---|---|---|---|
| | | 2A4 | 9H1 | 4C8 | 6E9 |
| 6 | D-A | − | − | + | + |
| 11 | D-A | ++ | ++ | + | + |
| 13-14 | DD-AA | ++ | ++ | + | ++ |
| 24-26 | DED-AAA | ++ | ++ | ++ | + |
| 293-71 | | ++ | ++ | ++ | ++ |

TABLE 3-continued

Flow Cytometry Analysis of Antibodies with Cells Expressing Mutant IL-8 Type A Receptor

| Amino Acid Position | Change From-To | FACS 2A4 | 9H1 | 4C8 | 6E9 |
|---|---|---|---|---|---|
| 293-Control | | − | − | − | − |

FACS Result Grade: − (mean FL channel 0–10), + (Mean FL channel 10–100), ++ (Mean FL channel 100–1000).
D (Aspartic acid), A (Alanine), E (Glutamic Acid), 293-71 (293 cells expressing IL8R-A).

Figure 10B:
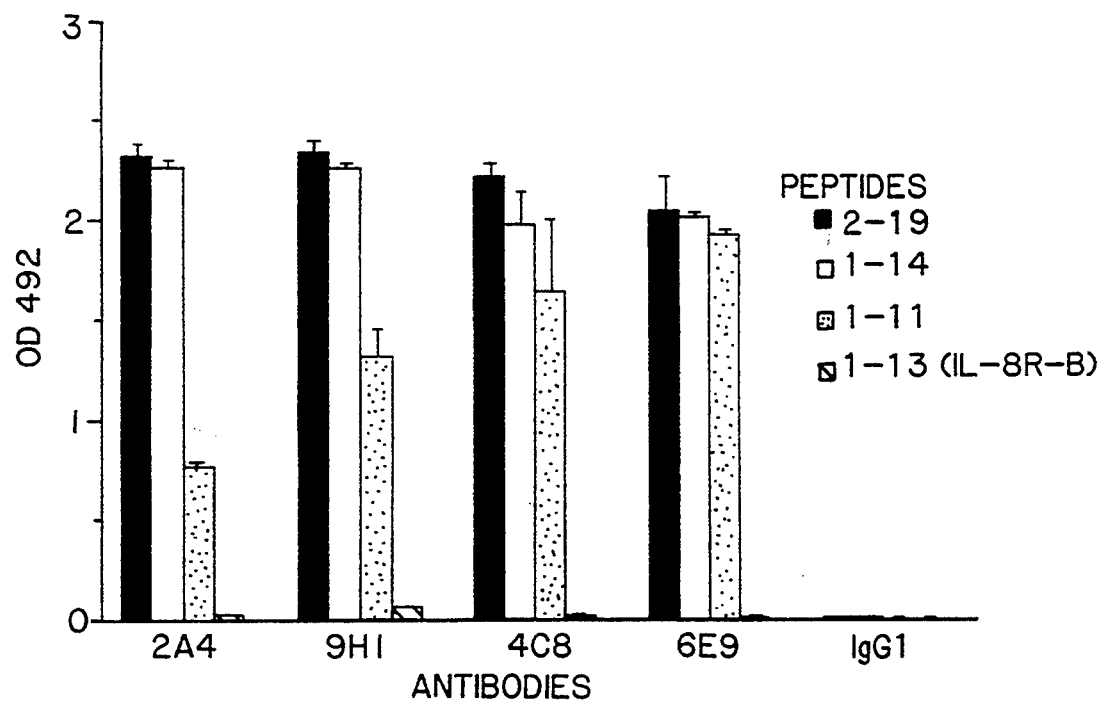

The binding of monoclonal antibodies to shorter peptides 1-11 and 1-14 is shown in FIG. 10b. All four monoclonal antibodies bound well to peptide 1-14. However, the binding of the blocking monoclonal antibodies, 2A4 and 9H1, to peptide 1-11 was only 22% and 60% of the binding to peptide 2-19, respectively. In contrast, the binding of the nonblocking monoclonal antibodies, 4C8 and 6E9, to peptide 1-11 was approximately 80% and 95% of the binding to peptide 2-19, respectively. From these results it was concluded that the epitopes of monoclonal antibodies 4C8 and 6E9 are localized within amino acids 2-11, while those of monoclonal antibodies 2A4 and 9H1 are localized within amino acids 2-14. The binding epitopes of these monoclonal antibodies were further characterized by FACS analysis of their binding to IL8R-A mutants (Table 3). Neither monoclonal antibody 2A4 nor 9H1 could bind to the IL8R-A mutant when the aspartic acid at position 6 was substituted with alanine, which indicates that Asp6 plays an important role in the binding of these blocking antibodies. This result further indicates that the conformation of the N-terminal end of IL8R plays a role in the binding of blocking monoclonal antibodies.

MAb binding affinities

The relative affinities of monoclonal antibodies to peptide 2-19 were determined by ELISA measurement of the antibody concentration required to give 50% of the maximum binding ($ED_{50}$) to this peptide as described by Van Heyningen, *Meth. Enzymol.*, 121: 472 (1986). The highest affinity for peptide 2-19 was shown with monoclonal antibody 4C8 followed by 9H1, 2A4 and 6E9 (Table 4). However, the cell-derived monoclonal antibodies (2A4 and 9H1) exhibited affinities for the native IL-8 type A receptor expressed on transfected 293-71 cells that are 7 to 196-fold greater than the affinities of the peptide-derived monoclonal antibodies (4C8 and 6E9) for IL8R-A expressed on 293-71 cells, as determined by Scatchard plot analysis (Table 4).

TABLE 4

| Affinities of mAbs to Peptide 2-19 and to IL8R-A | | |
|---|---|---|
| mAb | $ED_{50}$ (nM)[a] | $K_d$(nM)[b] |
| 4C8 | 0.044 | 3.26 |
| 6E9 | 0.563 | 17.0 |
| 2A4 | 0.281 | 0.44 |
| 9H1 | 0.125 | 0.088 |

[a] $ED_{50}$ was determined by the concentration of mAbs which produced 50% of the maximum binding to peptide 2-19 in ELISA.
[b] The affinities were determined by Scatchard plot analysis using competitive inhibition of $^{125}$I-mAb binding to native IL8R-A with various concentrations of unlabelled mAb.

Conclusion

The antibody response to different extracellular portions of IL8R-A was induced using several synthetic peptides as immunogens (FIG. 7). However, only the antibodies generated to N-terminal peptide, consisting of amino acid residues 2-19, bound to the stably transfected 293 cells and human neutrophils. Furthermore, polyclonal antibodies to transfected 293 cells bound only to peptide 2-19. These results suggest that the N-terminal amino acids may be the most immunogenic and hydrophilic.

The 4C8, 6E9, 2A4 and 9H1 monoclonal antibodies recognize IL8R-A but not IL8R-B, probably because these antibodies bind to the N-terminal residues of IL8R-A wherein the greatest dissimilarity exists between the two IL-8 receptors. The IL-8 receptors do not recognize IL-1, TNF-α, MCAF, fMLP, C5a, PAF, and LTB4 but do recognize two other members of the C-X-C family, namely, MGSA and NAP-2. Holmes et al., supra. A recent study shows that both receptors bind IL-8 equally well with a high affinity ($K_d=2$nM, Larsen et al. *Science*, 243: 1464 (1989)) but differ in their affinity to MGSA. IL8R-A has a low affinity to MGSA, while IL8R-B has a high affinity ($K_d=2$ nM).

Monoclonal antibodies 2A4 and 9H1 completely block the IL-8 binding to transfected 293 cells but block only 35%–40% of the IL-8 binding to human neutrophils. However, in the presence of a concentration of MGSA (0.3 nM) that inhibits 50% of IL-8 binding to human neutrophils, monoclonal antibodies 2A4 and 9H1 inhibit approximately 80% of IL-8 binding. Therefore, the blocking monoclonal antibodies interfere with the interaction between IL-8 and IL8R-A but not with the interaction between IL-8 and IL8R-B.

In contrast to the monoclonal antibodies generated by immunization with the transfected cells, monoclonal antibodies raised against the N-terminal peptide of IL8R-A did not block the interaction of IL-8 with its receptors even though they could compete for binding to IL8R-A as determined by the competitive binding assay. The inability of peptide monoclonal antibodies to effectively block the binding of IL-8 to its receptor is not due to the low affinity of these monoclonal antibodies. Among four monoclonal antibodies, 4C8 had the highest affinity to IL8R-A. This indicates that the tertiary structure of the N-terminal portion of IL8R-A plays a role in the generation of blocking monoclonal antibodies. Further, there are differences in the binding sites of the blocking and non-blocking monoclonal antibodies. The epitope of blocking monoclonal antibodies was mapped within residues 2-14 of the IL-8 type A receptor, whereas the epitope of the nonblocking monoclonal antibodies was mapped within residues 2-11 of IL8R-A.

The characterization of antibody binding to IL8R-A with various IL8R-A alanine mutants indicates that the aspartic acid at position 6 (D6) plays an important role in the binding of the blocking monoclonal antibodies, 2A4 and 9H1, but not in the binding of the non-blocking monoclonal antibodies, 4C8 and 6E9. This indicates that the aspartic acid at position 6 could be located at (or near to) the binding site of IL-8. It has been shown that positively charged IL-8 residues $E_4$, $L_5$, $R_6$ are essential for IL-8 binding to its receptors on human neutrophils by alanine-scanning mutagenesis (Hébert et al., *J. Biol. Chem.*, 266: 18989 (1991)) and synthesis of N-terminal truncated variants. Clark-Lewis et al., *J. Biol. Chem.*, 266: 23128 (1991). Thus, the negatively charged amino acid at position 6 in IL8R-A could directly interact with the positively charged amino acids, $E_4$, $L_5$, $R_6$ in IL-8.

The N-terminal portion and the second extracellular portion of IL8R-A appears to be highly glycosylated, especially within amino acids 2-19 and 181-195 of the receptor where there are five potential glycosylation sites (FIG. 7). However, all of the monoclonal antibodies, whether they were generated by immunization using synthetic peptides or transfected cells, bound to the peptide covering amino acids 2-19. This suggests that carbohydrates may not play an important role in the binding of these monoclonal antibodies. This conclusion was supported by a report (Stader et al., supra) that glycosylation does not appear to be required for ligand binding or functional coupling to G protein β-adrenergic receptor, even though the glycosylation plays a role in the expression of the receptors on the cell surface and in the trafficking of the receptor through the cell.

EXAMPLE 4

Generation of MAbs to IL8R-BH

Anti-IL8R-BH monoclonal antibodies were prepared by immunizing mice with stably transfected cells expressing an IL8R-BH. Although the IL-8 type B receptor (IL8R-B) is the particular IL8R-BH used herein, it will be appreciated that monoclonal antibodies against any IL8R-BH can be prepared according to the following method.

Generation of transfected cells expressing IL8R-A and transfected cells expressing IL8R-B Human 293 cell clone 293-27 expressing IL8R-B and human 293 cell clone 293-71 expressing IL8R-A were obtained as described in Example 3 above.

Synthesis of IL8R-A and IL8R-B peptides

Peptides were synthesized via solid-phase methodology (Barany and Merrifield, supra) on either an ABI model 430 peptide synthesizer using t-BOC chemistry or a Milligen model 9050 and ABI model peptide synthesizer 431 using FMOC chemistry. Crude peptides were purified by HPLC and analyzed via mass spectrometry.

Generation of hybridoma cell lines

BALB/c mice were immunized intraperitoneally with $10^6$ cells/100 μl of 293-27 cells suspended in MPL/TDM (Ribi Immunochem. Research Inc., Hamilton, Mont.) and boosted 16 times with the transfected cell suspension. Three days after the final boost with the antigen, spleen cells were fused with mouse myeloma P3X63Ag8U.1 (Yelton et al., supra), a non-secreting clone of the myeloma P3X63Ag8 (Kohler and Milstein, supra) using 35% polyethylene glycol as described by Laskov et al., supra. Ten days after the fusion, the culture supernatant was screened for the presence of monoclonal antibodies to IL-8 type B receptor by ELISA or FACS.

Preparation of fluorescein isothiocyanate (FITC) conjugated MAbs

Fluoresceinated (F-) mAbs were prepared according to the method described by Goding, *J. Immunol. Meth.*, 13: 215 (1976). MAbs dialyzed in 0.1M sodium carbonate buffer (pH 9.3) were incubated with fluorescein isothiocyanate (Sigma Chemical Co., St. Louis, Mo.) in dimethyl sulfoxide for 8 hours at 4° C. and then dialyzed in PBS overnight. The ratio of fluorescein to protein (F/P) was determined by measuring the absorbance at 495 run and 280 nm, respectively.

ELISA analysis

ELISA analysis of antibody binding to synthetic peptides was performed as described in Example 3 above.

FACS analysis

Human peripheral blood mononuclear cells and neutrophils were separated from red blood cells (RBCs) in blood samples by laying blood samples on Mono-Poly Resolving Medium (M-PRM) (Flow Lab, McLean, Va.) according to the vendor's instructions. For single colored FACS analysis of antibody binding to neutrophils, monocytes and lymphocytes, neutrophils or peripheral blood mononuclear cells were washed twice in the cell sorter buffer (CSB, PSB-containing 1% FCS and 0.02% NAN3) and recovered from each wash by centrifugation at 300×g for 5 minutes. $10^6$ neutrophils or peripheral blood mononuclear cells were added into the wells of a 96-well U-bottom microtiter plate and incubated for 30 minutes on ice with 100 μl of F-mAbs to IL8R-A or IL8R-B, washed twice in CSB, resuspended in 150 μl of CSB and analyzed by FACSscan (Becton Dickinson, Mountainview, Calif.). FITC conjugated mAb 9H1.5.1 (F-9H1) and 10H2.12.1 (F-10H2) were used for the detection of IL8R-A and IL8R-B, respectively.

For double colored FACS analysis of antibody binding to lymphocyte cell subpopulations, peripheral blood mononuclear cells were washed twice in CSB and recovered from each wash by centrifugation at 300×g for 5 minutes. $10^6$ cells were added into the wells of a 96-well microtiter plate and incubated for 30 minutes on ice with 20 μl of a phycoerythrin (PE-) conjugated mAb for detection of a specific surface antigen and 100 μl of F-mAbs to IL8R-A or IL8R-B, washed twice in the cell sorter buffer (CSB) (PBS containing 1% FCS and 0.02% NaN3), resuspended in 150 μl of CSB and analyzed by FACScan (Becton Dickinson, Mountainview, Calif.). Phycoerythrin conjugated (PE-) mAbs such as anti-Leu 2a (anti-CD18), anti-Leu 3a (anti-CD4), anti-Leu M3 (anti-CD14), anti-Leu 16 (anti-CD20) and anti-Leu 19 (anti-CD56) were obtained from Becton Dickinson (Mountainview, Calif.). FITC conjugated mAb 9H1.5.1 (F-9H1) and 10H2.12.1 (F-10H2) were used for the detection of IL8R-A and IL8R-B, respectively.

IL-8 binding assays $^{125}$I-IL-8 receptor binding assays were conducted as described in Example 3 above.

General characterization of MAbs

For generation of monoclonal antibodies to IL8R-B, mice were immunized with 293 cells stably transfected with IL8R-B (293-27). Positive antibody titers were detected only after the 16th immunization. Among the 1008 hybridomas generated with these mice, 127 hybridomas were found to secrete monoclonal antibodies recognizing IL8R-B on 293-27 cells, as determined by FACS. Two out of the 127 monoclonal antibodies, 4D1 (ATCC Accession No. HB 11495) and 10H2 (ATCC Accession No. HB 11494), were able to inhibit the binding of $^{125}$I-IL-8 to its receptors.

The 4D1 and 10H2 hybridomas were selected for further characterization. Both of these hybridomas secreted IgG2a immunoglobulins which were able to stain human neutrophils and 293-27 cells expressing IL8R-B but were not able to stain 293 cells, as determined by FACS analysis (Table 5 and FIG. 12b-c). Thus, it was concluded that the 4D1 and 10H2 monoclonal antibodies were capable of recognizing native IL8R-B.

TABLE 5

| | General Characteristics of Anti-IL8R-B mAbs | | | | |
| | | | FACS Analysis | | |
| Mab | Immunogen | Isotype | 293-27 | 293-71 | 293 | human neutrophil |
|---|---|---|---|---|---|---|
| 4D1 | 293-27 | IgG2a | + | − | − | + |

TABLE 5-continued

| | | | FACS Analysis | | | |
|---|---|---|---|---|---|---|
| Mab | Immunogen | Isotype | 293-27 | 293-71 | 293 | human neutrophil |
| 10H2 | 293-27 | IgG2a | + | − | − | + |

General Characteristics of Anti-IL8R-B mAbs

Cross reactivities to other related receptors

Figure 12A:
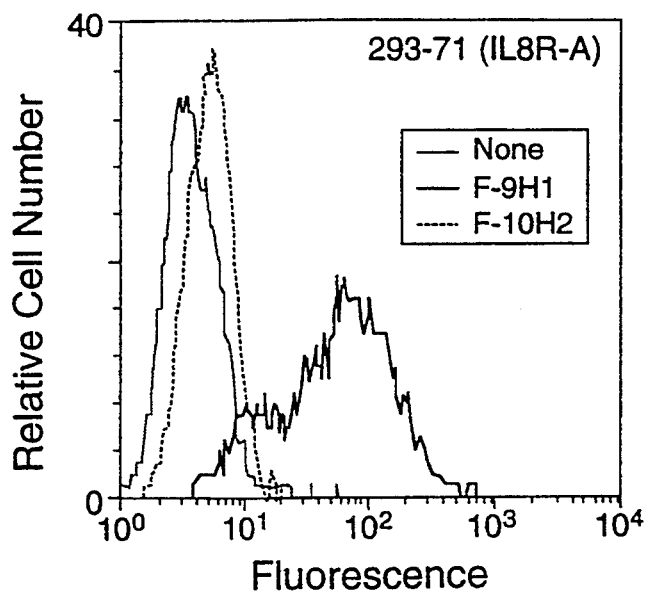
FIGS. 12a–12c discloses the binding of monoclonal antibodies 9H1 and 10H2 (ATCC Accession No. HB 11494) to transfected 293 cells expressing IL8R-A (293-71) (FIG. 12a), transfected 293 cells expressing IL8R-B (293-27) (FIG. 12b), and human neutrophils (FIG. 12c) as determined by FACS. Cells were incubated with 1 µl/ml of mAb and then incubated with FITC-conjugated goat anti-mouse IgG. The solid lines indicate fluorescence detected in cells incubated with 9H1, the dashed lines indicate fluorescence detected in cells incubated with 10H2, and the jagged lines indicate negative controls (cells incubated without antibody).
Figure 12B:
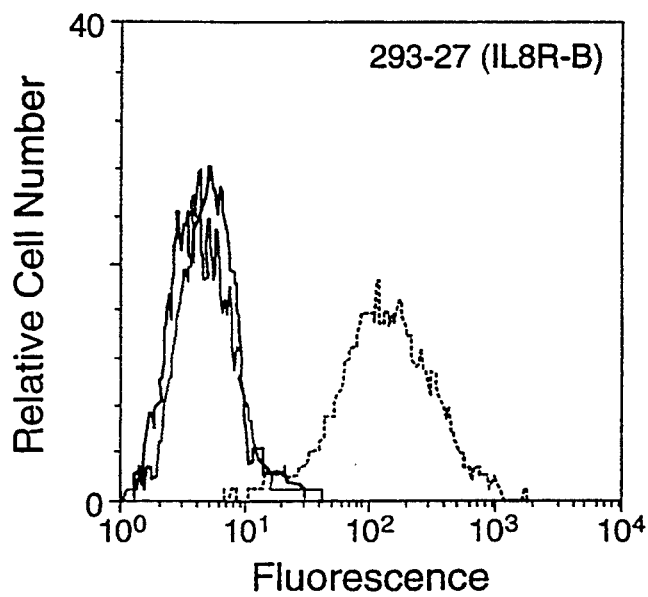
Figure 12C:
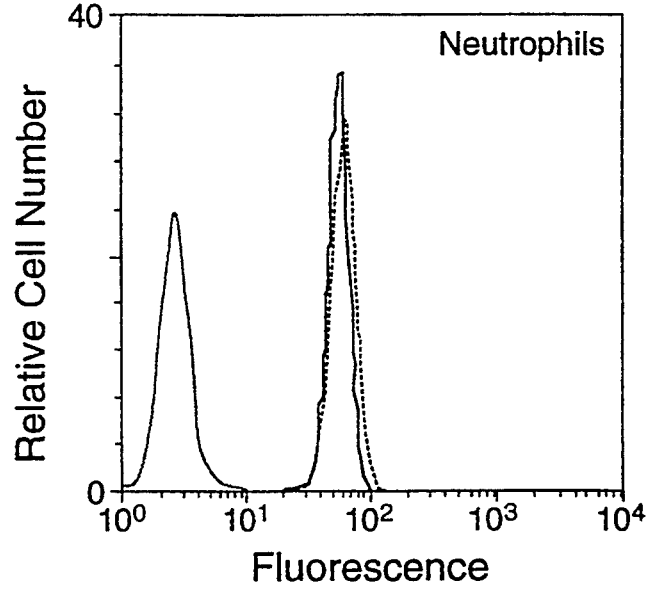

It has been shown that IL-8 specific receptor, IL8R-A, shares 77% amino acid identity with IL8R-B, the common IL-8/MGSA receptor. The above table shows that the two monoclonal antibodies generated against IL8R-B could not recognize IL8R-A. For determining this result 293-71, 293-27, human neutrophils, and untransfected 293 cells treated with the two antibodies were stained and analyzed by FACS. As shown in FIG. 12a–b and Table 5, these monoclonal antibodies stained the IL8R-B transfected cells bearing IL8R-B (293-27) but not the IL8R-A transfected cells (293-71). The inability of these monoclonal antibodies to bind to 293 cells expressing IL8R-A was not due to the lack of receptor expression since the same level of $^{125}$I-IL-8 binding was detected with IL8R-B expressing cells and IL8R-A expressing cells.

Inhibition of IL-8 binding to IL8R-B

Figure 13:
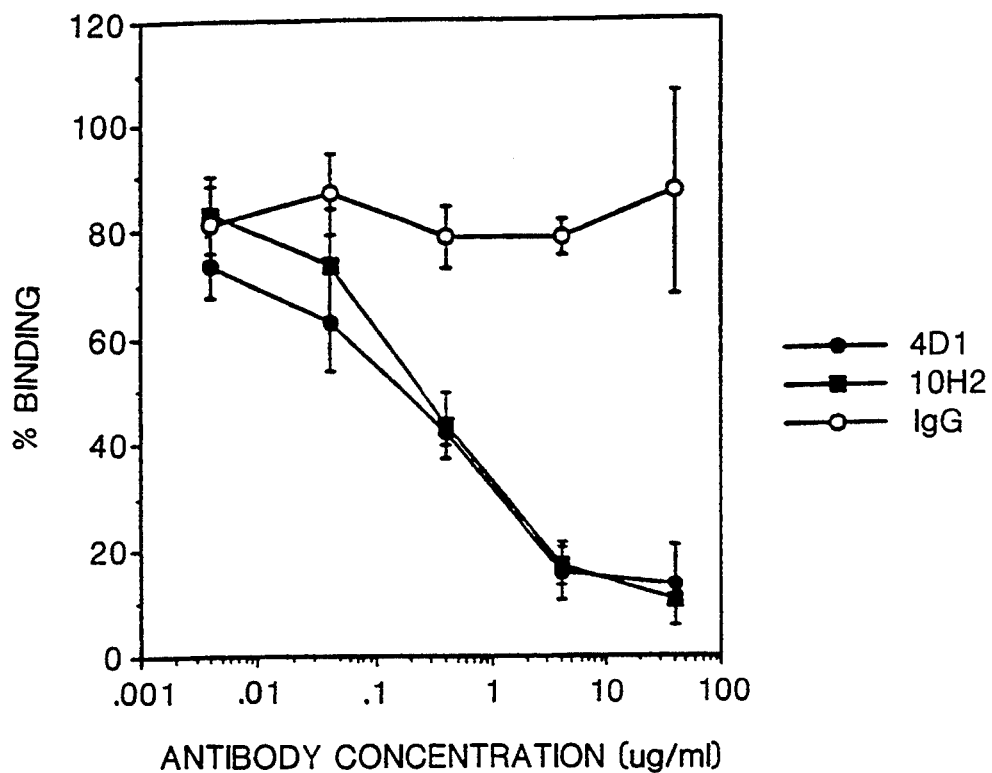
FIG. 13 shows the inhibition of $^{125}$I-labeled IL-8 binding to transfected 293 cells expressing IL8R-B (293-27) by various concentrations of 4D1 (ATCC Accession No. HB 11495) (filled circles), 10H2 (filled squares) and IgG (open circles).

The ability of the two monoclonal antibodies 4D1 and 10H2 to inhibit the binding of IL-8 to IL8R-B was characterized by determining the effect of the monoclonal antibodies on the binding of $^{125}$I-IL-8 to the transfected 293-27 cells expressing IL8R-B. At a concentration of 63 pM (0.1 μg/ml) monoclonal antibodies 4D1 and 10H2 each blocked approximately 50% of $^{125}$I-IL-8 binding to the 293-27 cells (FIG. 13). Therefore, it was concluded that monoclonal antibodies 4D1 and 10H2 are blocking antibodies.

Mapping of MAb recognition sites on IL8R-B

Figure 15:
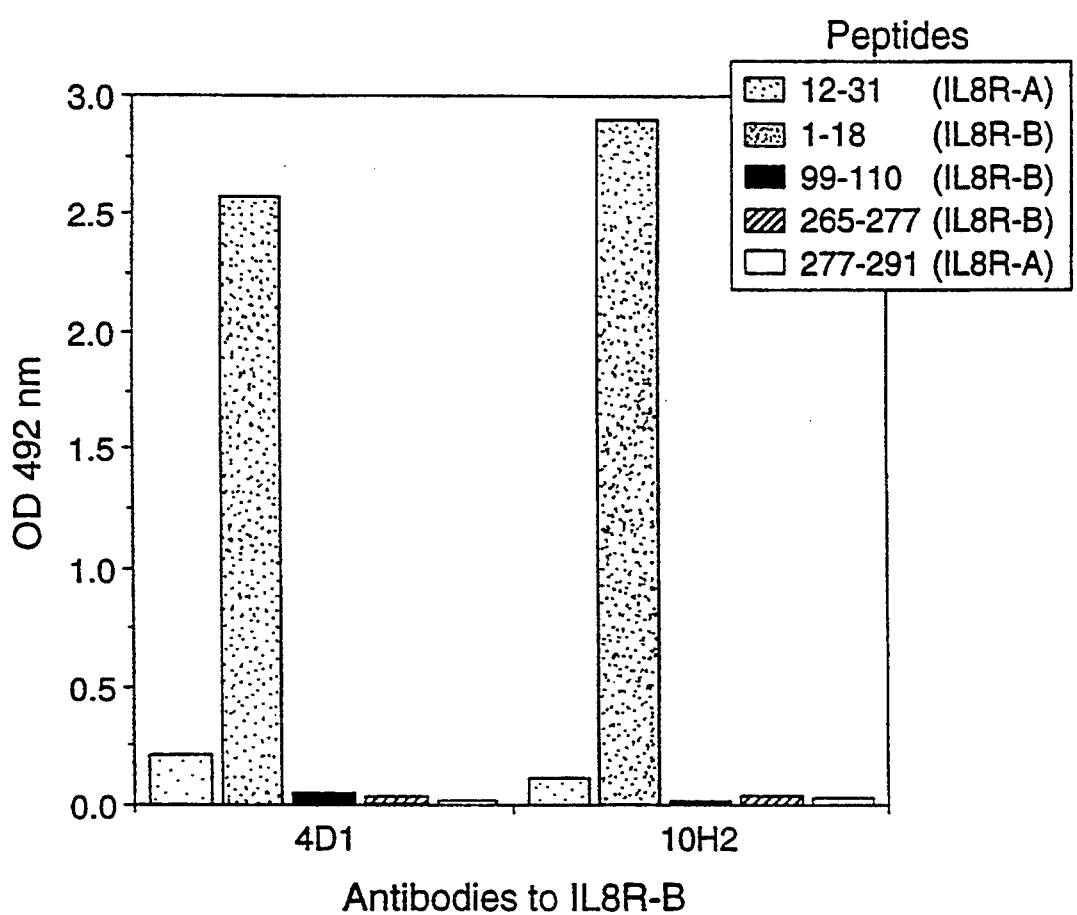
FIG. 15 shows the binding of monoclonal antibodies 4D1 and 10H2 to synthetic peptides representing various extracellular domains of IL8R-A and IL8R-B as determined by ELISA. ELISA plates were coated with 2 µg/ml of peptides. Experiments were done in triplicate.

The epitopes recognized by these monoclonal antibodies were mapped by ELISA analysis of the binding of these antibodies to synthetic peptides (FIG. 15). Peptides corresponding to amino acids 12-31 of IL8R-A, to amino acids 1-18 of IL8R-B, to amino acids 99-110 of IL8R-B, to amino acids 265-277 of IL8R-B, and to amino acids 277-291 of IL8R-A were synthesized. Peptides corresponding to amino acids 277-291 of IL8R-A were used to represent the third loop of the extracellular domain of IL8R-B. The amino acids 273-291 of IL8R-B differ from the amino acids 273-291 of IL8R-A by histidine residue in place of an asparagine residue at amino acid position 282 and an aspartic acid residue in place of a glycine residue at amino acid position 284. Surprisingly, both blocking monoclonal antibodies bound to the N-terminal peptide consisting of amino acids 1-18 of the IL-8 type B receptor, but not to other peptides covering different portions of the extracellular loops (FIG. 15) of IL8R-B. From these results, it was concluded that the epitopes of monoclonal antibodies 4D1 and 10H2 are localized within amino acids 1-18 at the N-terminus of the IL-8 type B receptor.

Figure 14:
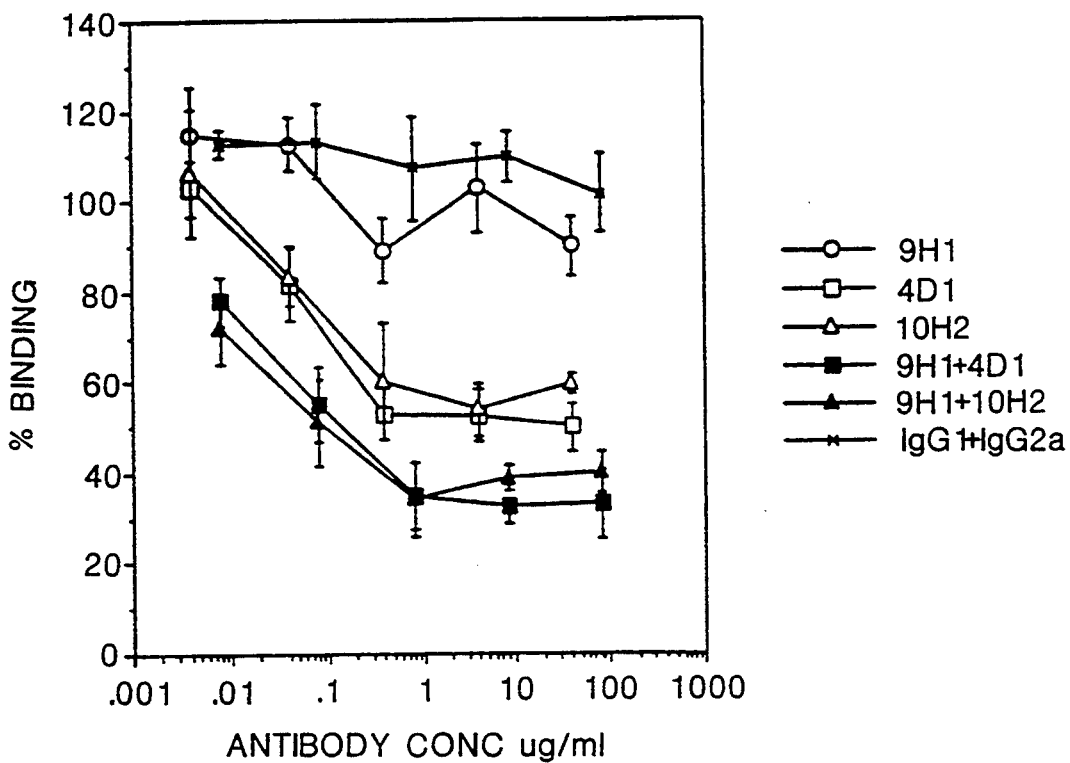
FIG. 14 shows the inhibition of $^{125}$I-labeled IL-8 binding to human neutrophils by various concentrations of 9H1 (open circles), 4D1 (open squares), 10H2 (open triangles), 9H1 plus 4D1 (filled squares), 9H1 plus 10H2 (filled triangles), and IgG1 plus IgG2a (X's).

Inhibition of IL-8 binding to human neutrophils with combinations of MAbs to IL8R-A and IL8R-B The ability of combinations of mAbs to IL8R-A and IL8R-B to inhibit IL-8 binding to human neutrophils was determined. At a total antibody concentration of 1 μg/ml, 9H1/4D1 and 9H1/10H2 combinations inhibited approximately 70% of IL-8 binding to human neutrophils (FIG. 14).

Detection of IL8R-A and IL8R-B on various human leukocytes

Figure 16A:
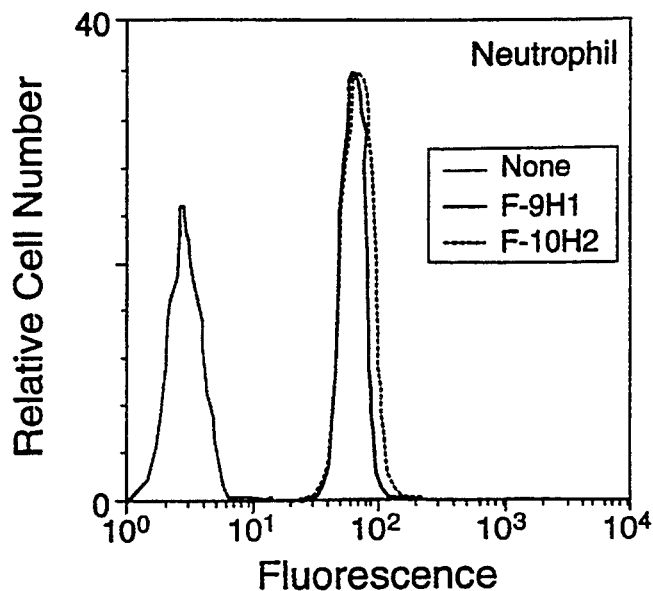
FIG. 16a–16c discloses the binding of FITC-conjugated monoclonal antibodies 9H1 (F-9H1) and 10H2 (F-10H2) to human neutrophils (FIG. 16a), monocytes (FIG. 16b), and lymphocytes (FIG. 16c) from a particular donor (donor no. 1) as determined by FACS. The solid lines indicate fluorescence detected in cells incubated with F-9H1, the dashed lines indicate fluorescence detected in cells incubated with F-10H2, and the jagged lines indicate negative controls (cells incubated without antibody).
Figure 16B:
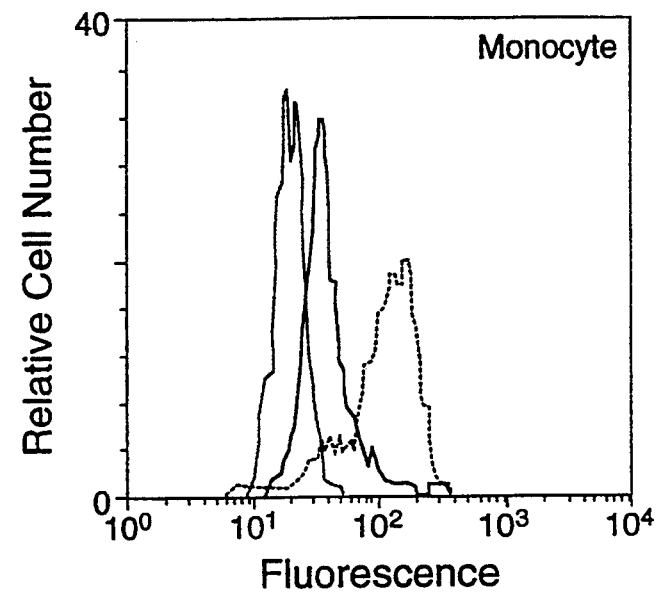
Figure 16C:
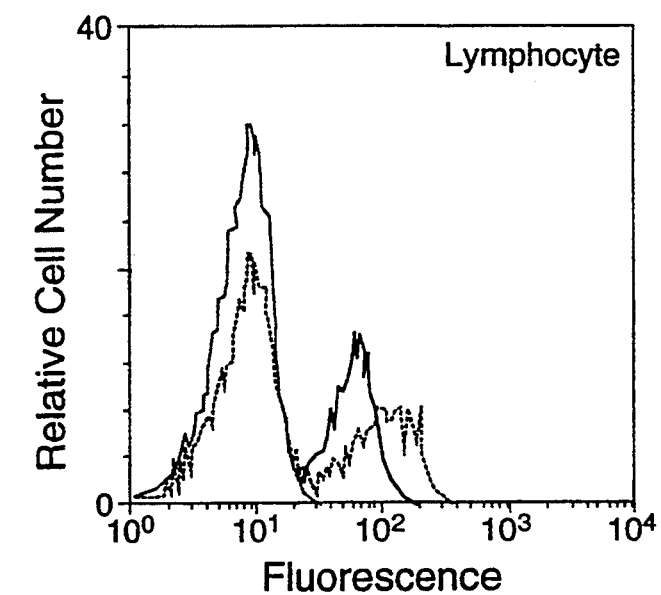
Figure 17A:
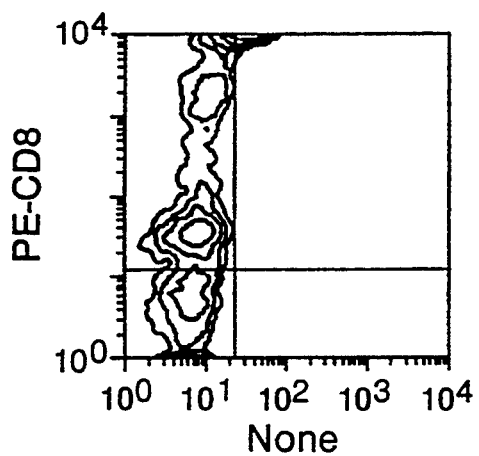
FIG. 17a–17f discloses the binding of F-9H1 to CD8+ suppressor T cells (FIG. 17b), the binding of F-10H2 to CD8+ suppressor T cells (FIG. 17c), the binding of F-9H1 to CD56+ NK cells (FIG. 17e), and the binding of F-10H2 to CD56+ NK cells (FIG. 17f) from donor No. 1. The y axis of FIG. 17a–c depicts the presence of CD8+ cells detected by phycoerythrin-conjugated anti-Leu 2a (CD8) monoclonal antibody (PE-CD8). The y axis of FIG. 17d–f depicts the presence of CD56+ cells detected by phycoerythrin-conjugated anti-Leu 19 (CD56) monoclonal antibody (PE-CD56). The x axis of FIG. 17b and 17e depicts the presence of IL8R-A+ cells detected by F-9H1. The x axis of FIG. 17c and 17f depicts the presence of IL8R-B+ cells detected by F-10H2. CD8+ cells (FIG. 17a) and CD56+ cells (FIG. 17d) incubated without F-9H1 or F-10H2 served as negative controls.
Figure 17D:
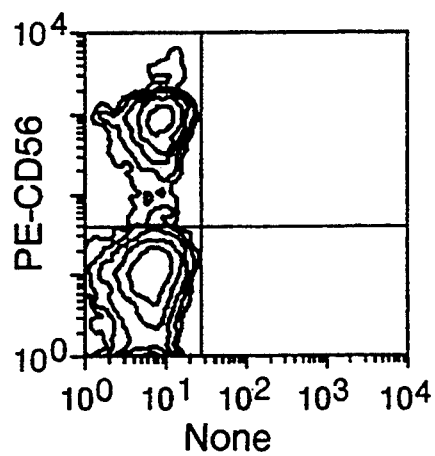
Figure 17B:
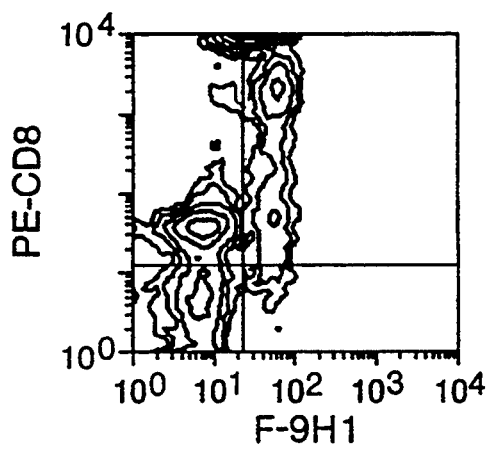
Figure 17E:
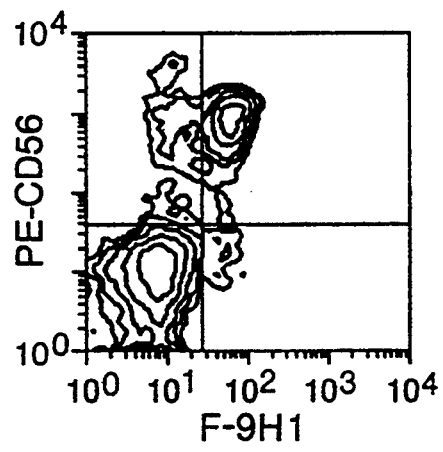
Figure 17C:
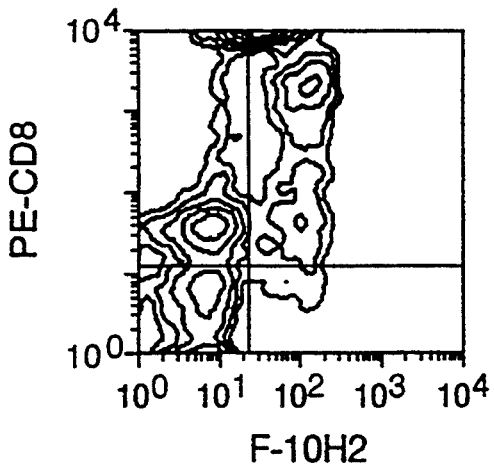
Figure 17F:
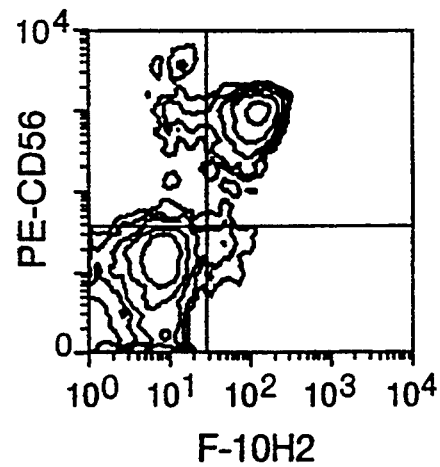

FACS analysis was used to determine the levels of IL8R-A and IL8R-B expression in human neutrophils, monocytes and lymphocytes. F-9H1 and F-10H2 were used in the FACS staining of the various leukocyte cell populations. The F/P ratios of fluoresceinated 9H1 and 10H2 were 6.5 and 5.0, respectively. A wide variation in IL8R expression was found among the individual donors. Table 6 and FIG. 16a–c show that neutrophils expressed the highest level of IL8R among blood leukocytes and that the ratio of the expression level of IL8R-A and IL8R-B on neutrophils, as determined by mean fluorescence unit, is in the range of 0.84-1.65. Table 6 and FIG. 16b also show that monocytes expressed both IL8R-A and IL8R-B and that the expression level of IL8R-B is higher than the expression level of IL8R-A in monocytes. Table 6 and FIG. 16c further show that approximately 5–25% of lymphocytes express IL8R and that the IL8R-B expression level is higher than the IL8R-A expression level in lymphocytes.

TABLE 6

The level of expression IL8R-A and IL8R-B on lymphocytes, monocytes and neutrophils.

| | IL8R-A* | IL8R-B* | IL8R-B/IL8R-A |
|---|---|---|---|
| Donor #1 | | | |
| Lymphocyte | 81(24%) | 145(25%) | 1.79 |
| Monocyte | 83 | 200 | 2.41 |
| Neutrophil | 296 | 296 | 1.00 |
| Donor #2 | | | |
| Lymphocyte | 0(0%) | 42(18%) | ND |
| Monocyte | 11 | 71 | 6.45 |
| Neutrophil | 131 | 216 | 1.65 |
| Donor #3 | | | |
| Lymphocyte | 58(12%) | 89(14%) | 1.53 |
| Monocyte | 34 | 163 | 4.79 |
| Neutrophil | 373 | 348 | 0.93 |
| Donor #4 | | | |
| Lymphocyte | 31(3%) | 196(9%) | 16.33 |
| Monocyte | 77 | 154 | 2.00 |
| Neutrophil | 301 | 310 | 1.03 |
| Donor #5 | | | |
| Lymphocyte | 12(23.3%) | 72(6%) | 2.32 |
| Monocyte | 11 | 69 | 6.27 |
| Neutrophil | 149 | 125 | 0.84 |
| Donor #6 | | | |
| Lymphocyte | 6(0.8%) | 169(4.5%) | 28.17 |
| Monocyte | 13 | 73 | 5.62 |
| Neutrophil | 130 | 215 | 1.65 |

*Mean Fluorescence Unit (MFU) was determined by subtracting the fluorescence of unstained cells from the fluorescence of each population of cells stained with F-9H1 (anti-IL8R-A) or F-10H2 (anti-IL8R-B).
( ): percentage of total lymphocyte population expressing the particular IL8R.

Double colored FACS analysis was used to characterize the lymphocyte cell subpopulations that express IL8R (Table 7 and FIG. 17a–f). IL8R expression was found in 20–42% of CD8+ T-suppressor cells and in 39–76% of CD56+ NK cells. As shown in Table 7 and FIG. 17a–f, the expression level of IL8R-B is higher than the expression level of IL8R-A among IL8R-positive CD8+ T-suppressor cells and CD56+ NK cells. CD20+ B cells and CD4+ T cells did not exhibit IL8R expression.

TABLE 7

The proportion of CD8+ and CD56+ NK cells expressing IL8R-A and IL8R-B

| Donor | IL8R | % CD8+ | % CD56+ |
|---|---|---|---|
| No 1 | A | 40.6 | 67.9 |
| | B | 42.4 | 76.0 |
| No 2 | A | 3.4 | 1.8 |

TABLE 7-continued

| The proportion of CD8+ and CD56+ NK cells expressing IL8R-A and IL8R-B | | | |
|---|---|---|---|
| Donor | IL8R | % CD8+ | % CD56+ |
| | B | 19.7 | 58.8 |
| No 3 | A | 18.7 | 57.1 |
| | B | 21.2 | 59.5 |
| No 4 | A | 4.4 | 28.2 |
| | B | 7.1 | 42.6 |
| No 5 | A | 1.1 | 10.9 |
| | B | 20.8 | 62.9 |
| No 6 | A | 3.1 | 3.2 |
| | B | 18.2 | 39.3 |

EXAMPLE 5

Figure 11:
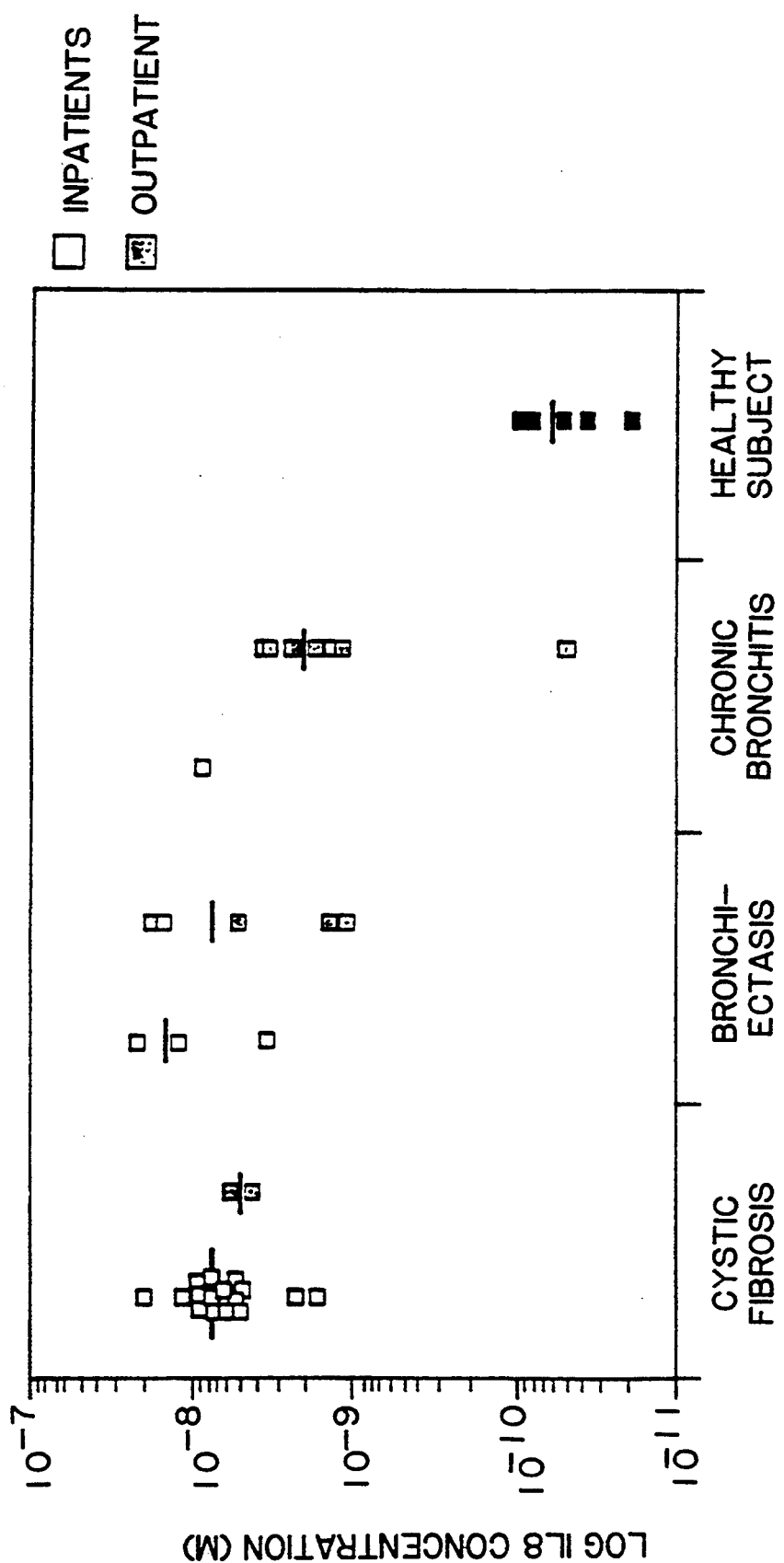
FIG. 11 shows the concentrations of IL-8 in sputum from various patients with chronic airway inflammation (cystic fibrosis, bronchiectasis, and chronic bronchitis) and induced sputum for healthy subjects, where the open squares are in-patients and the shaded squares are out-patients.

IL-8 was found to be present at high concentration and is the major neutrophil chemotactic factor in sputum from patients with chronic bronchitis, bronchiectasis, and cystic fibrosis. FIG. 11 shows the concentration of IL-8 in sputum from patients with chronic airway diseases and in sputum induced from healthy patients.

One of the four antibodies 4D1, 10H2, 2A4 or 9H1 described above is injected intravenously every two weeks in a dose of 1-15 mg/$k_9$ in patients having asthma, chronic bronchitis, bronchiectasis, cystic fibrosis, rheumatoid arthritis, or ulcerative colitis. For treating an acute indication, adult respiratory distress syndrome, a dose of 10-100 mg/kg of one of the antibodies is injected a single time intravenously. It would be expected that the anti-IL8R-B antibodies that block IL8R-B activity (MAbs 4D1 and 10H2) or the anti-IL8R-A antibodies that block IL8R-A activity (2A4 and 9H1) would be effective in reducing the inflammation associated with each of the disorders described above. The antibodies are also expected to be efficacious in treating human pleurisy, vasculitis, alveolitis, and pneumonia.

The following hybridomas have been deposited with the American Type Culture Collection, 12301 Parklawn Drive, Rockville, Md., USA (ATCC):

| Cell Lines | ATCC Accession No. | Deposit Date |
|---|---|---|
| 10H2 | HB 11494 | Dec. 1, 1993 |
| 4D1 | HB 11495 | Dec. 2, 1993 |

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 350 amino acids
        ( B ) TYPE: amino acid
        ( D ) TOPOLOGY: linear ( x i ) SEQUENCE DESCRIPTION: SEQ ID NO:1:

```
Met Ser Asn Ile Thr Asp Pro Gln Met Trp Asp Phe Asp Asp Leu
 1               5                  10                  15

Asn Phe Thr Gly Met Pro Pro Ala Asp Glu Asp Tyr Ser Pro Cys
                20                  25                  30

Met Leu Glu Thr Glu Thr Leu Asn Lys Tyr Val Val Ile Ile Ala
                35                  40                  45

Tyr Ala Leu Val Phe Leu Leu Ser Leu Leu Gly Asn Ser Leu Val
                50                  55                  60

Met Leu Val Ile Leu Tyr Ser Arg Val Gly Arg Ser Val Thr Asp
                65                  70                  75

Val Tyr Leu Leu Asn Leu Ala Leu Ala Asp Leu Leu Phe Ala Leu
                80                  85                  90

Thr Leu Pro Ile Trp Ala Ala Ser Lys Val Asn Gly Trp Ile Phe
                95                 100                 105

Gly Thr Phe Leu Cys Lys Val Val Ser Leu Leu Lys Glu Val Asn
               110                 115                 120

Phe Tyr Ser Gly Ile Leu Leu Leu Ala Cys Ile Ser Val Asp Arg
               125                 130                 135

Tyr Leu Ala Ile Val His Ala Thr Arg Thr Leu Thr Gln Lys Arg
               140                 145                 150

His Leu Val Lys Phe Val Cys Leu Gly Cys Trp Gly Leu Ser Met
               155                 160                 165

Asn Leu Ser Leu Pro Phe Phe Leu Phe Arg Gln Ala Tyr His Pro
               170                 175                 180

Asn Asn Ser Ser Pro Val Cys Tyr Glu Val Leu Gly Asn Asp Thr
```

|     |     |     |     | 185 |     |     |     |     | 190 |     |     |     |     | 195 |
|-----|-----|-----|-----|-----|-----|-----|-----|-----|-----|-----|-----|-----|-----|-----|
| Ala | Lys | Trp | Arg | Met | Val | Leu | Arg | Ile | Leu | Pro | His | Thr | Phe | Gly |
|     |     |     |     | 200 |     |     |     |     | 205 |     |     |     |     | 210 |
| Phe | Ile | Val | Pro | Leu | Phe | Val | Met | Leu | Phe | Cys | Tyr | Gly | Phe | Thr |
|     |     |     |     | 215 |     |     |     |     | 220 |     |     |     |     | 225 |
| Leu | Arg | Thr | Leu | Phe | Lys | Ala | His | Met | Gly | Gln | Lys | His | Arg | Ala |
|     |     |     |     | 230 |     |     |     |     | 235 |     |     |     |     | 240 |
| Met | Arg | Val | Ile | Phe | Ala | Val | Val | Leu | Ile | Phe | Leu | Leu | Cys | Trp |
|     |     |     |     | 245 |     |     |     |     | 250 |     |     |     |     | 255 |
| Leu | Pro | Tyr | Asn | Leu | Val | Leu | Leu | Ala | Asp | Thr | Leu | Met | Arg | Thr |
|     |     |     |     | 260 |     |     |     |     | 265 |     |     |     |     | 270 |
| Gln | Val | Ile | Gln | Glu | Thr | Cys | Glu | Arg | Arg | Asn | Asn | Ile | Gly | Arg |
|     |     |     |     | 275 |     |     |     |     | 280 |     |     |     |     | 285 |
| Ala | Leu | Asp | Ala | Thr | Glu | Ile | Leu | Gly | Phe | Leu | His | Ser | Cys | Leu |
|     |     |     |     | 290 |     |     |     |     | 295 |     |     |     |     | 300 |
| Asn | Pro | Ile | Ile | Tyr | Ala | Phe | Ile | Gly | Gln | Asn | Phe | Arg | His | Gly |
|     |     |     |     | 305 |     |     |     |     | 310 |     |     |     |     | 315 |
| Phe | Leu | Lys | Ile | Leu | Ala | Met | His | Gly | Leu | Val | Ser | Lys | Glu | Phe |
|     |     |     |     | 320 |     |     |     |     | 325 |     |     |     |     | 330 |
| Leu | Ala | Arg | His | Arg | Val | Thr | Ser | Tyr | Thr | Ser | Ser | Ser | Val | Asn |
|     |     |     |     | 335 |     |     |     |     | 340 |     |     |     |     | 345 |
| Val | Ser | Ser | Asn | Leu |     |     |     |     |     |     |     |     |     |     |
|     |     |     |     | 350 |     |     |     |     |     |     |     |     |     |     |

( 2 ) INFORMATION FOR SEQ ID NO:2:

( i ) SEQUENCE CHARACTERISTICS:
        ( A ) LENGTH: 1883 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

| | | | | |
|---|---|---|---|---|
| ATGTCAAATA | TTACAGATCC | ACAGATGTGG | GATTTTGATG | ATCTAAATTT | 50 |
| CACTGGCATG | CCACCTGCAG | ATGAAGATTA | CAGCCCCTGT | ATGCTAGAAA | 100 |
| CTGAGACACT | CAACAAGTAT | GTTGTGATCA | TCGCCTATGC | CCTAGTGTTC | 150 |
| CTGCTGAGCC | TGCTGGGAAA | CTCCCTGGTG | ATGCTGGTCA | TCTTATACAG | 200 |
| CAGGGTCGGC | CGCTCCGTCA | CTGATGTCTA | CCTGCTGAAC | CTGGCCTTGG | 250 |
| CCGACCTACT | CTTTGCCCTG | ACCTTGCCCA | TCTGGGCCGC | CTCCAAGGTG | 300 |
| AATGGCTGGA | TTTTTGGCAC | ATTCCTGTGC | AAGGTGGTCT | CACTCCTGAA | 350 |
| GGAAGTCAAC | TTCTACAGTG | GCATCCTGCT | GTTGGCCTGC | ATCAGTGTGG | 400 |
| ACCGTTACCT | GGCCATTGTC | CATGCCACAC | GCACACTGAC | CCAGAAGCGT | 450 |
| CACTTGGTCA | AGTTTGTTTG | TCTTGGCTGC | TGGGGACTGT | CTATGAATCT | 500 |
| GTCCCTGCCC | TTCTTCCTTT | TCCGCCAGGC | TTACCATCCA | AACAATTCCA | 550 |
| GTCCAGTTTG | CTATGAGGTC | CTGGGAAATG | ACACAGCAAA | ATGGCGGATG | 600 |
| GTGTTGCGGA | TCCTGCCTCA | CACCTTTGGC | TTCATCGTGC | CGCTGTTTGT | 650 |
| CATGCTGTTC | TGCTATGGAT | TCACCCTGCG | TACACTGTTT | AAGGCCCACA | 700 |
| TGGGGCAGAA | GCACCGAGCC | ATGAGGGTCA | TCTTTGCTGT | CGTCCTCATC | 750 |
| TTCCTGCTTT | GCTGGCTGCC | CTACAACCTG | GTCCTGCTGG | CAGACACCCT | 800 |
| CATGAGGACC | CAGGTGATCC | AGGAGACCTG | TGAGCGCCGC | AACAACATCG | 850 |
| GCCGGGCCCT | GGATGCCACT | GAGATTCTGG | GATTTCTCCA | TAGCTGCCTC | 900 |

-continued

```
AACCCCATCA TCTACGCCTT CATCGGCCAA AATTTTCGCC ATGGATTCCT   950
CAAGATCCTG GCTATGCATG GCCTGGTCAG CAAGGAGTTC TTGGCACGTC  1000
ATCGTGTTAC CTCCTACACT TCTTCGTCTG TCAATGTCTC TTCCAACCTC  1050
TGAAAACCAT CGATGAAGGA ATATCTCTTC TCAGAAGGAA AGAATAACCA  1100
ACACCCTGAG GTTGTGTGTG GAAGGTGATC TGGCTCTGGA CAGGCACTAT  1150
CTGGGTTTTG GGGGACGCT ATAGGATGTG GGGAAGTTAG GAACTGGTGT   1200
CTTCAGGGGC CACACCAACC TTCTGAGGAG CTGTTGAGGT ACCTCCAAGG  1250
ACCGGCCTTT GCACCTCCAT GGAAACGAAG CACCATCATT CCCGTTGAAC  1300
GTCACATCTT TAACCCACTA ACTGGCTAAT TAGCATGGCC ACATCTGAGC  1350
CCCGAATCTG ACATTAGATG AGAGAACAGG GCTGAAGCTG TGTCCTCATG  1400
AGGGCTGGAT GCTCTCGTTG ACCCTCACAG GAGCATCTCC TCAACTCTGA  1450
GTGTTAAGCG TTGAGCCACC AAGCTGGTGG CTCTGTGTGC TCTGATCCGA  1500
GCTCAGGGGG GTGGTTTTCC CATCTCAGGT GTGTTGCAGT GTCTGCTGGA  1550
GACATTGAGG CAGGCACTGC CAAAACATCA ACCTGCCAGC TGGCCTTGTG  1600
AGGAGCTGGA AACACATGTT CCCCTTGGGG GTGGTGGATG AACAAAGAGA  1650
AAGAGGGTTT GGAAGCCAGA TCTATGCCAC AAGAACCCCC TTTACCCCCA  1700
TGACCAACAT CGCAGACACA TGTGCTGGCC ACCTGCTGAG CCCCAAGTGG  1750
AACGAGACAA GCAGCCCTTA GCCCTTCCCC TCTGCAGCTT CCAGGCTGGC  1800
GTGCAGCATC AGCATCCCTA GAAAGCCATG TGCAGCCACC AGTCCATTGG  1850
GCAGGCAGAT GTTCCTAATA AAGCTTCTGT TCC                    1883
```

( 2 ) INFORMATION FOR SEQ ID NO:3:

( i ) SEQUENCE CHARACTERISTICS:
        ( A ) LENGTH: 352 amino acids
        ( B ) TYPE: amino acid
        ( D ) TOPOLOGY: linear ( x i ) SEQUENCE DESCRIPTION: SEQ ID NO:3:

```
Met Glu Gly Ile Ser Ile Tyr Thr Ser Asp Asn Tyr Thr Glu Glu
 1               5                  10                  15

Met Gly Ser Gly Asp Tyr Asp Ser Met Lys Glu Pro Cys Phe Arg
                20                  25                  30

Glu Glu Asn Ala Asn Phe Asn Lys Ile Phe Leu Pro Thr Ile Tyr
                35                  40                  45

Ser Ile Ile Phe Leu Thr Gly Ile Val Gly Asn Gly Leu Val Ile
                50                  55                  60

Leu Val Met Gly Tyr Gln Lys Lys Leu Arg Ser Met Thr Asp Lys
                65                  70                  75

Tyr Arg Leu His Leu Ser Val Ala Asp Leu Leu Phe Val Ile Thr
                80                  85                  90

Leu Pro Phe Trp Ala Val Asp Ala Val Ala Asn Trp Tyr Phe Gly
                95                 100                 105

Asn Phe Leu Cys Lys Ala Val His Val Ile Tyr Thr Val Asn Leu
               110                 115                 120

Tyr Ser Ser Val Leu Ile Leu Ala Phe Ile Ser Leu Asp Arg Tyr
               125                 130                 135

Leu Ala Ile Val His Ala Thr Asn Ser Gln Arg Pro Arg Lys Leu
               140                 145                 150

Leu Ala Glu Lys Val Val Tyr Val Gly Val Trp Ile Pro Ala Leu
               155                 160                 165
```

| | | | | | | | | | | | |
|---|---|---|---|---|---|---|---|---|---|---|---|
| Leu | Leu | Thr | Ile | Pro | Asp | Phe | Ile | Phe | Ala | Asn | Val | Ser | Glu | Ala |
| | | | | 170 | | | | 175 | | | | | | 180 |
| Asp | Asp | Arg | Tyr | Ile | Cys | Asp | Arg | Phe | Tyr | Pro | Asn | Asp | Leu | Trp |
| | | | | 185 | | | | 190 | | | | | | 195 |
| Val | Val | Val | Phe | Gln | Phe | Gln | His | Ile | Met | Val | Gly | Leu | Ile | Leu |
| | | | | 200 | | | | 205 | | | | | | 210 |
| Pro | Gly | Ile | Val | Ile | Leu | Ser | Cys | Tyr | Cys | Ile | Ile | Ile | Ser | Lys |
| | | | | 215 | | | | 220 | | | | | | 225 |
| Leu | Ser | His | Ser | Lys | Gly | His | Gln | Lys | Arg | Lys | Ala | Leu | Lys | Thr |
| | | | | 230 | | | | 235 | | | | | | 240 |
| Thr | Val | Ile | Leu | Ile | Leu | Ala | Phe | Phe | Ala | Cys | Trp | Leu | Pro | Tyr |
| | | | | 245 | | | | 250 | | | | | | 255 |
| Tyr | Ile | Gly | Ile | Ser | Ile | Asp | Ser | Phe | Ile | Leu | Leu | Glu | Ile | Ile |
| | | | | 260 | | | | 265 | | | | | | 270 |
| Lys | Gln | Gly | Cys | Glu | Phe | Glu | Asn | Thr | Val | His | Lys | Trp | Ile | Ser |
| | | | | 275 | | | | 280 | | | | | | 285 |
| Ile | Thr | Glu | Ala | Leu | Ala | Phe | Phe | His | Cys | Cys | Leu | Asn | Pro | Ile |
| | | | | 290 | | | | 295 | | | | | | 300 |
| Leu | Tyr | Ala | Phe | Leu | Gly | Ala | Lys | Phe | Lys | Thr | Ser | Ala | Gln | His |
| | | | | 305 | | | | 310 | | | | | | 315 |
| Ala | Leu | Thr | Ser | Val | Ser | Arg | Gly | Ser | Ser | Leu | Lys | Ile | Leu | Ser |
| | | | | 320 | | | | 325 | | | | | | 330 |
| Lys | Gly | Lys | Arg | Gly | Gly | His | Ser | Ser | Val | Ser | Thr | Glu | Ser | Glu |
| | | | | 335 | | | | 340 | | | | | | 345 |
| Ser | Ser | Ser | Phe | His | Ser | Ser | | | | | | | | |
| | | | | 350 | | 352 | | | | | | | | |

( 2 ) INFORMATION FOR SEQ ID NO:4:

( i ) SEQUENCE CHARACTERISTICS:
( A ) LENGTH: 1737 bases
( B ) TYPE: nucleic acid
( C ) STRANDEDNESS: single
( D ) TOPOLOGY: linear ( x i ) SEQUENCE DESCRIPTION: SEQ ID NO:4:

```
GAATTCCAGT GTGCTGGCGG CGCGGCGCAA AGTGACGCCG AGGGCCTGAG   50
TGCTCCAGTA GCCACCGCAT CTGGAGAACC AGCGGTTACC ATGGAGGGGA  100
TCAGTATATA CACTTCAGAT AACTACACCG AGGAAATGGG CTCAGGGGAC  150
TATGACTCCA TGAAGGAACC CTGTTTCCGT GAAGAAAATG CTAATTTCAA  200
TAAAATCTTC CTGCCCACCA TCTACTCCAT CATCTTCTTA ACTGGCATTG  250
TGGGCAATGG ATTGGTCATC CTGGTCATGG GTTACCAGAA GAAACTGAGA  300
AGCATGACGG ACAAGTACAG GCTGCACCTG TCAGTGGCCG ACCTCCTCTT  350
TGTCATCACG CTTCCCTTCT GGGCAGTTGA TGCCGTGGCA AACTGGTACT  400
TTGGGAACTT CCTATGCAAG GCAGTCCATG TCATCTACAC AGTCAACCTC  450
TACAGCAGTG TCCTCATCCT GGCCTTCATC AGTCTGGACC GCTACCTGGC  500
CATCGTCCAC GCCACCAACA GTCAGAGGCC AAGGAAGCTG TTGGCTGAAA  550
AGGTGGTCTA TGTTGGCGTC TGGATCCCTG CCCTCCTGCT GACTATTCCC  600
GACTTCATCT TTGCCAACGT CAGTGAGGCA GATGACAGAT ATATCTGTGA  650
CCGCTTCTAC CCCAATGACT TGTGGGTGGT TGTGTTCCAG TTTCAGCACA  700
TCATGGTTGG CCTTATCCTG CCTGGTATTG TCATCCTGTC CTGCTATTGC  750
ATTATCATCT CCAAGCTGTC ACACTCCAAG GGCCACCAGA AGCGCAAGGC  800
```

-continued

```
CCTCAAGACC ACAGTCATCC TCATCCTGGC TTTCTTCGCC TGTTGGCTGC    850
CTTACTACAT TGGGATCAGC ATCGACTCCT TCATCCTCCT GGAAATCATC    900
AAGCAAGGGT GTGAGTTTGA GAACACTGTG CACAAGTGGA TTTCCATCAC    950
CGAGGCCCTA GCTTTCTTCC ACTGTTGTCT GAACCCCATC CTCTATGCTT   1000
TCCTTGGAGC CAAATTTAAA ACCTCTGCCC AGCACGCACT CACCTCTGTG   1050
AGCAGAGGGT CCAGCCTCAA GATCCTCTCC AAAGGAAAGC GAGGTGGACA   1100
TTCATCTGTT TCCACTGAGT CTGAGTCTTC AAGTTTTCAC TCCAGCTAAC   1150
ACAGATGTAA AAGACTTTTT TTTATACGAT AAATAACTTT TTTTAAGTT    1200
ACACATTTTT CAGATATAAA AGACTGACCA ATATTGTACA GTTTTATTG    1250
CTTGTTGGAT TTTTGTCTTG TGTTTCTTTA GTTTTGTGA AGTTTAATTG    1300
ACTTATTTAT ATAAATTTTT TTGTTTCAT ATTGATGTGT GTCTAGGCAG    1350
GACCTGTGGC CAAGTTCTTA GTTGCTGTAT GTCTCGTGGT AGGACTGTAG   1400
AAAAGGGAAC TGAACATTCC AGAGCGTGTA GTGAATCACG TAAAGCTAGA   1450
AATGATCCCC AGCTGTTTAT GCATAGATAA TCTCTCCATT CCCGTGGAAC   1500
GTTTTCCTG  TTCTTAAGAC GTGATTTTGC TGTAGAAGAT GGCACTTATA   1550
ACCAAAGCCC AAAGTGGTAT AGAAATGCTG GTTTTCAGT  TTTCAGGAGT   1600
GGGTTGATTT CAGCACCTAC AGTGTACAGT CTTGTATTAA GTTGTTAATA   1650
AAAGTACATG TTAAACTTAA AAAAAAAAAA AAAAAAAAAA AAAAAAAAAA   1700
AAAAAAAAAA AAAGCGGCCG CCAGCACACT GGAATTC                 1737
```

( 2 ) INFORMATION FOR SEQ ID NO:5:

( i ) SEQUENCE CHARACTERISTICS:
( A ) LENGTH: 372 amino acids
( B ) TYPE: amino acid
( D ) TOPOLOGY: linear ( x i ) SEQUENCE DESCRIPTION: SEQ ID NO:5:

```
Met Asn Tyr Pro Leu Thr Leu Glu Met Asp Leu Glu Asn Leu Glu
 1               5                  10                  15

Asp Leu Phe Trp Glu Leu Asp Arg Leu Asp Asn Tyr Asn Asp Thr
                20                  25                  30

Ser Leu Val Glu Asn His Leu Cys Pro Ala Thr Glu Gly Pro Leu
                35                  40                  45

Met Ala Ser Phe Lys Ala Val Phe Val Pro Val Ala Tyr Ser Leu
                50                  55                  60

Ile Phe Leu Leu Gly Val Ile Gly Asn Val Leu Val Leu Val Ile
                65                  70                  75

Leu Glu Arg His Arg Gln Thr Arg Ser Ser Thr Glu Thr Phe Leu
                80                  85                  90

Phe His Leu Ala Val Ala Asp Leu Leu Leu Val Phe Ile Leu Pro
                95                 100                 105

Phe Ala Val Ala Glu Gly Ser Val Gly Trp Val Leu Gly Thr Phe
               110                 115                 120

Leu Cys Lys Thr Val Ile Ala Leu His Lys Val Asn Phe Tyr Cys
               125                 130                 135

Ser Ser Leu Leu Leu Ala Cys Ile Ala Val Asp Arg Tyr Leu Ala
               140                 145                 150

Ile Val His Ala Val His Ala Tyr Arg His Arg Arg Leu Leu Ser
               155                 160                 165
```

|   |   |   |   |   |   |   |   |   |   |   |   |
|---|---|---|---|---|---|---|---|---|---|---|---|
| Ile | His | Ile | Thr | Cys | Gly | Thr | Ile | Trp | Leu | Val | Gly | Phe | Leu | Leu |
|   |   |   | 170 |   |   |   | 175 |   |   |   |   |   | 180 |
| Ala | Leu | Pro | Glu | Ile | Leu | Phe | Ala | Lys | Val | Ser | Gln | Gly | His | His |
|   |   |   | 185 |   |   |   |   | 190 |   |   |   |   |   | 195 |
| Asn | Asn | Ser | Leu | Pro | Arg | Cys | Thr | Phe | Ser | Gln | Glu | Asn | Gln | Ala |
|   |   |   |   | 200 |   |   |   |   | 205 |   |   |   |   | 210 |
| Glu | Thr | His | Ala | Trp | Phe | Thr | Ser | Arg | Phe | Leu | Tyr | His | Val | Ala |
|   |   |   |   | 215 |   |   |   |   | 220 |   |   |   |   | 225 |
| Gly | Phe | Leu | Leu | Pro | Met | Leu | Val | Met | Gly | Trp | Cys | Tyr | Val | Gly |
|   |   |   |   | 230 |   |   |   | 235 |   |   |   |   |   | 240 |
| Val | Val | His | Arg | Leu | Arg | Gln | Ala | Gln | Arg | Arg | Pro | Gln | Arg | Gln |
|   |   |   |   | 245 |   |   |   |   | 250 |   |   |   |   | 255 |
| Lys | Ala | Val | Arg | Val | Ala | Ile | Leu | Val | Thr | Ser | Ile | Phe | Phe | Leu |
|   |   |   |   | 260 |   |   |   |   | 265 |   |   |   |   | 270 |
| Cys | Trp | Ser | Pro | Tyr | His | Ile | Val | Ile | Phe | Leu | Asp | Thr | Leu | Ala |
|   |   |   |   | 275 |   |   |   |   | 280 |   |   |   |   | 285 |
| Arg | Leu | Lys | Ala | Val | Asp | Asn | Thr | Cys | Lys | Leu | Asn | Gly | Ser | Leu |
|   |   |   |   | 290 |   |   |   |   | 295 |   |   |   |   | 300 |
| Pro | Val | Ala | Ile | Thr | Met | Cys | Glu | Phe | Leu | Gly | Leu | Ala | His | Cys |
|   |   |   |   | 305 |   |   |   |   | 310 |   |   |   |   | 315 |
| Cys | Leu | Asn | Pro | Met | Leu | Tyr | Thr | Phe | Ala | Gly | Val | Lys | Phe | Arg |
|   |   |   |   | 320 |   |   |   |   | 325 |   |   |   |   | 330 |
| Ser | Asp | Leu | Ser | Arg | Leu | Leu | Thr | Lys | Leu | Gly | Cys | Thr | Gly | Pro |
|   |   |   |   | 335 |   |   |   |   | 340 |   |   |   |   | 345 |
| Ala | Ser | Leu | Cys | Gln | Leu | Phe | Pro | Ser | Trp | Arg | Arg | Ser | Ser | Leu |
|   |   |   |   | 350 |   |   |   |   | 355 |   |   |   |   | 360 |
| Ser | Glu | Ser | Glu | Asn | Ala | Thr | Ser | Leu | Thr | Thr | Phe |
|   |   |   |   | 365 |   |   |   | 370 |   | 372 |

( 2 ) INFORMATION FOR SEQ ID NO:6:

( i ) SEQUENCE CHARACTERISTICS:
        ( A ) LENGTH: 1679 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
GAATTCCAGT GTGCTGGCGG CCGCCCAGTG TGCTGGCGGC GGCAGTTGAG   50
GGAAAGGACA GAGGTTATGA GTGCCTGCAA GAGTGGCAGC CTGGAGTAGA  100
GAAAACACTA AAGGTGGAGT CAAAAGACCT GAGTTCAAGT CCCAGCTCTG  150
CCACTGGTTA GCTGTGGGAT CTCGGAAAAG ACCCAGTGAA AAAAAAAAAA  200
AAAGTGATGA GTTGTGAGGC AGGTCGCGGC CCTACTGCCT CAGGAGACGA  250
TGCGCAGCTC ATTTGCTTAA ATTTGCAGCT GACGGCTGCC ACCTCTCTAG  300
AGGCACCTGG CGGGGAGCCT CTCAACATAA GACAGTGACC AGTCTGGTGA  350
CTCACAGCCG GCACAGCCAT GAACTACCCG CTAACGCTGG AAATGGACCT  400
CGAGAACCTG GAGGACCTGT TCTGGGAACT GGACAGATTG GACAACTATA  450
ACGACACCTC CCTGGTGGAA AATCATCTCT GCCCTGCCAC AGAGGGGCCC  500
CTCATGGCCT CCTTCAAGGC CGTGTTCGTG CCCGTGGCCT ACAGCCTCAT  550
CTTCCTCCTG GGCGTGATCG GCAACGTCCT GGTGCTGGTG ATCCTGGAGC  600
GGCACCGGCA GACACGCAGT TCCACGGAGA CCTTCCTGTT CCACCTGGCC  650
GTGGCCGACC TCCTGCTGGT CTTCATCTTG CCCTTTGCCG TGGCCGAGGG  700
CTCTGTGGGC TGGGTCCTGG GGACCTTCCT CTGCAAAACT GTGATTGCCC  750
```

-continued

```
TGCACAAAGT CAACTTCTAC TGCAGCAGCC TGCTCCTGGC CTGCATCGCC    800
GTGGACCGCT ACCTGGCCAT TGTCCACGCC GTCCATGCCT ACCGCCACCG    850
CCGCCTCCTC TCCATCCACA TCACCTGTGG GACCATCTGG CTGGTGGGCT    900
TCCTCCTTGC CTTGCCAGAG ATTCTCTTCG CCAAAGTCAG CCAAGGCCAT    950
CACAACAACT CCCTGCCACG TTGCACCTTC TCCAAGAGA ACCAAGCAGA    1000
AACGCATGCC TGGTTCACCT CCCGATTCCT CTACCATGTG GCGGGATTCC    1050
TGCTGCCCAT GCTGGTGATG GGCTGGTGCT ACGTGGGGGT AGTGCACAGG    1100
TTGCGCCAGG CCCAGCGGCG CCCTCAGCGG CAGAAGGCAG TCAGGGTGGC    1150
CATCCTGGTG ACAAGCATCT TCTTCCTCTG CTGGTCACCC TACCACATCG    1200
TCATCTTCCT GGACACCCTG GCGAGGCTGA AGGCCGTGGA CAATACCTGC    1250
AAGCTGAATG CTCTCTCCC CGTGGCCATC ACCATGTGTG AGTTCCTGGG    1300
CCTGGCCCAC TGCTGCCTCA ACCCCATGCT CTACACTTTC GCCGGCGTGA    1350
AGTTCCGCAG TGACCTGTCG CGGCTCCTGA CGAAGCTGGG CTGTACCGGC    1400
CCTGCCTCCC TGTGCCAGCT CTTCCCTAGC TGGCGCAGGA GCAGTCTCTC    1450
TGAGTCAGAG AATGCCACCT CTCTCACCAC GTTCTAGGTC CCAGTGTCCC    1500
CTTTTATTGC TGCTTTTCCT TGGGGCAGGC AGTGATGCTG GATGCTCCTT    1550
CCAACAGGAG CTGGGATCCT AAGGGCTCAC CGTGGCTAAG AGTGTCCTAG    1600
GAGTATCCTC ATTTGGGGTA GCTAGAGGAA CCAACCCCCA TTTCTAGAAC    1650
ATCCCGCGGC CGCCAGCACA CTGGAATTC                          1679
```

( 2 ) INFORMATION FOR SEQ ID NO:7:

( i ) SEQUENCE CHARACTERISTICS:
( A ) LENGTH: 360 amino acids
( B ) TYPE: amino acid
( D ) TOPOLOGY: linear ( x i ) SEQUENCE DESCRIPTION: SEQ ID NO:7:

```
Met Glu Asp Phe Asn Met Glu Ser Asp Ser Phe Glu Asp Phe Trp
 1               5                  10                  15

Lys Gly Glu Asp Leu Ser Asn Tyr Ser Ser Thr Leu Pro
                20                  25                  30

Pro Phe Leu Leu Asp Ala Ala Pro Cys Glu Pro Glu Ser Leu Glu
                35                  40                  45

Ile Asn Lys Tyr Phe Val Val Ile Ile Tyr Ala Leu Val Phe Leu
                50                  55                  60

Leu Ser Leu Leu Gly Asn Ser Leu Val Met Leu Val Ile Leu Tyr
                65                  70                  75

Ser Arg Val Gly Arg Ser Val Thr Asp Val Tyr Leu Leu Asn Leu
                80                  85                  90

Ala Leu Ala Asp Leu Leu Phe Ala Leu Thr Leu Pro Ile Trp Ala
                95                  100                 105

Ala Ser Lys Val Asn Gly Trp Ile Phe Gly Thr Phe Leu Cys Lys
                110                 115                 120

Val Val Ser Leu Leu Lys Glu Val Asn Phe Tyr Ser Gly Ile Leu
                125                 130                 135

Leu Leu Ala Cys Ile Ser Val Asp Arg Tyr Leu Ala Ile Val His
                140                 145                 150

Ala Thr Arg Thr Leu Thr Gln Lys Arg Tyr Leu Val Lys Phe Ile
                155                 160                 165
```

```
Cys Leu Ser Ile Trp Gly Leu Ser Leu Leu Leu Ala Leu Pro Val
            170                 175                 180

Leu Leu Phe Arg Arg Thr Val Tyr Ser Ser Asn Val Ser Pro Ala
            185                 190                 195

Cys Tyr Glu Asp Met Gly Asn Asn Thr Ala Asn Trp Arg Met Leu
            200                 205                 210

Leu Arg Ile Leu Pro Gln Ser Phe Gly Phe Ile Val Pro Leu Leu
            215                 220                 225

Ile Met Leu Phe Cys Tyr Gly Phe Thr Leu Arg Thr Leu Phe Lys
            230                 235                 240

Ala His Met Gly Gln Lys His Arg Ala Met Arg Val Ile Phe Ala
            245                 250                 255

Val Val Leu Ile Phe Leu Leu Cys Trp Leu Pro Tyr Asn Leu Val
            260                 265                 270

Leu Leu Ala Asp Thr Leu Met Arg Thr Gln Val Ile Gln Glu Thr
            275                 280                 285

Cys Glu Arg Arg Asn His Ile Asp Arg Ala Leu Asp Ala Thr Glu
            290                 295                 300

Ile Leu Gly Ile Leu His Ser Cys Leu Asn Pro Leu Ile Tyr Ala
            305                 310                 315

Phe Ile Gly Gln Lys Phe Arg His Gly Leu Leu Lys Ile Leu Ala
            320                 325                 330

Ile His Gly Leu Ile Ser Lys Asp Ser Leu Pro Lys Asp Ser Arg
            335                 340                 345

Pro Ser Phe Val Gly Ser Ser Ser Gly His Thr Ser Thr Thr Leu
            350                 355                 360
```

(2) INFORMATION FOR SEQ ID NO:8:

(i) SEQUENCE CHARACTERISTICS:
        (A) LENGTH: 1748 bases
        (B) TYPE: nucleic acid
        (C) STRANDEDNESS: single
        (D) TOPOLOGY: linear (xi) SEQUENCE DESCRIPTION: SEQ ID NO:8:

```
CTACAGGTGA  AAAGCCCAGC  GACCCAGTCA  GGATTTAAGT  TTACCTCAAA  50
AATGGAAGAT  TTAACATGG   AGAGTGACAG  CTTTGAAGAT  TTCTGGAAAG  100
GTGAAGATCT  TAGTAATTAC  AGTTACAGCT  CTACCCTGCC  CCCTTTTCTA  150
CTAGATGCCG  CCCCATGTGA  ACCAGAATCC  CTGGAAATCA  CAAGTATTT   200
TGTGGTCATT  ATCTATGCCC  TGGTATTCCT  GCTGAGCCTG  CTGGGAAACT  250
CCCTCGTGAT  GCTGGTCATC  TTATACAGCA  GGGTCGGCCG  CTCCGTCACT  300
GATGTCTACC  TGCTGAACCT  AGCCTTGGCC  GACCTACTCT  TTGCCCTGAC  350
CTTGCCCATC  TGGGCCGCCT  CCAAGGTGAA  TGGCTGGATT  TTTGGCACAT  400
TCCTGTGCAA  GGTGGTCTCA  CTCCTGAAGG  AAGTCAACTT  CTATAGTGGC  450
ATCCTGCTAC  TGGCCTGCAT  CAGTGTGGAC  CGTTACCTGG  CCATTGTCCA  500
TGCCACACGC  ACACTGACCC  AGAAGCGCTA  CTTGGTCAAA  TTCATATGTC  550
TCAGCATCTG  GGGTCTGTCC  TTGCTCCTGG  CCCTGCCTGT  CTTACTTTTC  600
CGAAGGACCG  TCTACTCATC  CAATGTTAGC  CCAGCCTGCT  ATGAGGACAT  650
GGGCAACAAT  ACAGCAAACT  GGCGGATGCT  GTTACGGATC  CTGCCCCAGT  700
CCTTTGGCTT  CATCGTGCCA  CTGCTGATCA  TGCTGTTCTG  CTACGGATTC  750
ACCCTGCGTA  CGCTGTTTAA  GGCCCACATG  GGGCAGAAGC  ACCGGGCCAT  800
```

| | | | | |
|---|---|---|---|---|
| GCGGGTCATC | TTTGCTGTCG | TCCTCATCTT | CCTGCTTTGC | TGGCTGCCCT  850 |
| ACAACCTGGT | CCTGCTGGCA | GACACCCTCA | TGAGGACCCA | GGTGATCCAG  900 |
| GAGACCTGTG | AGCGCCGCAA | TCACATCGAC | CGGGCTCTGG | ATGCCACCGA  950 |
| GATTCTGGGC | ATCCTTCACA | GCTGCCTCAA | CCCCCTCATC | TACGCCTTCA 1000 |
| TTGGCCAGAA | GTTTCGCCAT | GGACTCCTCA | AGATTCTAGC | TATACATGGC 1050 |
| TTGATCAGCA | AGGACTCCCT | GCCCAAAGAC | AGCAGGCCTT | CCTTTGTTGG 1100 |
| CTCTTCTTCA | GGGCACACTT | CCACTACTCT | CTAAGACCTC | CTGCCTAAGT 1150 |
| GCAGCCCCGT | GGGGTTCCTC | CCTTCTCTTC | ACAGTCACAT | TCCAAGCCTC 1200 |
| ATGTCCACTG | GTTCTTCTTG | GTCTCAGTGT | CAATGCAGCC | CCCATTGTGG 1250 |
| TCACAGGAAG | CAGAGGAGGC | CACGTTCTTA | CTAGTTTCCC | TTGCATGGTT 1300 |
| TAGAAAGCTT | GCCCTGGTGC | CTCACCCCTT | GCCATAATTA | CTATGTCATT 1350 |
| TGCTGGAGCT | CTGCCCATCC | TGCCCCTGAG | CCCATGGCAC | TCTATGTTCT 1400 |
| AAGAAGTGAA | AATCTACACT | CCAGTGAGAC | AGCTCTGCAT | ACTCATTAGG 1450 |
| ATGGCTAGTA | TCAAAAGAAA | GAAAATCAGG | CTGGCCAACG | GGATGAAACC 1500 |
| CTGTCTCTAC | TAAAAATACA | AAAAAAAAAA | AAAAAATTAG | CCGGGCGTGG 1550 |
| TGGTGAGTGC | CTGTAATCAC | AGCTACTTGG | GAGGCTGAGA | TGGGAGAATC 1600 |
| ACTTGAACCC | GGGAGGCAGA | GGTTGCAGTG | AGCCGAGATT | GTGCCCCTGC 1650 |
| ACTCCAGCCT | GAGCGACAGT | GAGACTCTGT | CTCAGTCCAT | GAAGATGTAG 1700 |
| AGGAGAAACT | GGAACTCTCG | AGCGTTGCTG | GGGGGATTG | TAAAATGG   1748 |

What is claimed is:

1. An anti-IL8R-B antibody.
2. The antibody of claim 1 that is a monoclonal antibody.
3. The antibody of claim 1 that has the isotype IgG2a.
4. The antibody of claim 1 that is a blocking anti-IL8R-B antibody.
5. The antibody of claim 4 that blocks the binding of IL-8 to IL8R-B.
6. The antibody of claim 5 that is a monoclonal antibody designated 4D1, having ATCC Deposit No. HB 11495.
7. The antibody of claim 5 that is a monoclonal antibody designated 10H2, having ATCC Deposit No. HB 11494.

* * * * *